(12) United States Patent
Assell et al.

(10) Patent No.: US 8,308,777 B2
(45) Date of Patent: Nov. 13, 2012

(54) METHOD AND APPARATUS FOR REMOVABLE SPINAL IMPLANT EXTENDING BETWEEN AT LEAST TWO ADJACENT VERTEBRAL BODIES

(75) Inventors: Robert L. Assell, Wilmington, NC (US); Stephen D. Ainsworth, Wilmington, NC (US); Brandon Arthurs, Wilmington, NC (US)

(73) Assignee: TranS1 Inc., Wilmington, NC (US)

( * ) Notice: Subject to any disclaimer, the term of this patent is extended or adjusted under 35 U.S.C. 154(b) by 216 days.

(21) Appl. No.: 12/870,000

(22) Filed: Aug. 27, 2010

(65) Prior Publication Data

US 2011/0060369 A1   Mar. 10, 2011

Related U.S. Application Data

(63) Continuation of application No. 12/367,397, filed on Feb. 6, 2009, now Pat. No. 7,914,535, which is a continuation of application No. 10/972,077, filed on Oct. 22, 2004, now Pat. No. 7,500,977.

(60) Provisional application No. 60/513,899, filed on Oct. 23, 2003.

(51) Int. Cl.
*A61B 17/88* (2006.01)

(52) U.S. Cl. .......................................... 606/279; 606/99

(58) Field of Classification Search ................... 606/246, 606/261, 262, 257; 623/17.11–17.13
See application file for complete search history.

(56) References Cited

U.S. PATENT DOCUMENTS

| | | | |
|---|---|---|---|
| 1,630,239 A | 5/1924 | Binkley et al. | |
| 2,336,338 A | 12/1943 | Zublin | |
| 3,103,926 A | 9/1963 | Cochran et al. | |
| 3,367,326 A | 2/1968 | Frazier | |
| 3,554,192 A | 1/1971 | Isberner | |
| 3,892,232 A | 7/1975 | Neufeld | |
| 4,135,506 A | 1/1979 | Ulrich | |
| 4,170,990 A | 10/1979 | Baumgart et al. | |
| 4,175,555 A | 11/1979 | Herbert | |
| 4,265,231 A | 5/1981 | Scheller, Jr. et al. | |
| 4,309,777 A | 1/1982 | Patil | |

(Continued)

FOREIGN PATENT DOCUMENTS

EP   0 611 116 B1   4/1994

(Continued)

OTHER PUBLICATIONS

B. Jeanneret, et al., "Posterior Stabilization in L5-S1 Isthmic Spondylolisthesis with Paralaminar Screw Fixation: Anatomical and Clinical Results," Journal of Spinal Disorders, vol. 9, No. 3, pp. 223-233 (1996) Lippincott-Raven Publishers, Philadelphia.

(Continued)

*Primary Examiner* — Andrew Yang
(74) *Attorney, Agent, or Firm* — Knobbe Martens Olson & Bear, LLP

(57) ABSTRACT

Disclosed are surgical tools, tool sets and methods for percutaneously accessing and preparing treatment sites within the spine for subsequent treatment procedures. The treatment site may be an inter-vertebral motion segments in the lumbar and sacral regions of the spine. The tool set may comprise introducer tools and bone dilators for accessing and tapping into a targeted site, such as, for example, the anterior surface of the S1 vertebral body. The tool set may also comprise cutters and extractors for preparing the treatment site for subsequent treatment procedures. The tool set may additionally comprise a bone graft inserter, an exchange system, and/or a temporary distraction tool for further preparing the treatment site for subsequent treatment procedures.

11 Claims, 51 Drawing Sheets

U.S. PATENT DOCUMENTS

| | | | |
|---|---|---|---|
| 4,401,112 A | 8/1983 | Rezaian | |
| 4,453,539 A | 6/1984 | Raftopoulos et al. | |
| 4,541,423 A | 9/1985 | Barber | |
| 4,553,273 A | 11/1985 | Wu | |
| 4,554,914 A | 11/1985 | Kapp et al. | |
| 4,573,448 A | 3/1986 | Kambin | |
| 4,636,217 A | 1/1987 | Ogilvie et al. | |
| 4,636,271 A | 1/1987 | Gandolfo | |
| 4,640,271 A | 2/1987 | Lower | |
| 4,650,466 A | 3/1987 | Luther | |
| 4,657,550 A | 4/1987 | Daher | |
| 4,756,649 A | 7/1988 | Heule | |
| 4,844,088 A | 7/1989 | Kambin | |
| 4,858,601 A | 8/1989 | Glisson | |
| 4,862,891 A | 9/1989 | Smith | |
| RE33,258 E | 7/1990 | Onik et al. | |
| RE33,348 E | 9/1990 | Lower | |
| 4,966,604 A | 10/1990 | Reiss | |
| 4,969,888 A | 11/1990 | Scholten et al. | |
| 5,002,546 A | 3/1991 | Romano | |
| 5,015,255 A | 5/1991 | Kuslich | |
| 5,019,079 A | 5/1991 | Ross | |
| 5,030,201 A | 7/1991 | Palestrant | |
| 5,059,193 A | 10/1991 | Kuslich | |
| 5,062,850 A | 11/1991 | Macmillan et al. | |
| 5,071,437 A | 12/1991 | Steffee | |
| 5,147,404 A | 9/1992 | Downey | |
| 5,171,279 A | 12/1992 | Mathews | |
| 5,190,546 A | 3/1993 | Jervis | |
| 5,192,326 A | 3/1993 | Bao et al. | |
| 5,195,968 A | 3/1993 | Lundquist et al. | |
| 5,236,460 A | 8/1993 | Barber | |
| 5,242,443 A | 9/1993 | Kambin | |
| 5,242,444 A | 9/1993 | MacMillan | |
| 5,242,461 A | 9/1993 | Kortenbach et al. | |
| 5,246,458 A | 9/1993 | Graham | |
| 5,258,031 A | 11/1993 | Salib et al. | |
| 5,269,785 A | 12/1993 | Bonutti | |
| 5,285,795 A | 2/1994 | Ryan et al. | |
| 5,290,289 A | 3/1994 | Sanders et al. | |
| 5,313,962 A | 5/1994 | Obenchain | |
| 5,336,223 A | 8/1994 | Rogers | |
| 5,357,983 A | 10/1994 | Mathews | |
| 5,360,448 A | 11/1994 | Thramann | |
| 5,366,457 A | 11/1994 | McGuire et al. | |
| 5,383,884 A | 1/1995 | Summers | |
| 5,395,188 A | 3/1995 | Bailey et al. | |
| 5,395,317 A | 3/1995 | Kambin | |
| 5,396,880 A | 3/1995 | Kagan et al. | |
| 5,403,276 A | 4/1995 | Schechter et al. | |
| 5,415,661 A | 5/1995 | Holmes | |
| 5,433,739 A | 7/1995 | Sluijter et al. | |
| 5,445,140 A | 8/1995 | Tovey | |
| 5,480,440 A | 1/1996 | Kambin | |
| 5,484,437 A | 1/1996 | Michelson | |
| 5,489,308 A | 2/1996 | Kuslich et al. | |
| 5,496,322 A | 3/1996 | Mathews | |
| 5,505,732 A | 4/1996 | Michelson | |
| 5,514,137 A | 5/1996 | Coutts | |
| 5,514,180 A | 5/1996 | Heggeness et al. | |
| 5,520,688 A | 5/1996 | Lin | |
| 5,534,031 A | 7/1996 | Matsuzaki et al. | |
| 5,545,228 A | 8/1996 | Kambin | |
| 5,549,679 A | 8/1996 | Kuslich | |
| 5,554,163 A | 9/1996 | Shturman | |
| 5,558,674 A | 9/1996 | Heggeness et al. | |
| 5,562,736 A | 10/1996 | Ray et al. | |
| 5,569,248 A | 10/1996 | Mathews | |
| 5,571,189 A | 11/1996 | Kuslich | |
| 5,571,190 A | 11/1996 | Ulrich et al. | |
| 5,571,192 A | 11/1996 | Schonhoffer | |
| 5,584,887 A | 12/1996 | Kambin | |
| 5,591,170 A | 1/1997 | Spievack et al. | |
| 5,591,235 A | 1/1997 | Kuslich | |
| 5,630,816 A | 5/1997 | Kambin | |
| 5,653,708 A | 8/1997 | Howland | |
| 5,665,122 A | 9/1997 | Kambin | |
| 5,669,909 A | 9/1997 | Zdeblick et al. | |
| 5,700,291 A | 12/1997 | Kuslich et al. | |
| 5,702,453 A | 12/1997 | Rabbe et al. | |
| 5,702,454 A | 12/1997 | Baumgartner | |
| 5,702,455 A | 12/1997 | Saggar | |
| 5,713,904 A | 2/1998 | Errico et al. | |
| 5,728,097 A | 3/1998 | Mathews | |
| 5,733,284 A | 3/1998 | Martin | |
| 5,735,899 A | 4/1998 | Schwartz et al. | |
| 5,741,253 A | 4/1998 | Michelson | |
| 5,741,261 A | 4/1998 | Moskovitz et al. | |
| 5,743,912 A | 4/1998 | Lahille et al. | |
| 5,762,629 A | 6/1998 | Kambin | |
| 5,779,704 A | 7/1998 | Kim | |
| 5,785,709 A | 7/1998 | Kummer et al. | |
| 5,792,044 A | 8/1998 | Foley et al. | |
| 5,827,285 A | 10/1998 | Bramlet | |
| 5,827,328 A | 10/1998 | Buttermann | |
| 5,885,292 A | 3/1999 | Moskovitz et al. | |
| 5,888,220 A | 3/1999 | Felt et al. | |
| 5,888,223 A | 3/1999 | Bray, Jr. | |
| 5,888,224 A * | 3/1999 | Beckers et al. | ............ 623/17.16 |
| 5,891,147 A | 4/1999 | Moskovitz et al. | |
| 5,902,231 A | 5/1999 | Foley et al. | |
| 5,906,616 A | 5/1999 | Pavolv et al. | |
| 5,916,267 A | 6/1999 | Tienboon | |
| 5,921,971 A | 7/1999 | Agro et al. | |
| 5,928,239 A | 7/1999 | Mirza | |
| 5,935,131 A | 8/1999 | Bonutti | |
| 5,954,635 A | 9/1999 | Foley et al. | |
| 5,961,329 A | 10/1999 | Stucki-McCormick | |
| 5,964,761 A | 10/1999 | Kambin | |
| 5,968,062 A | 10/1999 | Thomas et al. | |
| 5,972,015 A | 10/1999 | Scribner et al. | |
| 5,976,146 A | 11/1999 | Ogawa et al. | |
| 5,976,187 A | 11/1999 | Richelsoph | |
| 5,980,504 A | 11/1999 | Sharkey et al. | |
| 5,989,256 A | 11/1999 | Kuslich et al. | |
| 5,989,290 A | 11/1999 | Biedermann et al. | |
| 6,001,101 A | 12/1999 | Augagneur et al. | |
| 6,007,487 A | 12/1999 | Foley et al. | |
| 6,010,495 A | 1/2000 | Tilton, Jr. | |
| 6,010,502 A | 1/2000 | Bagby | |
| 6,019,792 A | 2/2000 | Cauthen | |
| 6,022,362 A | 2/2000 | Lee et al. | |
| 6,030,162 A | 2/2000 | Huebner | |
| 6,033,406 A | 3/2000 | Mathews | |
| 6,053,916 A | 4/2000 | Moore | |
| 6,056,749 A | 5/2000 | Kuslich | |
| 6,066,152 A | 5/2000 | Strauss et al. | |
| 6,066,154 A | 5/2000 | Reiley et al. | |
| 6,080,099 A | 6/2000 | Slater et al. | |
| 6,086,589 A | 7/2000 | Kuslich et al. | |
| 6,093,205 A | 7/2000 | McLeod | |
| 6,093,207 A | 7/2000 | Pisharodi | |
| 6,095,149 A | 8/2000 | Sharkey et al. | |
| 6,120,502 A | 9/2000 | Michelson | |
| 6,123,705 A | 9/2000 | Michelson | |
| 6,127,597 A | 10/2000 | Beyar et al. | |
| 6,152,871 A | 11/2000 | Foley et al. | |
| 6,159,212 A | 12/2000 | Schoedinger, III et al. | |
| 6,162,170 A | 12/2000 | Foley et al. | |
| 6,176,823 B1 | 1/2001 | Foley et al. | |
| 6,187,000 B1 | 2/2001 | Davison et al. | |
| 6,206,822 B1 | 3/2001 | Foley et al. | |
| 6,206,826 B1 | 3/2001 | Mathews et al. | |
| 6,210,412 B1 | 4/2001 | Michelson | |
| 6,217,509 B1 | 4/2001 | Foley et al. | |
| 6,241,735 B1 | 6/2001 | Marmulla | |
| 6,264,656 B1 | 7/2001 | Michelson | |
| 6,280,191 B1 | 8/2001 | Gordon | |
| 6,287,313 B1 | 9/2001 | Sasso | |
| 6,299,615 B1 | 10/2001 | Huebner | |
| 6,306,140 B1 | 10/2001 | Siddiqui | |
| 6,306,143 B1 | 10/2001 | Kvarnstrom et al. | |
| 6,315,795 B1 | 11/2001 | Scarborough et al. | |
| 6,319,254 B1 | 11/2001 | Giet et al. | |
| 6,348,055 B1 | 2/2002 | Preissman | |
| 6,371,968 B1 | 4/2002 | Kogasaka et al. | |
| 6,371,990 B1 | 4/2002 | Ferree | |

| Patent No. | Date | Name |
|---|---|---|
| 6,379,334 B1 | 4/2002 | Frassica |
| 6,383,188 B2 | 5/2002 | Kuslich et al. |
| 6,383,190 B1 | 5/2002 | Preissman |
| 6,387,130 B1 | 5/2002 | Stone et al. |
| 6,395,007 B1 | 5/2002 | Bhatnagar et al. |
| 6,395,034 B1 | 5/2002 | Suddaby |
| 6,402,750 B1 | 6/2002 | Atkinson et al. |
| 6,409,766 B1 | 6/2002 | Brett |
| 6,416,515 B1 | 7/2002 | Wagner |
| 6,419,677 B2 | 7/2002 | Zucherman et al. |
| 6,419,678 B1 | 7/2002 | Asfora |
| 6,423,095 B1 | 7/2002 | Van Hoeck et al. |
| 6,436,098 B1 | 8/2002 | Michelson |
| 6,436,102 B1 | 8/2002 | Ralph et al. |
| 6,436,140 B1 | 8/2002 | Liu et al. |
| 6,436,143 B1 | 8/2002 | Ross et al. |
| 6,440,138 B1 | 8/2002 | Reiley et al. |
| 6,447,514 B1 | 9/2002 | Stalcup et al. |
| 6,447,518 B1 | 9/2002 | Krause et al. |
| 6,447,546 B1 | 9/2002 | Bramlet et al. |
| 6,447,547 B1 | 9/2002 | Michelson |
| 6,464,713 B2 | 10/2002 | Bonutti |
| 6,468,277 B1 | 10/2002 | Justin et al. |
| 6,468,279 B1 | 10/2002 | Reo |
| 6,485,518 B1 | 11/2002 | Cornwall et al. |
| 6,517,541 B1 | 2/2003 | Sesic |
| 6,533,791 B1 | 3/2003 | Betz et al. |
| 6,540,747 B1 | 4/2003 | Marino |
| 6,558,386 B1 | 5/2003 | Cragg |
| 6,558,390 B2 | 5/2003 | Cragg |
| 6,562,046 B2 | 5/2003 | Sasso |
| 6,575,979 B1 | 6/2003 | Cragg |
| 6,607,530 B1 | 8/2003 | Carl et al. |
| 6,610,091 B1 | 8/2003 | Reiley |
| 6,652,535 B2 | 11/2003 | Kvarnstrom et al. |
| 6,669,699 B2 | 12/2003 | Ralph et al. |
| 6,692,495 B1 | 2/2004 | Zacouto |
| 6,740,090 B1 | 5/2004 | Cragg et al. |
| 6,764,489 B2 | 7/2004 | Ferree |
| 6,790,210 B1 | 9/2004 | Cragg et al. |
| 6,805,697 B1 | 10/2004 | Helm et al. |
| 6,875,215 B2 | 4/2005 | Taras et al. |
| 6,899,716 B2 | 5/2005 | Cragg |
| 6,921,403 B2 | 7/2005 | Cragg et al. |
| 6,991,653 B2 | 1/2006 | White et al. |
| 7,014,633 B2 | 3/2006 | Cragg |
| 7,033,394 B2 | 4/2006 | Michelson |
| 7,037,309 B2 | 5/2006 | Weil et al. |
| 7,087,056 B2 | 8/2006 | Vaughan |
| 7,087,058 B2 | 8/2006 | Cragg |
| 7,175,626 B2 | 2/2007 | Neff |
| 7,309,338 B2 | 12/2007 | Cragg |
| 7,329,259 B2 | 2/2008 | Cragg |
| 7,473,256 B2 | 1/2009 | Assell et al. |
| 7,491,236 B2 | 2/2009 | Cragg et al. |
| 7,500,977 B2 | 3/2009 | Assell et al. |
| 7,530,993 B2 | 5/2009 | Assell et al. |
| 7,547,317 B2 | 6/2009 | Cragg |
| 7,547,324 B2 | 6/2009 | Cragg et al. |
| 7,569,056 B2 | 8/2009 | Cragg et al. |
| 7,588,574 B2 | 9/2009 | Assell et al. |
| 7,601,171 B2 | 10/2009 | Ainsworth et al. |
| 7,608,077 B2 | 10/2009 | Cragg |
| 7,632,274 B2 | 12/2009 | Assell |
| 7,641,657 B2 | 1/2010 | Cragg |
| 7,662,173 B2 | 2/2010 | Cragg et al. |
| 7,727,263 B2 | 6/2010 | Cragg |
| 7,740,633 B2 | 6/2010 | Assell et al. |
| 7,744,599 B2 | 6/2010 | Cragg |
| 7,763,025 B2 | 7/2010 | Assell et al. |
| 7,794,463 B2 | 9/2010 | Cragg |
| 7,799,032 B2 | 9/2010 | Assell et al. |
| 7,799,033 B2 | 9/2010 | Assell et al. |
| 7,914,535 B2 | 3/2011 | Assell et al. |
| 8,034,055 B2 | 10/2011 | Cragg |
| 8,052,613 B2 | 11/2011 | Assell et al. |
| 8,105,365 B2 | 1/2012 | Cragg |
| 2002/0022888 A1 | 2/2002 | Serhan et al. |
| 2002/0032444 A1 | 3/2002 | Mische |
| 2002/0038123 A1 | 3/2002 | Visotsky et al. |
| 2002/0052608 A1 | 5/2002 | Kvarnstrom et al. |
| 2002/0068939 A1 | 6/2002 | Levy et al. |
| 2002/0072801 A1 | 6/2002 | Michelson |
| 2002/0077632 A1 | 6/2002 | Tsou |
| 2002/0077700 A1 | 6/2002 | Varga et al. |
| 2002/0077702 A1 | 6/2002 | Castro |
| 2002/0082598 A1 | 6/2002 | Teitelbaum |
| 2002/0087163 A1 | 7/2002 | Dixon et al. |
| 2002/0107573 A1 | 8/2002 | Steinberg |
| 2002/0110439 A1 | 8/2002 | Craven |
| 2002/0147485 A1 | 10/2002 | Mamo et al. |
| 2003/0028193 A1 | 2/2003 | Weil et al. |
| 2003/0045881 A1 | 3/2003 | Barouk et al. |
| 2003/0065394 A1 | 4/2003 | Michelson |
| 2003/0158556 A1 | 8/2003 | Taras et al. |
| 2003/0176926 A1 | 9/2003 | Boehm et al. |
| 2003/0181982 A1 | 9/2003 | Kuslich |
| 2003/0191474 A1 | 10/2003 | Cragg et al. |
| 2003/0204189 A1 | 10/2003 | Cragg |
| 2003/0212400 A1 | 11/2003 | Bloemer et al. |
| 2004/0138752 A1 | 7/2004 | Michelson |
| 2004/0141827 A1 | 7/2004 | Dicke |
| 2004/0151559 A1 | 8/2004 | Craven |
| 2004/0193155 A1 | 9/2004 | Castaneda |
| 2004/0230195 A1 | 11/2004 | Kaikkonen et al. |
| 2005/0038438 A1 | 2/2005 | Anderson et al. |
| 2005/0101961 A1 | 5/2005 | Huebner et al. |
| 2005/0107791 A1 | 5/2005 | Manderson |
| 2005/0113919 A1 | 5/2005 | Cragg et al. |
| 2005/0137601 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0149049 A1 | 7/2005 | Assell et al. |
| 2005/0149191 A1 | 7/2005 | Cragg et al. |
| 2005/0261695 A1 | 11/2005 | Cragg et al. |
| 2006/0058800 A1 | 3/2006 | Ainsworth et al. |
| 2006/0155297 A1 | 7/2006 | Ainsworth et al. |
| 2006/0206208 A1 | 9/2006 | Michelson |
| 2006/0206209 A1 | 9/2006 | Cragg et al. |
| 2006/0229622 A1 | 10/2006 | Huebner et al. |
| 2006/0264957 A1 | 11/2006 | Cragg et al. |
| 2007/0010819 A1 | 1/2007 | Johnstone |
| 2007/0055260 A1 | 3/2007 | Cragg |
| 2007/0066977 A1 | 3/2007 | Assell et al. |
| 2007/0112351 A1 | 5/2007 | Assell et al. |
| 2007/0118132 A1 | 5/2007 | Culbert et al. |
| 2007/0167951 A1 | 7/2007 | Ainsworth et al. |
| 2007/0168036 A1 | 7/2007 | Ainsworth et al. |
| 2007/0233099 A1 | 10/2007 | Cragg |
| 2007/0233260 A1 | 10/2007 | Cragg |
| 2007/0260270 A1 | 11/2007 | Assell et al. |
| 2008/0004707 A1 | 1/2008 | Cragg |
| 2008/0033466 A1 | 2/2008 | Assell et al. |
| 2008/0065076 A1 | 3/2008 | Cragg |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0071278 A1 | 3/2008 | Assell et al. |
| 2008/0071282 A1 | 3/2008 | Assell et al. |
| 2008/0091199 A1 | 4/2008 | Cragg |
| 2008/0097452 A1 | 4/2008 | Assell et al. |
| 2008/0154275 A1 | 6/2008 | Assell et al. |
| 2008/0188895 A1 | 8/2008 | Cragg |
| 2008/0195156 A1 | 8/2008 | Ainsworth et al. |
| 2008/0262502 A1 | 10/2008 | Ainsworth et al. |
| 2008/0262555 A1 | 10/2008 | Assell |
| 2009/0105768 A1 | 4/2009 | Cragg et al. |
| 2009/0240293 A1 | 9/2009 | Cragg |
| 2009/0270902 A1 | 10/2009 | Assell et al. |
| 2009/0292287 A1 | 11/2009 | Cragg et al. |
| 2010/0137991 A1 | 6/2010 | Ainsworth |
| 2010/0145462 A1 | 6/2010 | Ainsworth |
| 2011/0040329 A1 | 2/2011 | Ainsworth |
| 2011/0082424 A1 | 4/2011 | Barnhouse |
| 2011/0184420 A1 | 7/2011 | Barnhouse |

FOREIGN PATENT DOCUMENTS

| | | |
|---|---|---|
| EP | 0 980 677 A1 | 2/2000 |
| EP | 1 029 519 | 8/2000 |
| WO | WO 95/22285 | 8/1995 |
| WO | WO 96/28118 | 9/1996 |
| WO | WO 97/40878 | 11/1997 |
| WO | WO 98/38918 | 9/1998 |
| WO | WO 99/47055 | 9/1999 |
| WO | WO 00/67650 | 11/2000 |
| WO | WO 01/28468 A1 | 4/2001 |
| WO | WO 01/60268 A1 | 8/2001 |
| WO | WO 02/09801 A1 | 2/2002 |
| WO | WO 02/13732 A2 | 2/2002 |
| WO | WO 02/17825 A2 | 3/2002 |
| WO | WO 02/34120 A2 | 5/2002 |
| WO | WO 02/058599 A2 | 8/2002 |
| WO | WO 02/071921 A2 | 9/2002 |

OTHER PUBLICATIONS

Curtis A. Dickman, M.D., et al., "Transpedicular screw-rod fixation of the lumbar spine: operative technique and outcome in 104 cases," J. Neurosurg, Dec. 1992, vol. 77, pp. 860-870.

Friedrich W. Rathke and Karl F. Schlegel, Surgery of the Spine, Atlas of Orthopaedic Operations, vol. 1, 1979, pp. 222-224.

Hallett H. Mathews, M.D., "Minimally Invasive Fusion Techniques, Percutaneous Interbody Fusions," Orthopedic Clinics of North America, Oct. 1998, vol. 29, No. 4.

Hallett H. Mathews, M.D., et al., "Perspectives on Modern Orthopaedics, Minimally Invasive Techniques for the Treatment of Intervertebral Disk Herniation," Journal of the American Academy of Orthopaedic Surgeons, Mar./Apr. 2002, vol. 10, No. 2.

J. Dove, FRCS, "The Hartshill System for the Front of the Lumbosacral Spine," Lumbosacral and Spinopelvic Fusion, Chapter 42 (pp. 539-543) Lippincott-Raven Publishers (1996).

J.J. Trambert, M.D., "Percutaneous Interventions in the Presacral Space: CT-guided Precoccygeal Approach—Early Experience," (Radiology 1999; 213:901-904).

J.W. Olgilvie, M.D., et al., "Overview of Fixation to the Sacrum & Pelvis in Spinal Surgery," Lumbosacral and Spinopelvic Fusion, Chapter 17 (pp. 191-198) Lippincott-Raven Publishers (1996).

Jason A. Smith, MD, et al., "Clinical Outcome of Trans-Sacral Interbody Fusion After Partial Reduction for High-Grade L5-S1 Spondylolisthesis," Spine, 2001, vol. 26, No. 20, pp. 2227-2234.

John L. Emmett, M.D., M.S. (Urology), David M. Witten, M.D., M.S. (Radiology)—vol. 1, Third Edition—Clinical Urography—An Atlas and Textbook of Roentgenologic Diagnosis—1971—Phneumography (Retroperitoneal Gas [Air] Insufflation; Perirenal Insufflation; Presacral Insufflation).

M.R. Zindrick, M.D., et al., "Clinical Anatomy of the Lumbosacral Junction and Pelvix," Lumbosacral and Spinopelvic Fusion, Chapter 2 (pp. 13-25) Lippincott-Raven Publishers (1996).

Michael MacMillan, et al., Biomechanical Analysis of a New Anterior Spine Implant for Post-Corpectomy Instability, Journal of Spinal Disorders, 1995, vol. 8, No. 1, pp. 56-61.

Michael MacMillan, MD, et al., "Percutaneous Lumbosacral Fixation and Fusion," Percutaneous Spine Techniques, Jan. 1996, vol. 7, No. 1, pp. 99-106.

P. Kambin, M.D., et al., "Arthroscopic fusion of the Lumbosacral Spine," Lumbosacral and Spinopelvic Fusion, Chapter 44 (pp. 565-577) Lippincott-Raven Publishers (1996).

Parviz Kambin, M.D., "Percutaneous Spine Techniques, Diagnostic and Therapeutic Spinal Arthroscopy," Neurosurgery Clinics of North America, Jan. 1996, vol. 7, No. 1.

Parviz Kambin, M.D., et al., "Arthroscopic Discectomy of the Lumbar Spine," Clinical Orthopaedics and Related Research, Apr. 1997, No. 337.

Parviz Kambin, M.D., et al., "Arthroscopic Microdiscectomy: An Alternative to Open Disc Surgery," The Mount Sinai Journal of Medicine, Sep. 2000, vol. 67, No. 4.

R. Johnsson, et al., "Posterolateral Lumbar Fusion Using Facet Joint Fixation With Biodegradable Rods: A Pilot Study," Eur Spine J., (1997) 6:144-148.

R.P. Louis, M.D., "Anatomy, Physiology, and Biomechanics of the Lumbopelvic Junction," Lumbosacral and Spinopelvic Fusion, Chapter 1 (pp. 1-11) Lippincott-Raven Publishers (1996).

R.P. Louis, M.D., "Lumbopelvic Fusion," Lumbosacral and Spinopelvic Fusion, Chapter 38, (pp. 479-492) Lippincott-Raven Publishers (1996).

Richard M. Slone, MD, et al., "Spinal Fixation, Part 1, Basic Hardware, and Fixation Techniques for the Cervical Spine," RadioGraphics, 1993, vol. 13, No. 2, pp. 341-356.

Richard M. Slone, MD, et al., "Spinal Fixation, Part 2, Fixation Techniques and Hardware for the Thoracic and Lumbosacral Spine," RadioGraphics, 1993, vol. 13, No. 3, pp. 521-543.

S.A. Caruso, M.E., et al., "Instrumented Fusions of the Lumbosacral Spine: A Technical Overview," Lumbosacral and Spinopelvic Fusion, Chapter 18 (pp. 199-210) Lippincott-Raven Publishers (1996).

Japanese Unexamined Patent Publication 11-502437 published on Mar. 2, 1999 to Kuslich in 26 pages.

Translation of Japanese Office Action mailed Jul. 14, 2010 in Japanese Patent App. No. 2001-559335 in 5 pages.

* cited by examiner

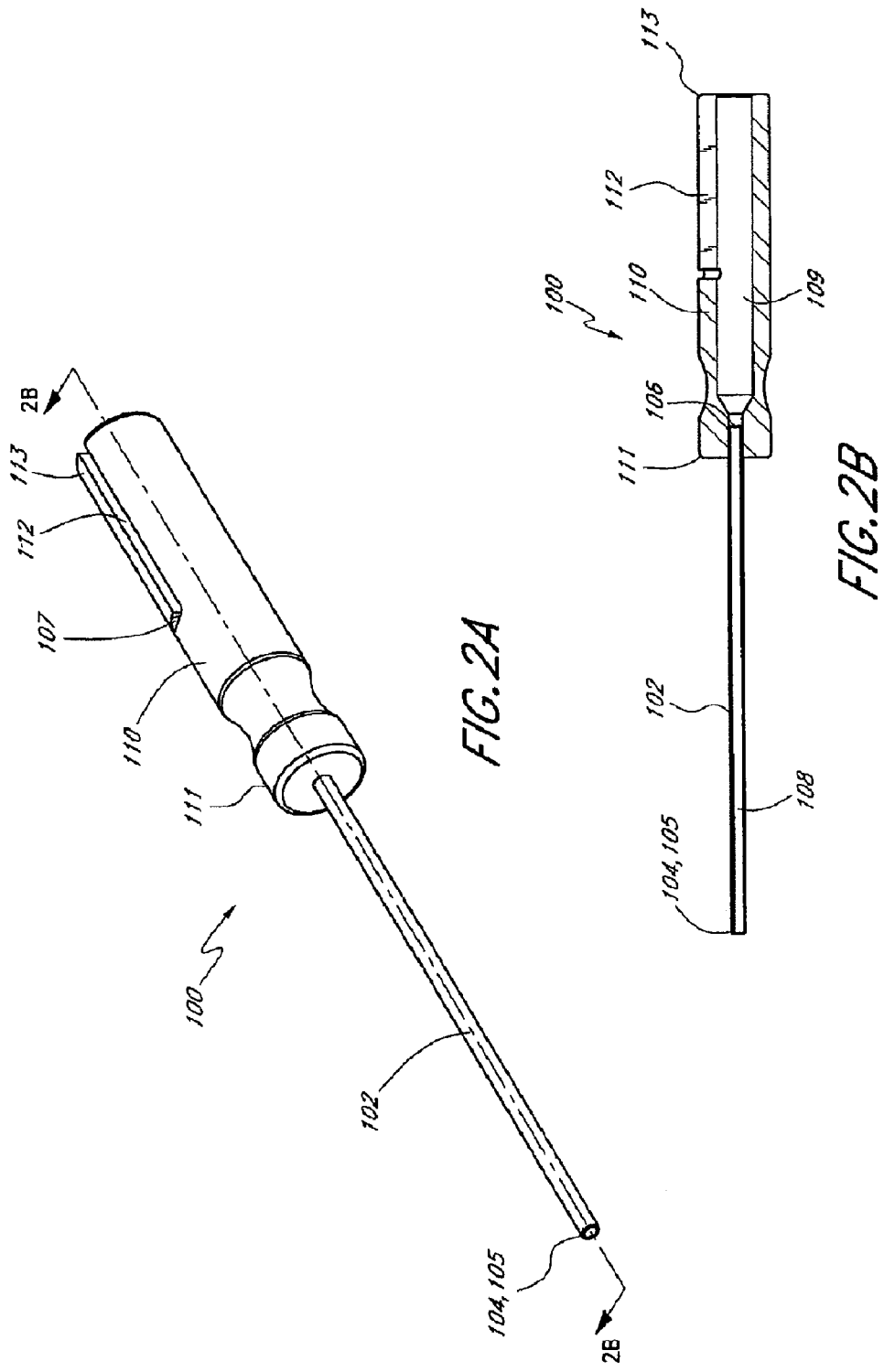

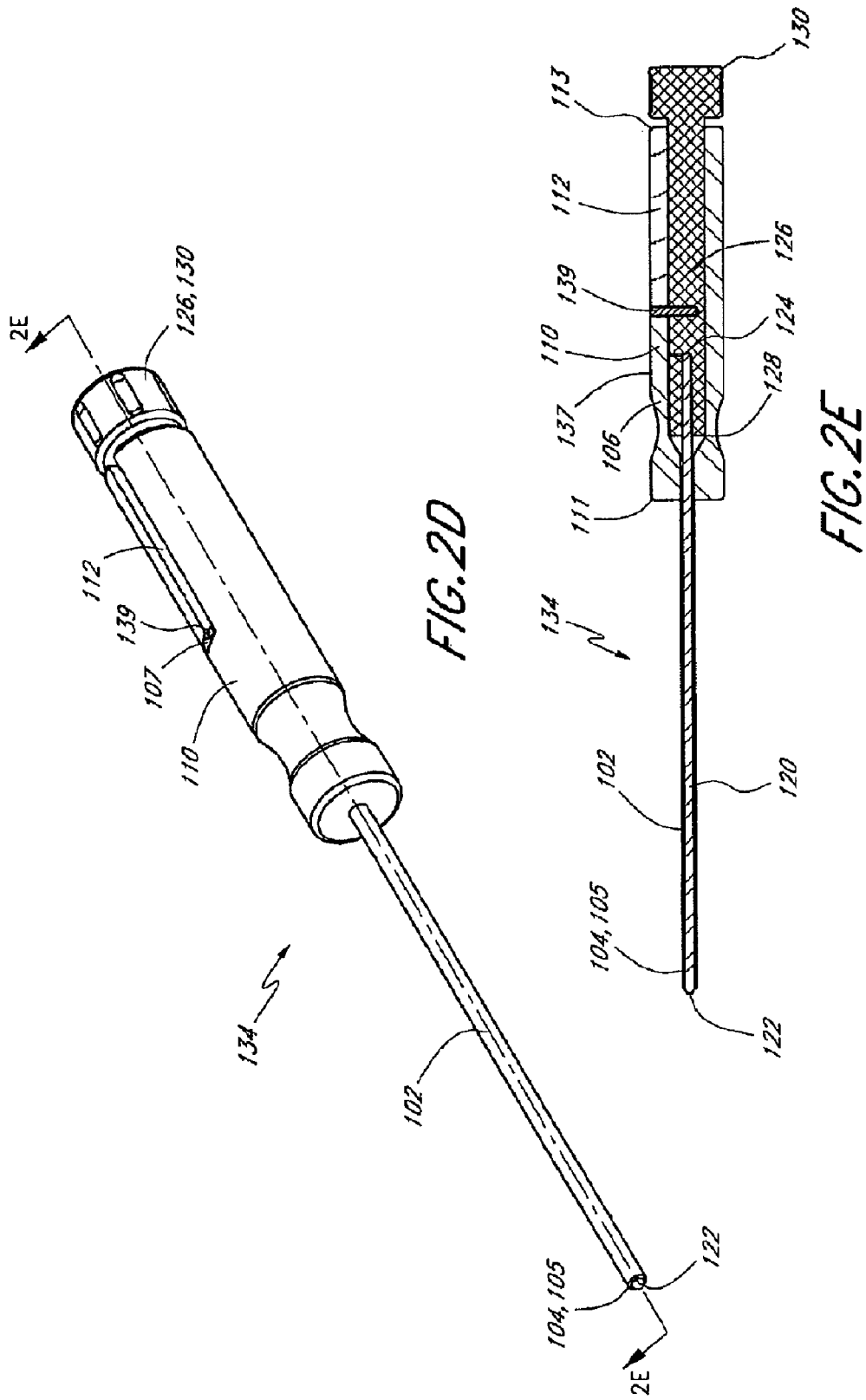

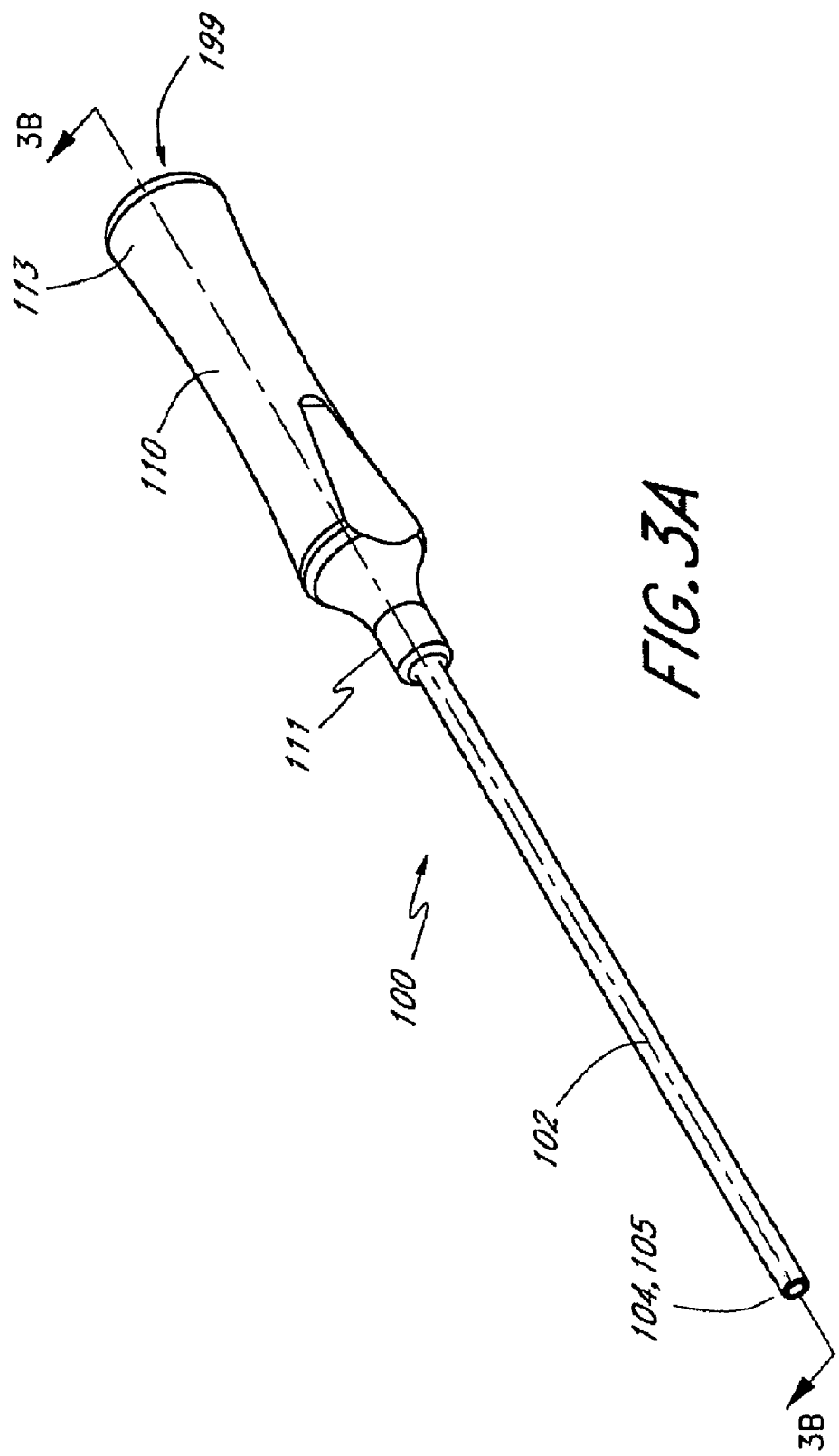

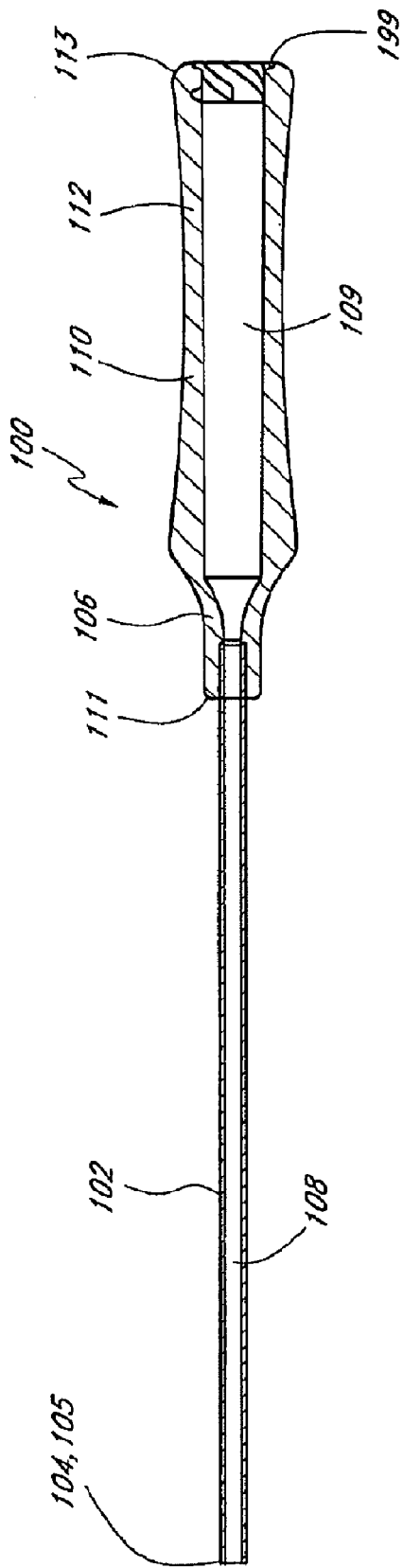

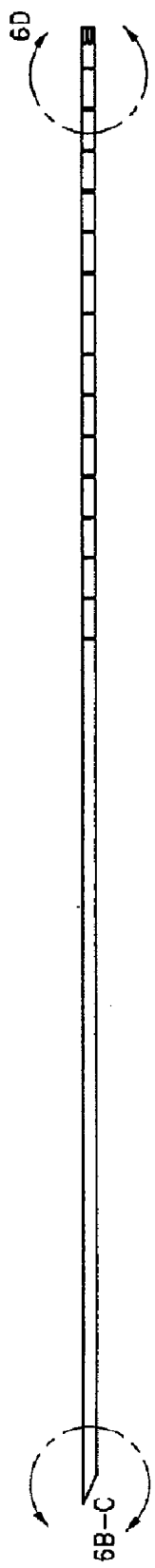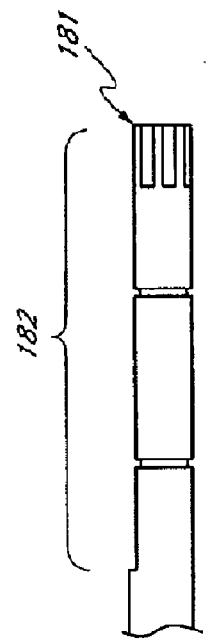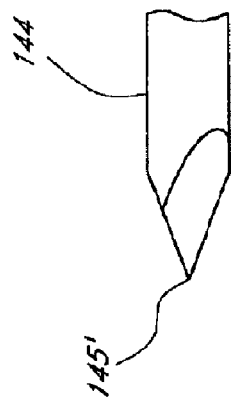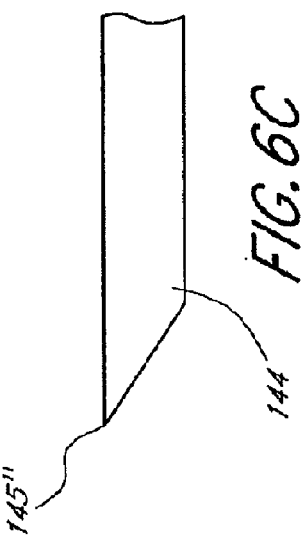
FIG.6A
FIG.6B
FIG.6C
FIG.6D

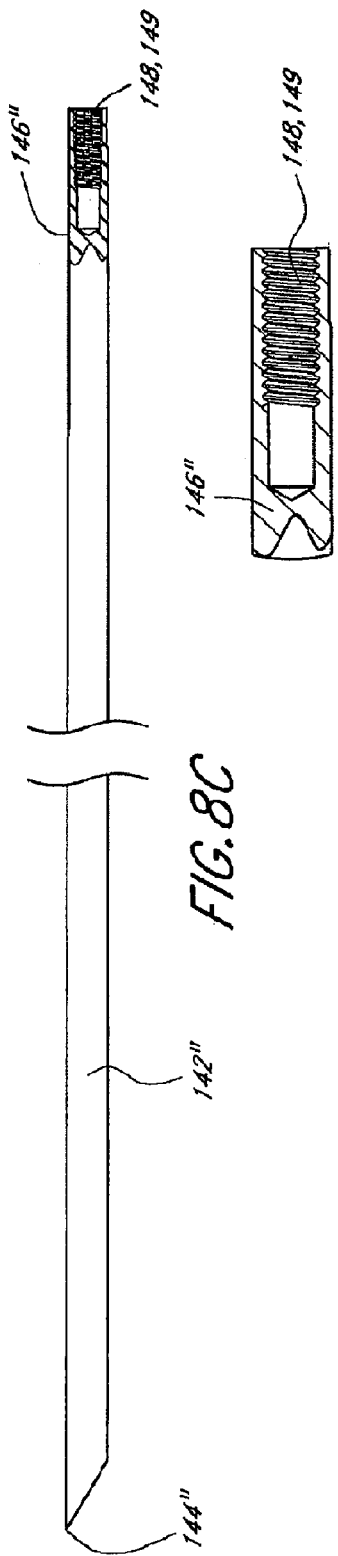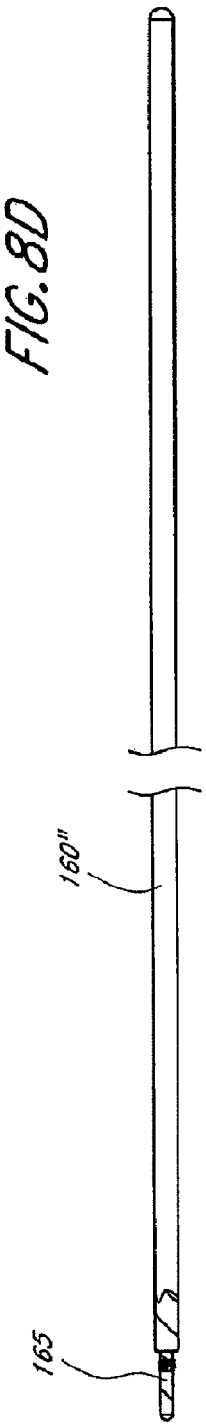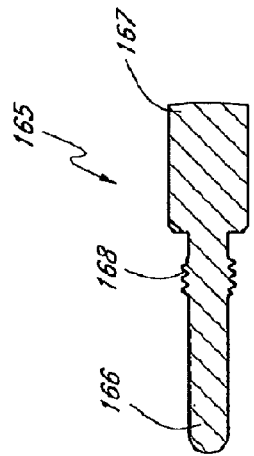

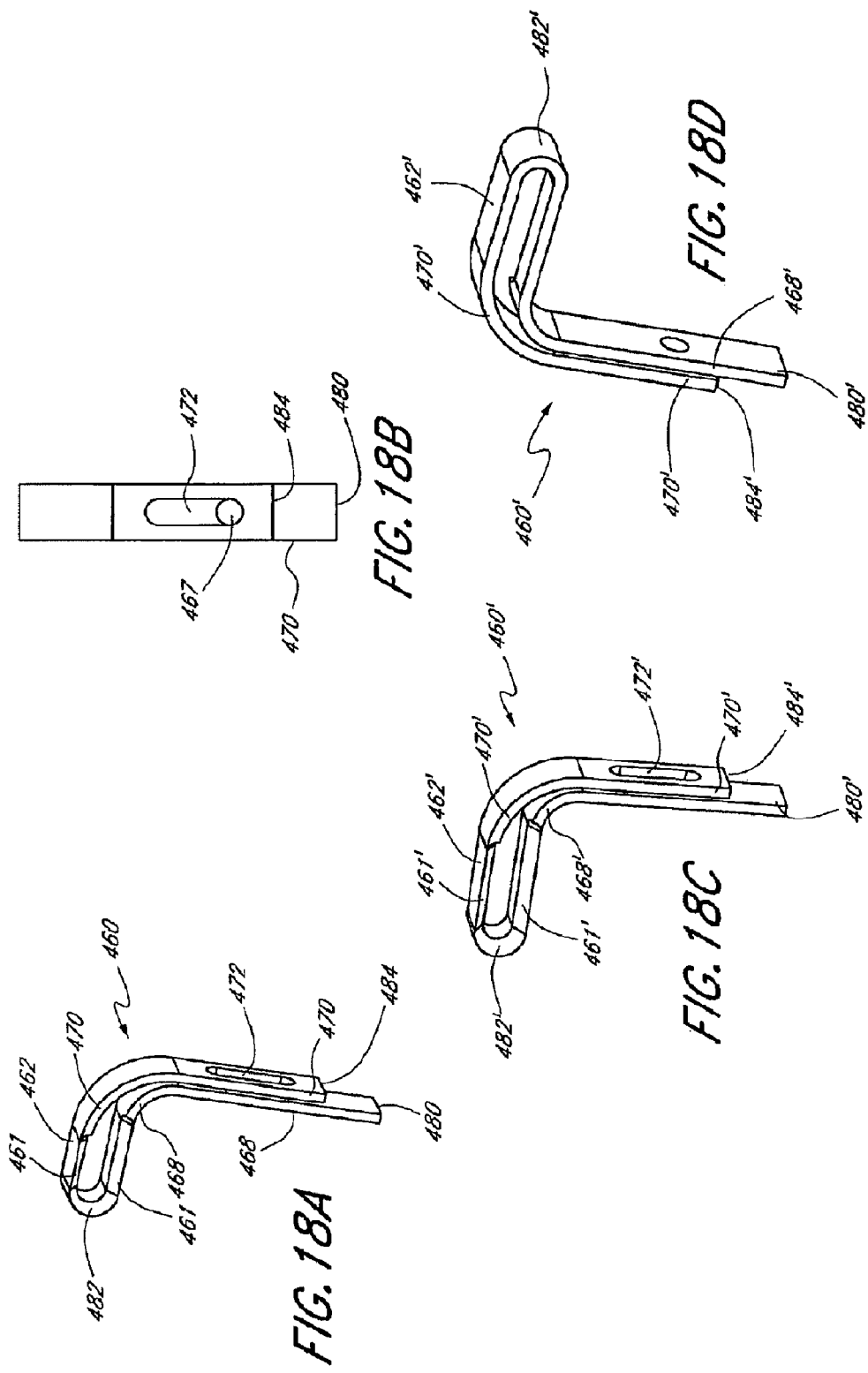

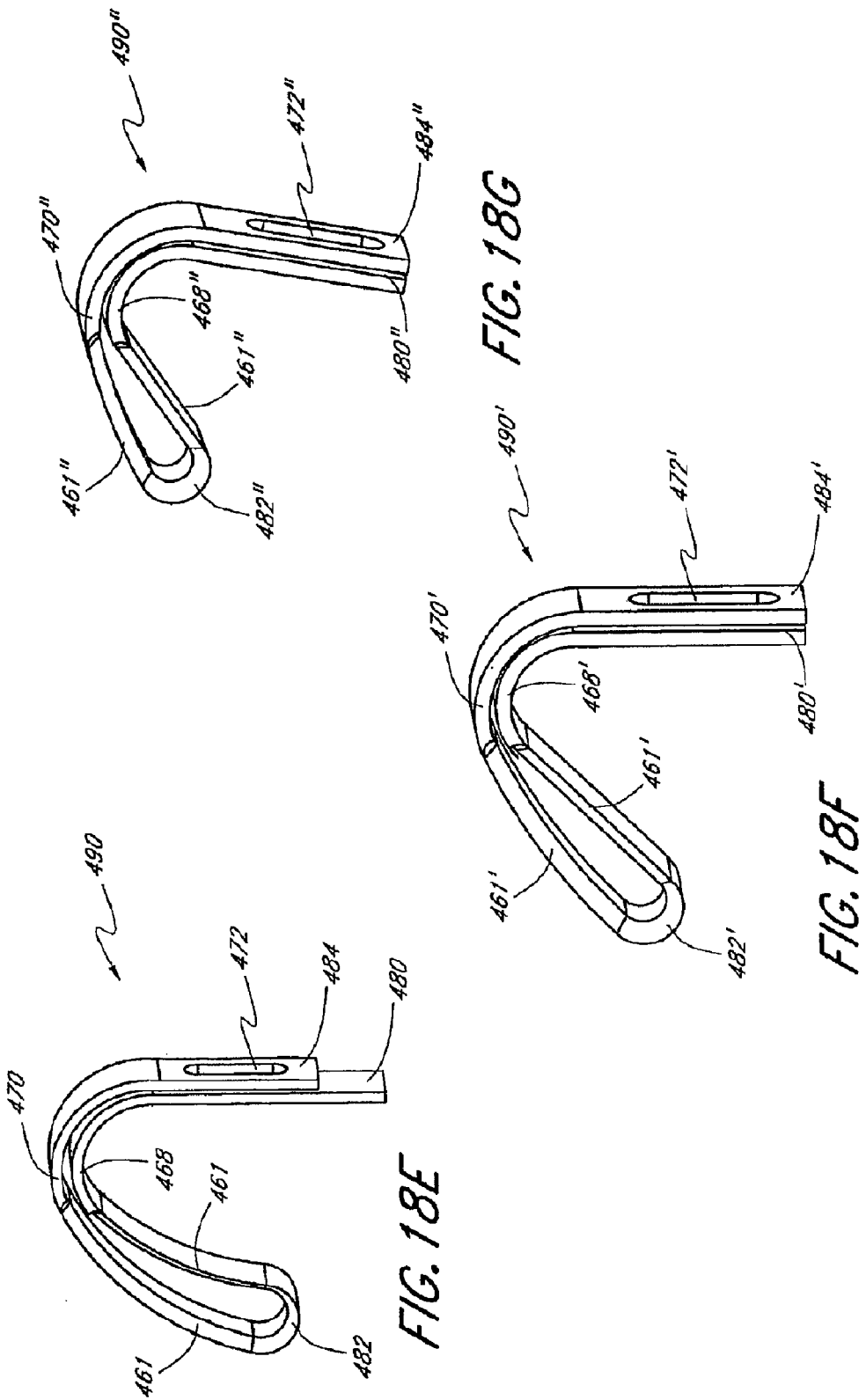

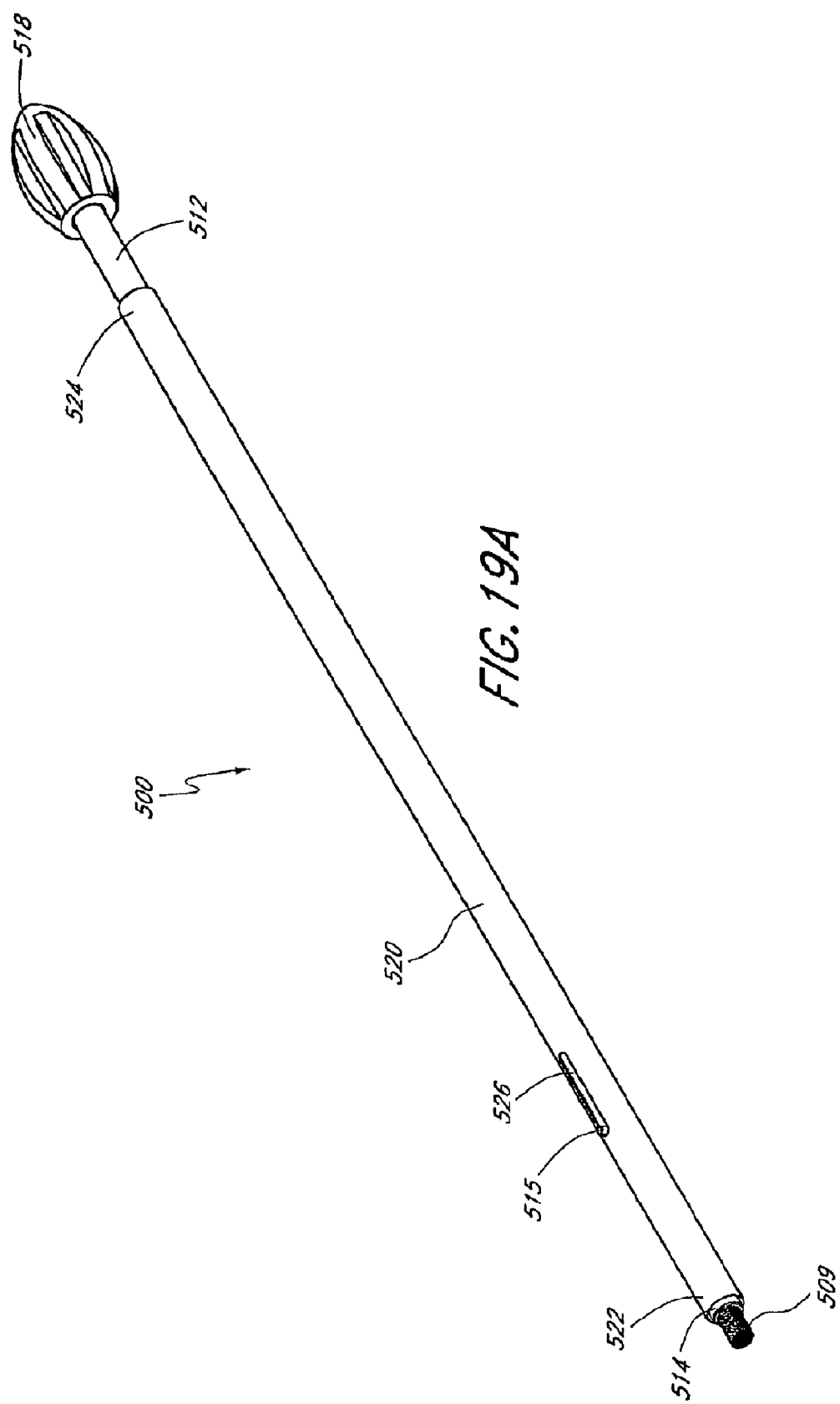

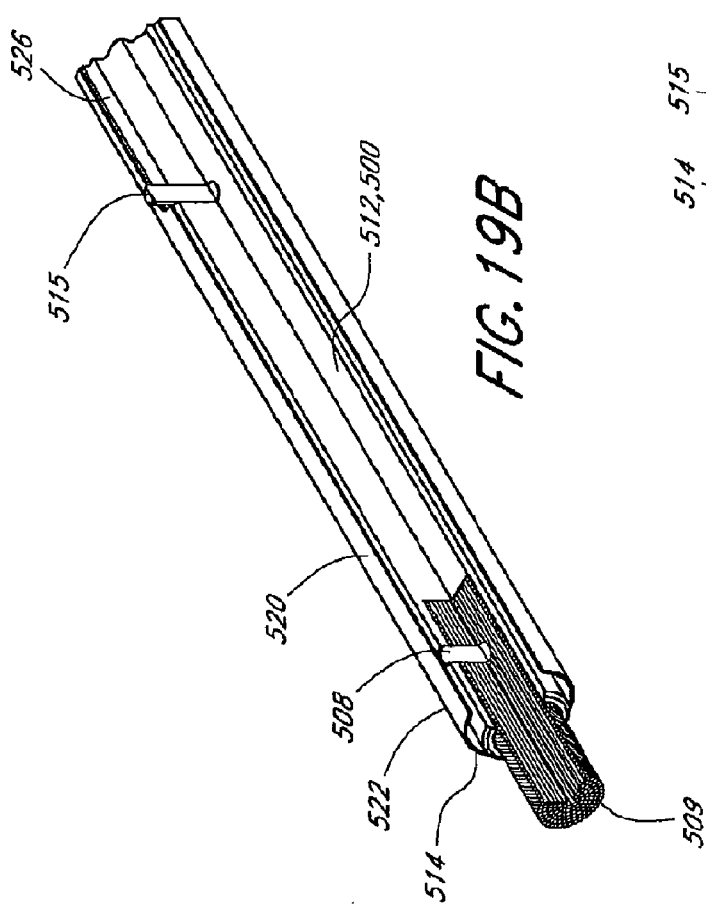
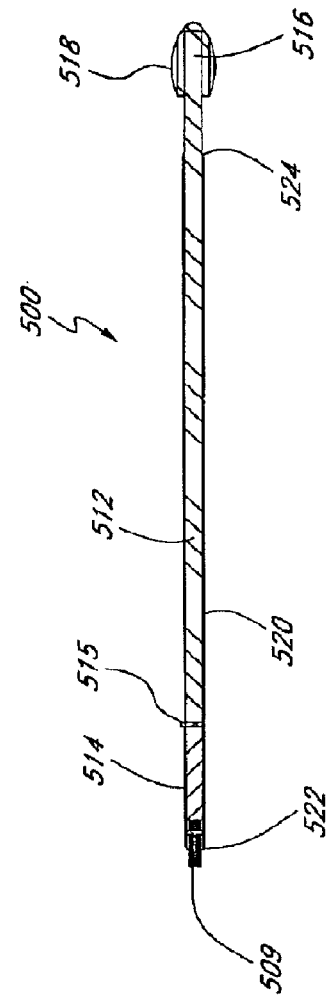
FIG. 19B
FIG. 19C

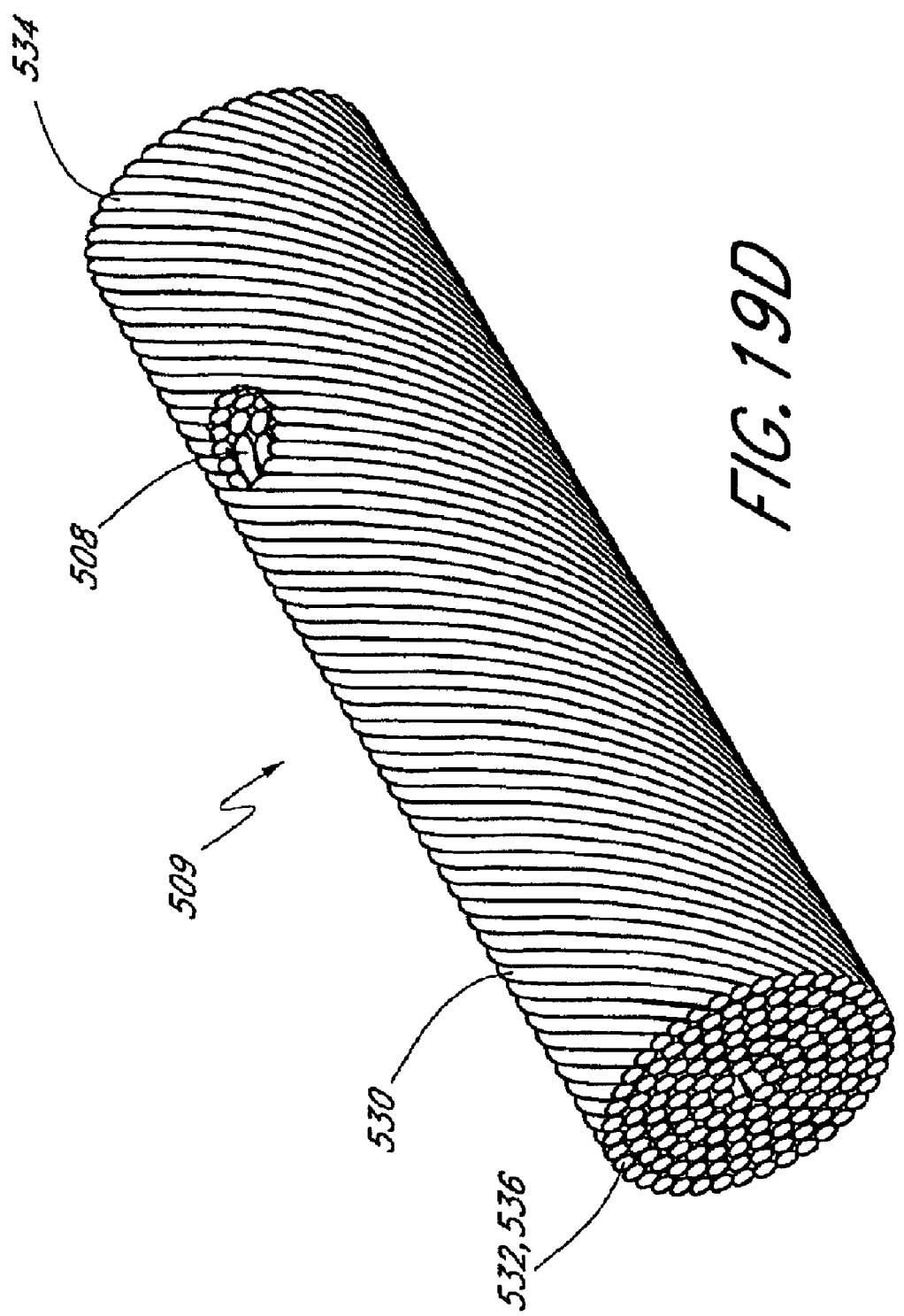

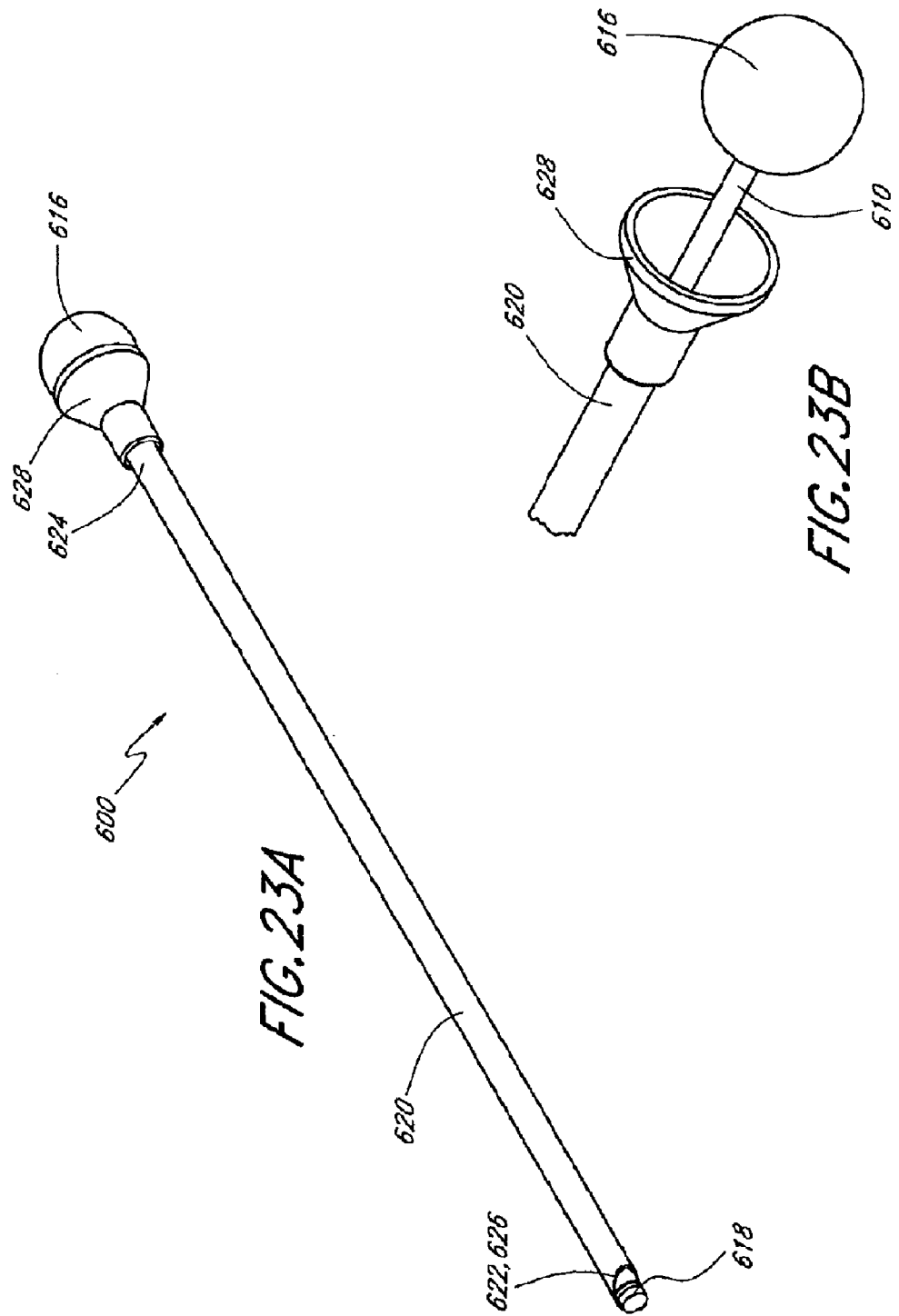

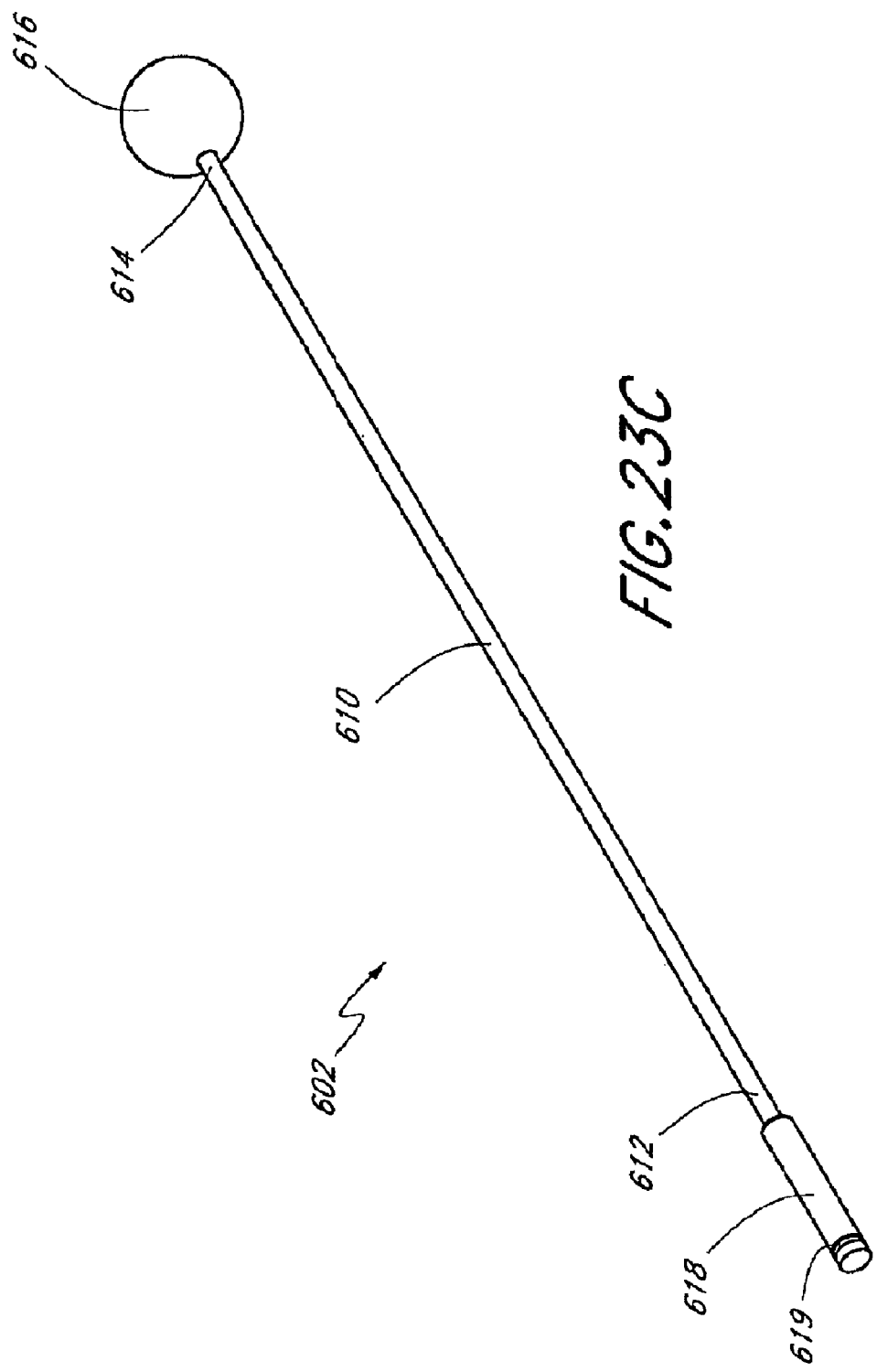

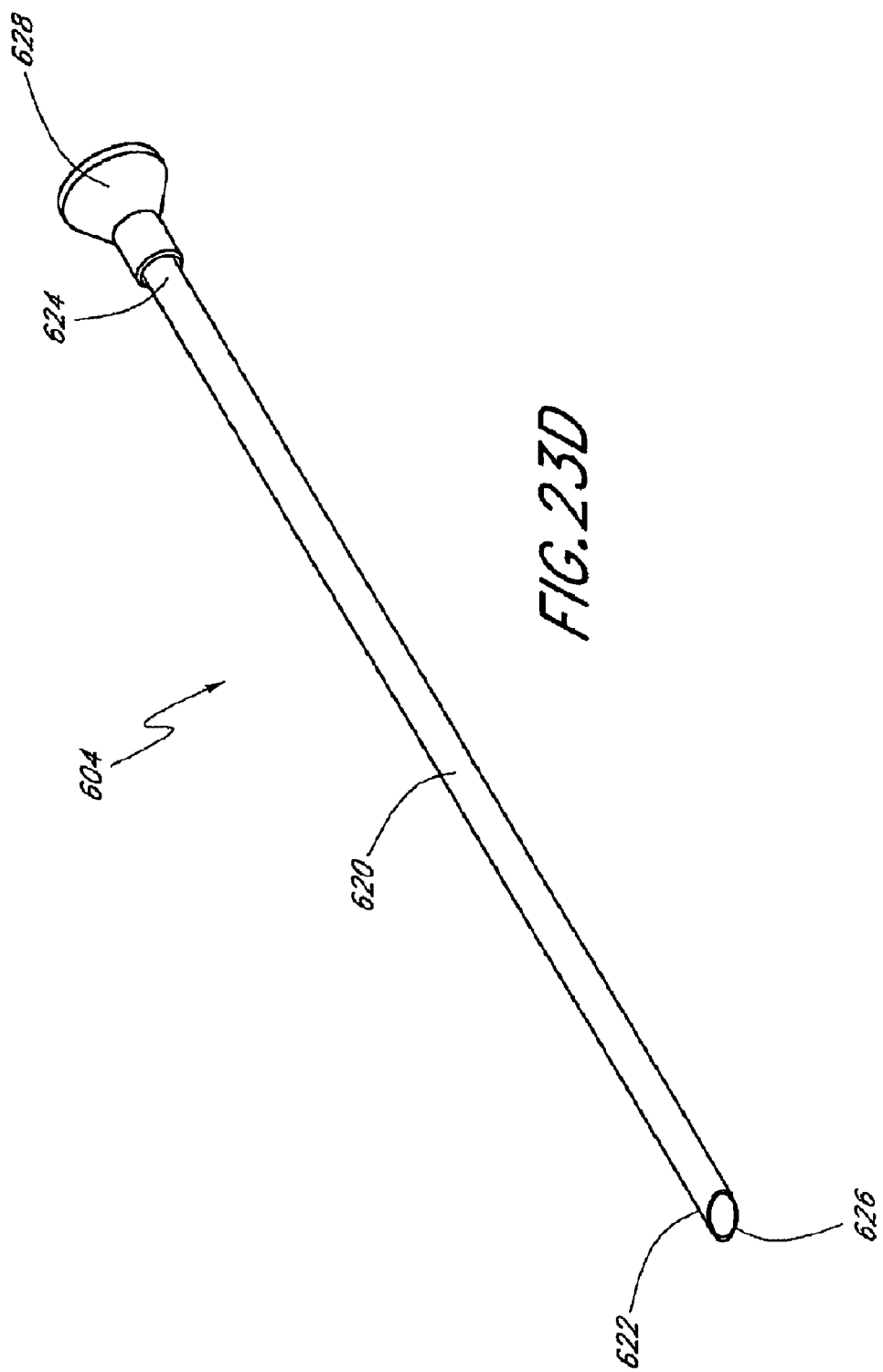

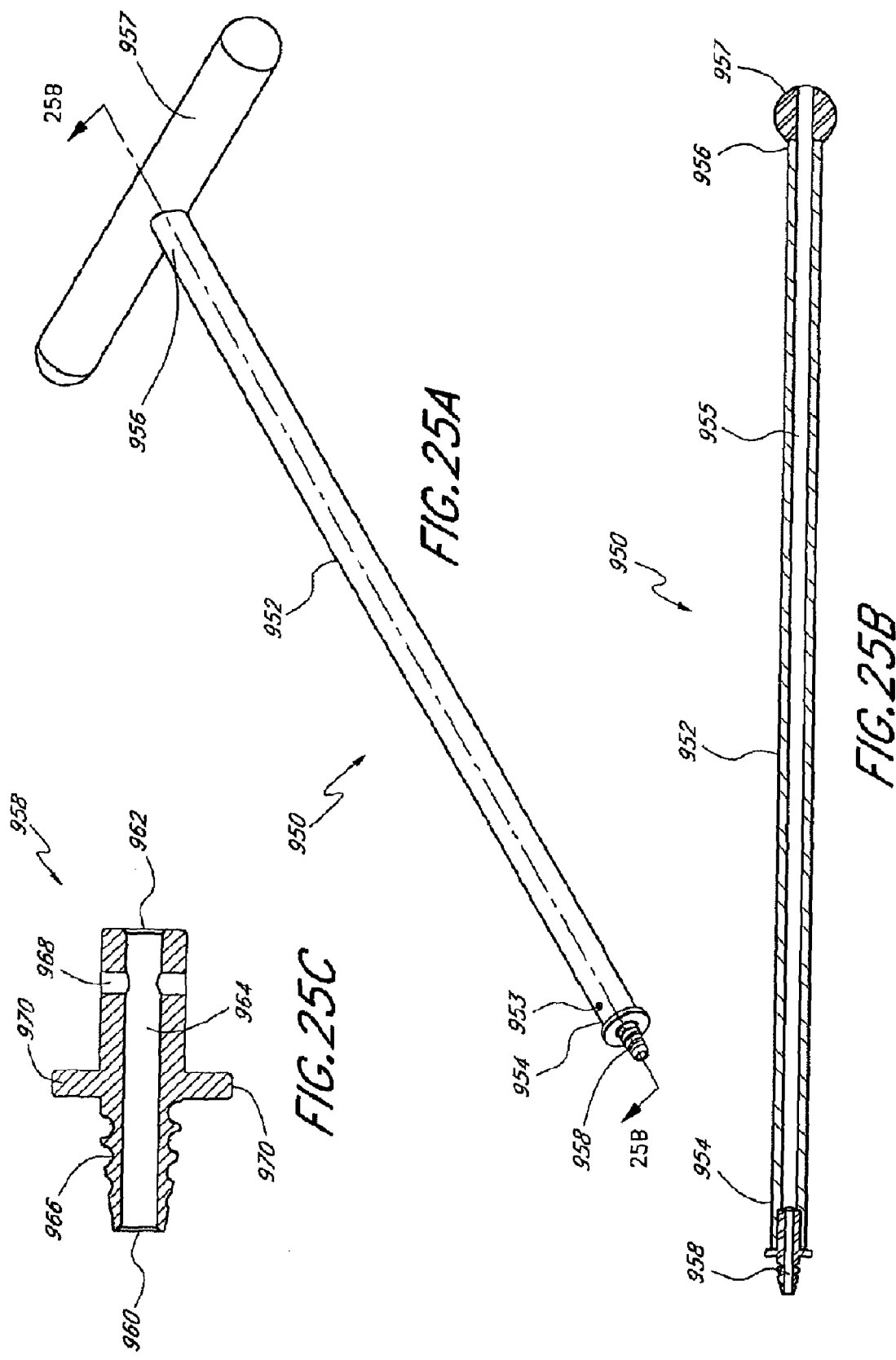

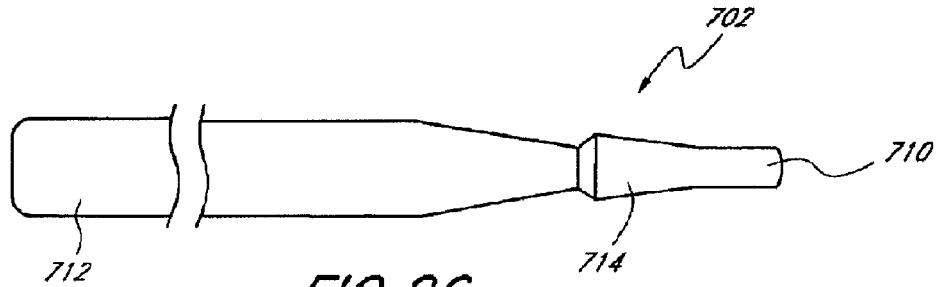
FIG.26
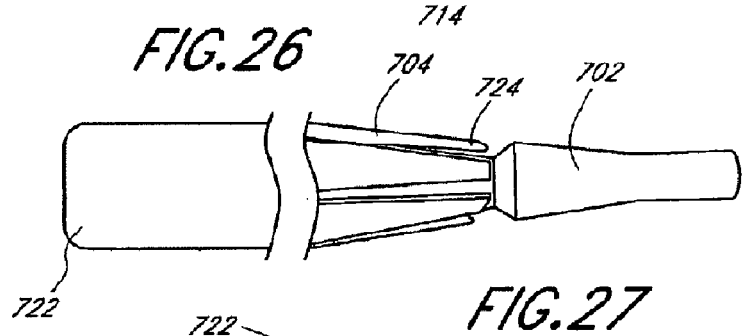
FIG.27
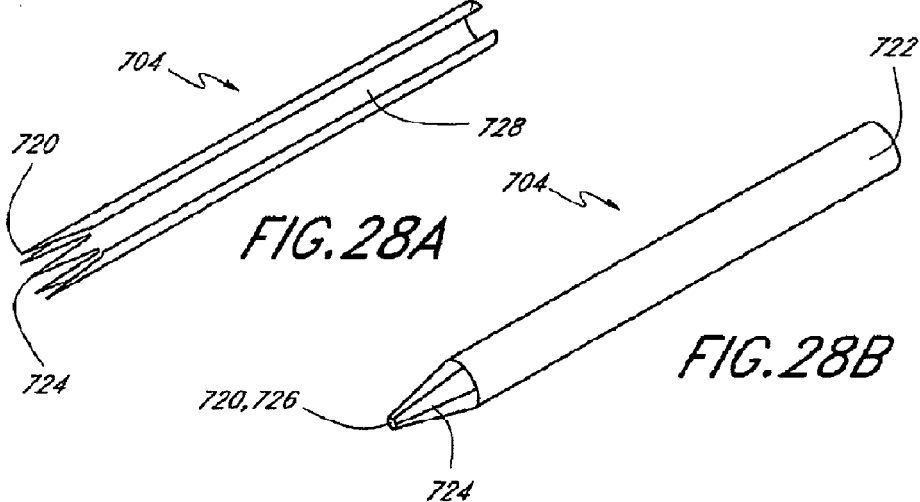
FIG.28A
FIG.28B
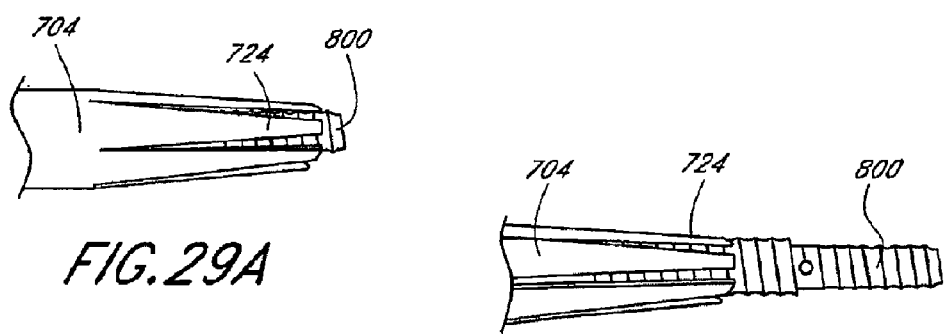
FIG.29A
FIG.29B

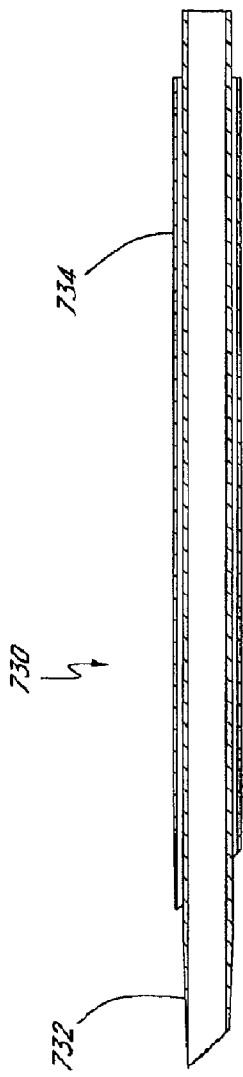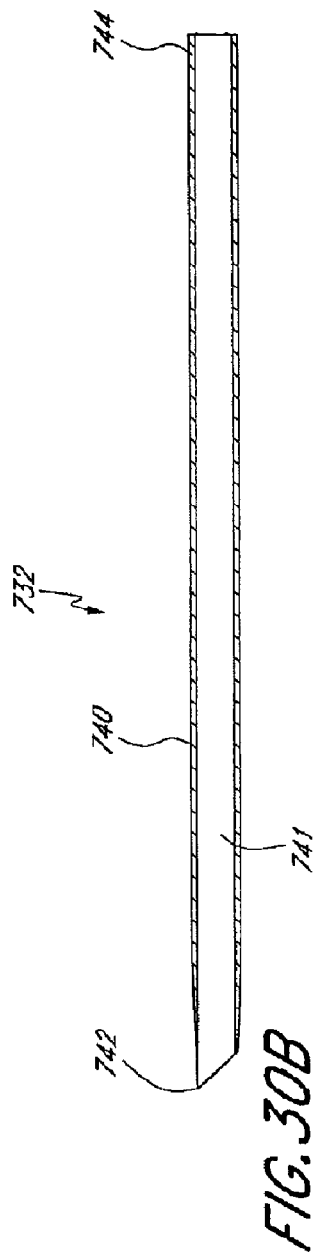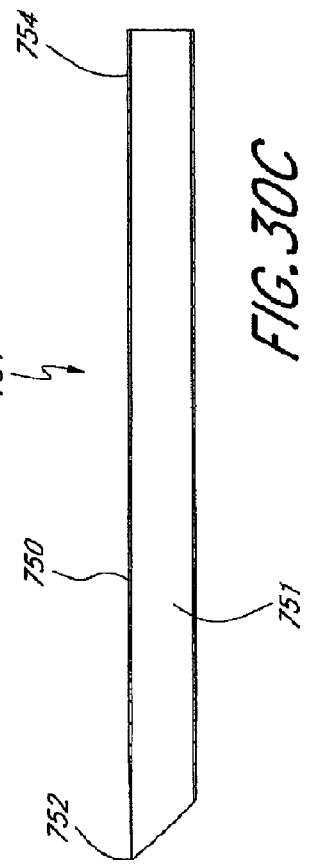

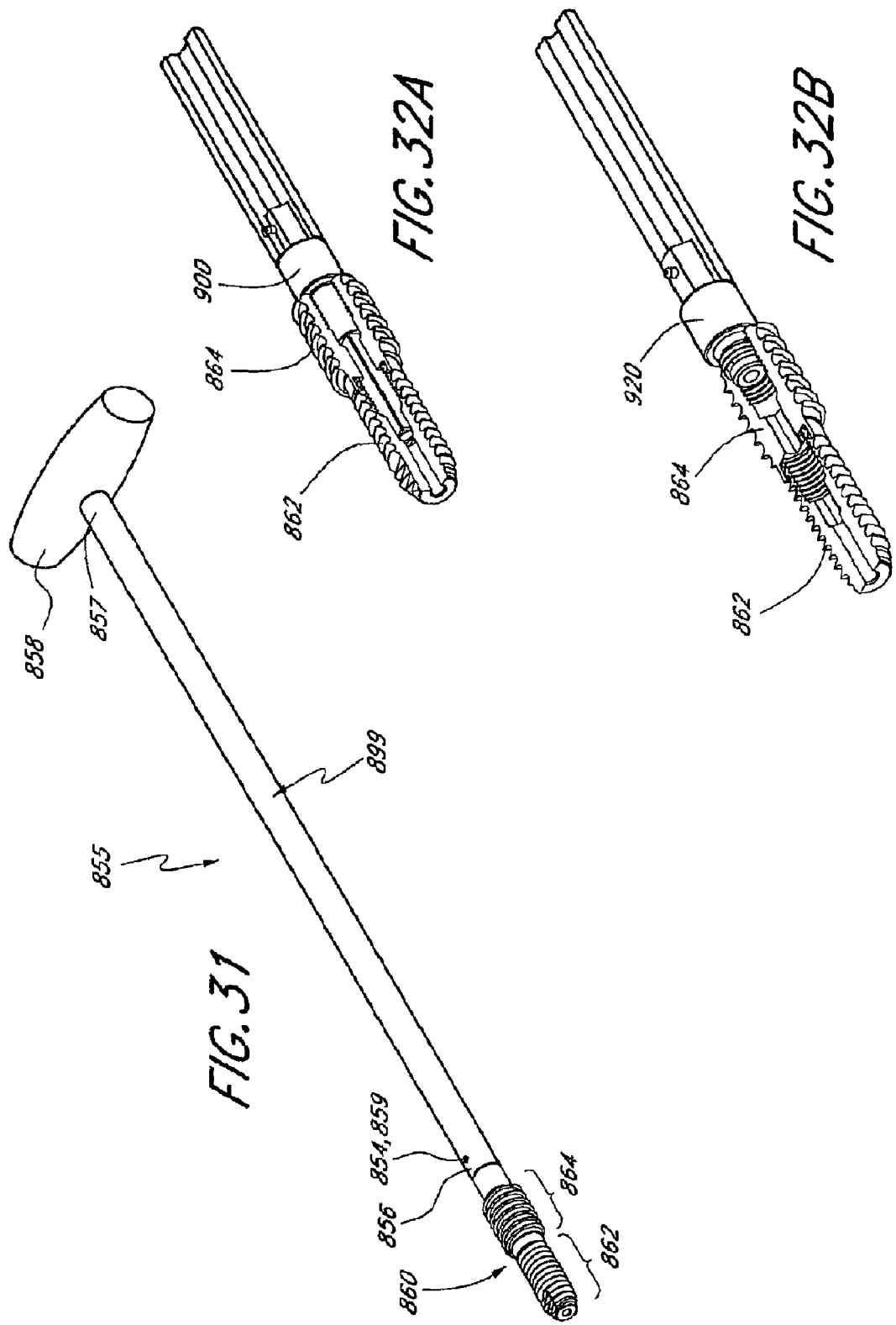

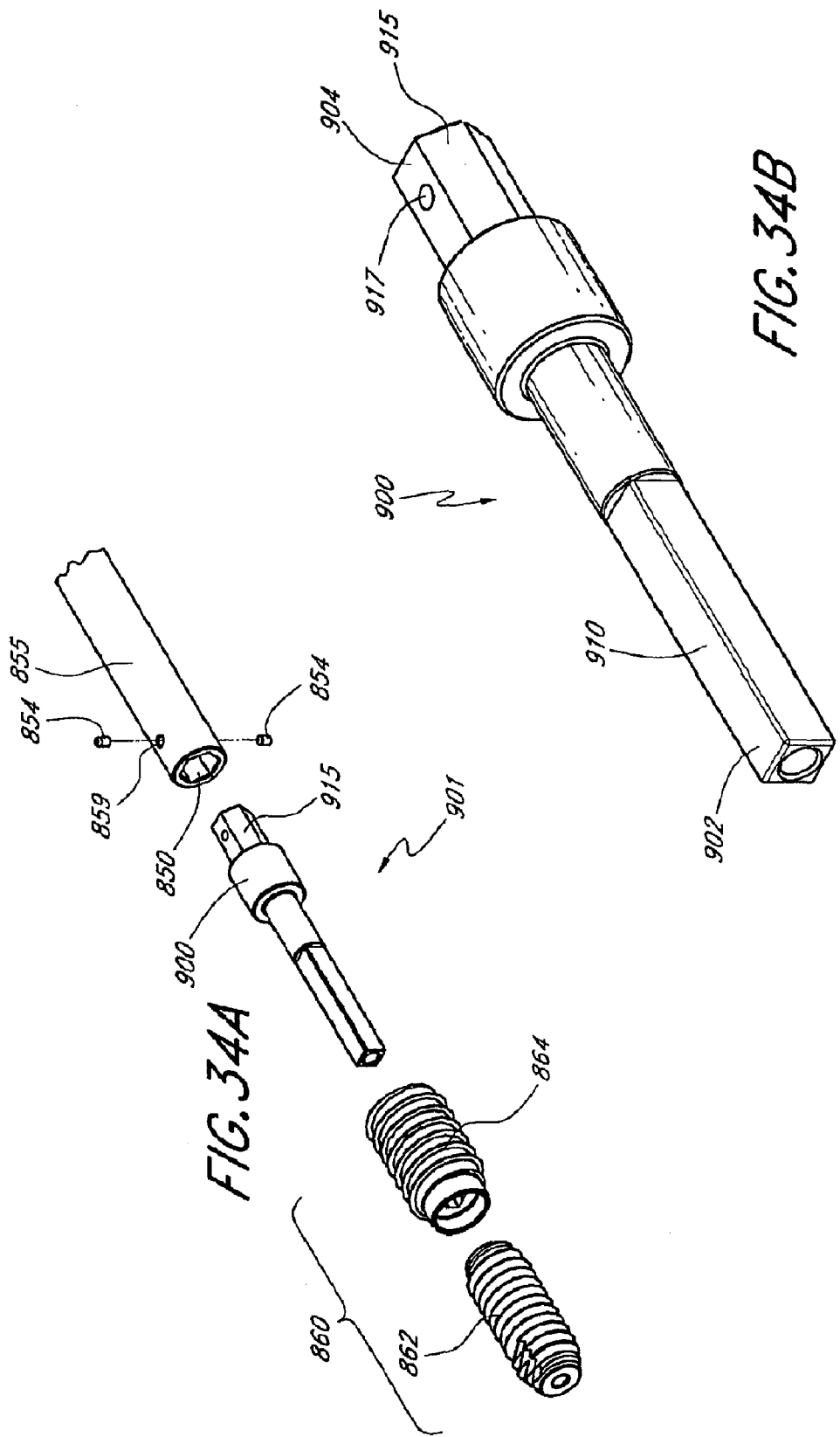

METHOD AND APPARATUS FOR REMOVABLE SPINAL IMPLANT EXTENDING BETWEEN AT LEAST TWO ADJACENT VERTEBRAL BODIES

RELATED APPLICATIONS

This U.S. patent application is a continuation of U.S. patent application Ser. No. 12/367,397 filed on Feb. 6, 2009, which is a continuation of U.S. patent application Ser. No. 10/972,077 filed on Oct. 22, 2004, which issued as U.S. Pat. No. 7,500,977 on Mar. 10, 2009, which claims priority and benefits from U.S. Provisional Patent Application No. 60/513,899, filed on Oct. 23, 2003. The contents of each of the aforementioned U.S. patent applications are hereby incorporated in their entirety into this disclosure by reference.

BACKGROUND OF THE INVENTION

1. Field of the Invention

The present invention relates generally to instrumentation systems and methods for accessing and preparing treatment sites within the spine (e.g., inter-vertebral motion segments) for subsequent therapeutic procedures, such as, for example, spinal arthroplasty, partial or total disc replacement, annulus repair, vertebroplasty, arthrodesis (fusion), or the like. Disclosed herein are various tools and methods of use (e.g., surgical cutting devices, tissue extractors, etc.) for performing any number of minimally-invasive treatment procedures (e.g., low trauma disc nucleectomy via trans-sacral axial access). The methods can involve, among other things, facilitating the removal of resulting tissue fragments, preparing an intervertebral disc space for subsequent deployment of spinal fusion designed to relieve lower back pain, or motion preservation devices, e.g., dynamic stabilization, devices, prosthetic nucleus devices and total disc replacements designed to relieve lower back pain and to restore physiological function of the lumbar spine, maintain and possibly improve disc health and prevent progression or transition of disease.

2. Description of the Related Art

Chronic lower back pain is a primary cause of lost work days in the United States, and as such is a significant factor affecting both workforce productivity and health care expense. Therapeutic procedures for alleviating back pain range from conservative methods, e.g., with intermittent heat, rest, rehabilitative exercises, and medications to relieve pain, muscle spasm, and inflammation, to progressively more active and invasive surgical means which may be indicated if these treatments are unsuccessful, including various spinal arthroplasties, and eventually even spinal arthrodesis, i.e., surgical fusion.

There are currently over 700,000 surgical procedures performed annually to treat lower back pain in the U.S. In 2004, it is conservatively estimated that there will be more than 200,000 lumbar fusions performed in the U.S., and more than 300,000 worldwide, representing approximately a $1 B endeavor in an attempt to alleviate patients' pain. In addition, statistics show that only about 70% of these procedures performed will be successful in achieving this end.

Moreover, there may be multiple causes for a patient's lower back pain, where the pain generators are hypothesized to comprise one or more of the following: bulging of the posterior annulus or PLL with subsequent nerve impingement; tears, fissures or cracks in the outer, innervated layers of the annulus; motion induced leakage of nuclear material through the annulus and subsequent irritation of surrounding tissue in response to the foreign body reaction, or facet pain. Generally it is believed that 75% of cases are associated with degenerative disc disease, where the intervertebral disc of the spine suffers reduced mechanical functionality due to dehydration of the nucleus pulposus.

The intervertebral discs, located anterior to the vertebral canal, are formed of fibrous cartilage, and comprise the posterior and anterior longitudinal ligaments and the annulus fibrosis, circumferentially enclosing a central mass, the. The nucleus pulposus provides for cushioning and dampening of compressive forces to the spinal column. In a healthy adult spine, it comprises 80% water.

Surgical procedures, such as spinal fusion and discectomy, may alleviate pain, but do not restore normal physiological disc function.

With reference to FIGS. 1A and 1B, the vertebrae are the bony building blocks of the spine. Between each of the vertebral bodies are the spinal discs and this unit, comprising two vertebral bodies interfaced by an intermediate spinal disc, is known as a spinal motion segment. The spine has seven vertebrae in the neck (cervical vertebrae), twelve vertebrae in the mid-back (thoracic vertebrae), and five vertebrae in the low back (lumbar vertebrae). All of the vertebrae and discs are held together or surrounded by means of ligaments, which are strong fibrous soft tissues that firmly attach bones to bones. Ligaments contribute to the normal physiologic range of motion of the spine, and if injured, e.g., due to disc degeneration (described below) and ensuing impact on distribution of physiologic loads, they similarly may contribute to the resulting pain.

Thus, the bony spine is designed so that vertebrae "stacked" together can provide a movable support structure while also protecting the spinal cord's nervous tissue that extends down the spinal column from the brain from injury. Each vertebra has a spinous process, which is a bony prominence behind the spinal cord that shields the cord's nerve tissue. The vertebrae also have a strong bony "body" in front of the spinal cord to provide a platform suitable for weight-bearing.

The spinal discs serve as "dampeners" between each vertebral body that minimize the impact of movement on the spinal column. Each disc is comprised of the nucleus pulposus, a central, softer component, contained with in the, a surrounding outer ring.

With age, the water and protein content of the body's cartilage changes resulting in thinner, more fragile cartilage. Hence, the spinal discs and the facet joints that stack the vertebrae, both of which are partly composed of cartilage, are subject to similar degradation over time. The gradual deterioration of the disc between the vertebrae is known as degenerative disc disease, or spondylosis. Spondylosis is depicted on x-ray tests or MRI scanning of the spine as a narrowing of the normal "disc space" between adjacent vertebrae.

Radiculopathy refers to nerve irritation caused by damage to the disc between the vertebrae. This occurs because of degeneration of the annulus fibrosis of the disc, or due to traumatic injury, or both. Weakening of the annulus may lead to disc bulging and herniation, i.e., the nucleus pulposus or softer portion of the disc can rupture through the annulus and abut the spinal cord or its nerves as they exit the bony spinal column. When disc herniation occurs, the rupture of the nucleus pulposus the annulus fibrosis may irritate adjacent nervous tissue, causing local pain, or discogenic pain, in the affected area. Any level of the spine can be affected by disc degeneration. When disc degeneration affects the spine of the neck, it is referred to as cervical disc disease, while when the mid-back is affected, the condition is referred to as thoracic disc disease. Disc degeneration that affects the lumbar spine causes pain localized to the low back and is sometimes common in older persons and known as lumbago Degenerative arthritis (osteoarthritis) of the facet joints is also a cause of localized lumbar pain that can be diagnosed via x-ray analysis.

The pain from degenerative disc or joint disease of the spine may be treated conservatively with intermittent heat, rest, rehabilitative exercises, and medications to relieve pain, muscle spasm, and inflammation, but if these treatments are unsuccessful, progressively more active interventions may be indicated, including spinal arthroplasty including prosthetic nucleus device implantation; annulus repair, and total disc replacement, and eventually, even spinal arthrodesis, The intervention performed depends on the overall status of the spine, and the age and health of the patient. Procedures include removal of the herniated disc with laminotomy (a small hole in the bone of the spine surrounding the spinal cord), laminectomy (removal of the bony wall), by needle technique through the skin (percutaneous discectomy), disc-dissolving procedures (chemonucleolysis), and others.

When narrowing of the spaces in the spine results in compression of the nerve roots or spinal cord by bony spurs or soft tissues, such as discs, in the spinal canal this condition is known as spinal stenosis. Spinal stenosis occurs most often in the lumbar spine, i.e., the lower back, but also occurs in the cervical spine and less often in the thoracic spine. It is most often caused by degeneration of the discs between the vertebrae due to osteoarthritis. Rheumatoid arthritis usually affects people at an earlier age than osteoarthritis does and is associated with inflammation and enlargement of the soft tissues of the joints. The portions of the vertebral column with the greatest mobility, i.e., the cervical spine, are often the ones most affected in people with rheumatoid arthritis. Non-arthritic causes of spinal stenosis include tumors of the spine, trauma, Paget's disease of bone, and fluorosis In the context of the present invention, therapeutic procedures to alleviate pain are restore function are described in a progression of treatment from spinal arthroplasty to spinal arthrodesis. As used herein, spinal arthroplasty encompasses options for treating disc degeneration when arthrodesis is deemed too radical an intervention based on an assessment of the patient's age, degree of disc degeneration, and prognosis.

A wide variety of efforts have been proposed or attempted in the prior art, in an effort to relieve back pain and restore physiological function. Notwithstanding these efforts, there remains a need for methods and tools for accessing and preparing an intervertebral motion segment for subsequent therapeutic procedures, which can be accomplished in a minimally invasive manner.

SUMMARY OF THE INVENTION

The preferred embodiments of the invention involve surgical tools sets and methods for accessing and preparing vertebral elements, such as inter-vertebral motion segments located within a human lumbar and sacral spine, for therapeutic procedures. In the context of the present invention, "motion segments" comprise adjacent vertebrae separated by intact or damaged spinal discs.

In particular embodiments of the present invention, instrumentation system components and their means of use, individually and in combination and over or through one another, form or enlarge a posterior or anterior percutaneous tract; access, fragment and extract tissue (e.g., nucleus pulposus,); or otherwise prepare vertebral elements and inter-vertebral motion segments for fusion or dynamic stabilization via implantation of therapeutic agents and materials and spinal devices, are disclosed. It will be noted that the tools described can be used for and with the introduction of any number of devices, such as, for example, fusion devices, mobility devices, etc. Instrumentation is introduced and aligned (e.g., via preferably fluoroscopy, endoscopy, or other radio-imaging means, used as guidance to insure that the channel is positioned mid-line or along another desired reference axis relative to the anterior/posterior and lateral sacral view) through the percutaneous pathways and according to the trans-sacral axial access methods disclosed by Cragg, in commonly assigned U.S. Pat. Nos. 6,558,386, 6,558,390, and 6,575,979, each incorporated herein in their entirely by reference.

In another aspect, the present invention provides a series of surgical tools and devices, wherein the preferred embodiments of each are configured and constructed (e.g., cannulated; solid; blunt; beveled; angled; retractable; fixed; tilted; axially aligned; offset; extendible; exchangeable; stiff; flexible; deformable; recoverable; anchored; removable; biocompatible; able to be sterilized & machined; moldable; reusable; disposable) in accordance with optimal intended function and in deference to biomechanical and safety constraints.

Certain of the surgical tools take the form of elongated solid body members extending from proximal to distal ends thereof. Such solid body members may be used in combination or sequentially with elongated, cannulated body members. Hence, for example, design constraints, in addition to outside diameter (O.D.) tolerances and limitations imposed by virtue of patient anatomies, such as tube wall thickness, material selection/mechanical strength, and inside diameter (I.D.) also become considerations, e.g., to enable unrestricted passage over guide members or through hollow body members without incurring deformation that may impair or otherwise preclude intended function. Certain of these solid body and hollow body members can have distal means, mechanisms, or apertures that may be configured or manipulated for either precluding or facilitating engagement with tissue; the latter including piercing; tapping; dilating; excising; fragmenting; extracting; drilling; distracting (e.g. elevating); repairing; restoring; augmenting; tamping; anchoring; stabilizing; fixing, or fusing tissue. Certain of these solid body and hollow body members can have proximal means, mechanisms, pins, slots or apertures that may be configured or manipulated to engage; grasp; twist; pilot; angle; align; extend; expose, retract; drive; attach or otherwise interact to enable or facilitate the functionality of other components within the surgical tools set, e.g., the distal means and mechanisms noted above in this paragraph. In accordance with the certain embodiments disclosed herein, the individual components comprised in the tools sets, or kits, may include a guide pin introducer; guide pins with various distal end and proximal end configurations (e.g., tips; handles, respectively); soft tissue and bone dilators and dilator sheath(s); cutters; tissue extraction tools; twist drills; exchange systems comprising exchange bushing and exchange cannula assemblies; distraction tools; augmentation materials, and repair tools.

In a particularly preferred procedure, these instrumentation system components are aligned axially, under visualization, and progressively inserted into a human lumbar-sacral spine through the minimally invasive percutaneous entry site adjacent the coccyx to access the L5-S1 or L4-L5 disc space to perform a partial or total nucleectomy, without compromising the annulus fibrosis, unlike current surgical discectomy procedures. Conventional discectomies are performed through a surgically created or enlarged hole in the annulus that remains post-operatively, and represents a undesirable pathway due to the potential for extrusion and migration of natural or augmented tissue, or implants, and that also compromise the biomechanics of the physiological disc structure.

Moreover, in accordance with the techniques and surgical tool sets, and in particular the cutters and extraction tool configurations disclosed herein, a substantially greater amount (volume) of intradiscal material e.g., nucleus pulposus and cartilage, in comparison with other discectomy procedures in practice, may be removed, as needed. In particular, the instrumentation systems and techniques embodied in the present invention more effectively, with less immediate trauma, and without residual negative physiological impacts that may occur as a result of invasion of the annulus, prepare an inter-vertebral motion segment for subsequent receipt of therapeutic procedures, and enables axial placement of implants close to and in alignment with the human spine's physiological center of rotation.

Other specific advantages over current practice include: the patient is in a prone position that is easily adaptable to other posterior instrumentation; blood loss is minimal soft tissue structures, e.g., veins, arteries, nerves are preserved, and substantially less surgical and anesthesia time are required compared with conventional procedures.

There is provided in accordance with one aspect of the present invention, a cutter for disrupting material in an intervertebral space. The cutter comprises a cutter blade, having a first surface for positioning adjacent a vertebral end plate and a second surface separated from the first surface by a blade thickness. The blade has a first side and a second side, and at least one cutting edge on at least one of the first and second sides.

The cutting edge may be co-planer with the first surface, or the cutting edge may be co-planer with the second surface. Alternatively, the cutting edge may be centered on a plane which is positioned in between the first surface and the second surface. The cutter may include a first cutting edge on the first side and second cutting edge on the second side. The blade may comprise an elongated ribbon, which inclines radially outwardly from an axis of rotation. The ribbon may comprise a bend, at which the ribbon folds back upon itself. The ribbon may comprise a first end and a second end, and at least a first end includes an attachment structure for attachment to a rotatable driveshaft. The attachment structure may comprise an aperture. In one embodiment, both the first end and the second end are adapted for connection to the rotatable driveshaft. The blade may extend radially outwardly from an axis of rotation, and may be inclined in a distal direction. Alternatively, the blade may incline radially outwardly from an axis of rotation, in a proximal direction. Preferably, the cutter is secured to a rotatable driveshaft.

In accordance with a further aspect of the present invention, there is provided a method of preparing the spine for a subsequent procedure. The method comprises the steps of identifying an access site on the anterior surface of the spine. A lumen is formed from the access site into the sacrum, through at least one vertebral body and into at least one intervertebral disc. The intervertebral disc comprises a disc nucleus surrounded by a disc annulus. A cutter apparatus is introduced through the lumen and into the intervertebral disc. The cutter comprises an axially elongated rotatable shaft having at least one radially outwardly extending cutter blade. The cutter blade is rotated to disrupt nucleus material.

The method may additionally comprise the step of removing the nucleus cutter tool and introducing a nucleus removal tool. The method may additionally comprise the step of rotating the nucleus removal tool to engage disrupted nucleus material, and removing the disrupted nucleus material.

These and other advantages and features of the surgical tools sets and techniques disclosed in the present invention will be more readily understood from the following detailed description of the preferred embodiments thereof, when considered in conjunction with the accompanying figures.

BRIEF DESCRIPTION OF THE DRAWINGS

FIGS. 2A and 2B are a perspective view and a side cross-sectional view of one embodiment of a guide pin introducer, respectively, with pin and slot configuration.

FIG. 2D is a perspective view of one embodiment of a guide pin introducer-stylet-pin and slot configured assembly.

FIG. 2E is a side cross-sectional view of the assembly of FIG. 2D.

FIG. 3A is a perspective view of one embodiment of a guide pin introducer.

FIG. 3B is a side cross-sectional view of the guide pin introducer of FIG. 3A.

FIG. 6A is a side view of a guide pin detailing distal and proximal ends.

FIG. 6B is a side view of the distal end of one embodiment of a guide pin with a trocar tip configuration.

FIG. 6C is a side view of the distal end of an embodiment of a guide pin with a beveled tip configuration.

FIG. 6D is a side view of the proximal end of a preferred embodiment of a guide pin with a hex and flat configuration as means for tip alignment and axial and rotational locking.

FIG. 8C illustrates a guide pin with a cross-sectional view of female thread engagement coupling.

FIG. 8D is an enlarged view of the female thread engagement coupling in FIG. 8C.

FIG. 8E illustrates the guide pin extension with a cross-sectional view of a male thread engagement coupling.

FIG. 8F is an enlarged view of the male thread engagement in FIG. 8E.

FIG. 18A is an elevated view of one embodiment of a large teardrop debulker.

FIG. 18B is a rear elevational view of the portion teardrop debulker of FIG. 18A which attaches to the rotatable shaft.

FIG. 18C is another elevated view of a larger teardrop debulker of FIG. 18A.

FIG. 18D is an elevated view of one embodiment of a standard or medium size teardrop debulker.

FIG. 18E is a side isometric view of one embodiment of a large teardrop down-cutter.

FIG. 18F is a side isometric view of one embodiment of a medium teardrop down-cutter.

FIG. 18G is a side isometric view of one embodiment of a small teardrop down-cutter.

FIG. 19A is a side elevated perspective view of one embodiment of an extractor assembly unit.

FIG. 19B is a side elevated, partial cut-away view of the extractor assembly unit of FIG. 19A.

FIG. 19C is a side cross-sectional view of the extractor assembly unit of FIG. 19A.

FIG. 19D is a side elevated view of an extractor head prior to having its component wires unwound.

FIG. 23A is a perspective view of one embodiment of an insertion tool assembly comprising a packing instrument and a delivery cannula.

FIG. 23B illustrates engagement of the packing instrument with the delivery cannula, both from FIG. 23A.

FIG. 23C is perspective view of the packing instrument of FIG. 23A.

FIG. 23D is a perspective view of the delivery cannula of FIG. 23A.

FIG. 25A is a perspective view of one embodiment of an allograft placement tool.

FIG. 25B is a side cross-sectional view of the tool of FIG. 25A.

FIG. 25C is a side cross-sectional view of the allograft tip of the tool of FIG. 25A.

FIG. 26 is a side elevated view of an exchange bushing.

FIG. 27 is a side view of one embodiment of an exchange system assembly comprising an exchange bushing and an exchange cannula.

FIG. 28A is a side elevated, cut-away view of one embodiment of an exchange cannula of FIG. 27, in an open configuration.

FIG. 28B is a side elevated view of the exchange cannula of FIG. 27, in a closed configuration.

FIGS. 29A-B illustrate the use of the exchange system of FIGS. 26-28 to deliver a distraction device or an axial spinal implant of larger diameter than the dilater sheath.

FIG. 30A is side cross-sectional view of another embodiment of an exchange system assembly comprising an exchange bushing and an exchange tube.

FIG. 30B is a side cross-sectional view of the exchange bushing of FIG. 30A.

FIG. 30C is a side cross-sectional view of the exchange tube of FIG. 30A.

FIG. 31 is a perspective view of one embodiment of a temporary distraction rod and a tool that can be used to deliver or remove the rod from a treatment site.

FIG. 32A is a perspective, partial cut-away view of the temporary distraction rod of FIG. 32A and the distal portion of a tool that can be used to deliver the rod to the treatment site.

FIG. 32B is a perspective, partial cut-away view of the temporary distraction rod of FIG. 32A and the distal portion of a tool that can be used to remove the rod from the treatment site.

FIG. 34A is an exploded perspective view of one embodiment of a distraction-rod-assembly shown with the insertion tool.

FIG. 34B is a perspective view of the insertion tip of the assembly of FIG. 34A.

DETAILED DESCRIPTION OF THE PREFERRED EMBODIMENT

In accordance with one aspect of the embodiments described herein, there are provided surgical instrumentation systems and techniques for efficiently and atraumatically accessing and preparing treatment sites within the spine, such as, for example, vertebral motion segments, for subsequent therapeutic spinal procedures. In one approach, the step of accessing the treatment site includes using fluoroscopic imaging to visually align one or more components of the instrumentation system via a percutaneous, anterior trans-sacral axial approach. In another aspect, the treatment site includes a spinal disc and the subsequent therapeutic procedure includes nucleectomy. In yet another aspect, the therapeutic procedure includes immobilization devices to facilitate fusion; deployment of augmentation media; deployment of dynamic stabilization implants, or mobility devices to preserve or restore physiologic function.

In accordance with one aspect of the embodiments described herein, there are provided surgical tool sets and methods of using the tool sets. The tools of the tools sets can be used individually and/or in combination with each other. As will be explained in further detail below, in one approach, certain tools fit over other tools, and therefore can be used over each other. In another approach, the tools fit through each other, and therefore can be used through one another.

It will be understood that the access methods described can include the step of utilizing an anterior or posterior trans-sacral pathway. The therapies to the spinal discs and vertebral bodies described herein can be conducted on one or more spinal discs or vertebral bodies. In one approach, therapeutic procedures are performed through or on at least one spinal disc and at least one vertebral body traversed by at least one working channel.

For convenience, the exemplary access by a single anterior method, and treatment of only a single spinal disc or vertebral body is described herein. It will be understood, however, that the tools and methodologies described herein are applicable to any spinal access pathway, including without limitation open surgical procedures from any access orientation, and to any number of spinal discs and/or vertebral bodies.

Figure 1A:
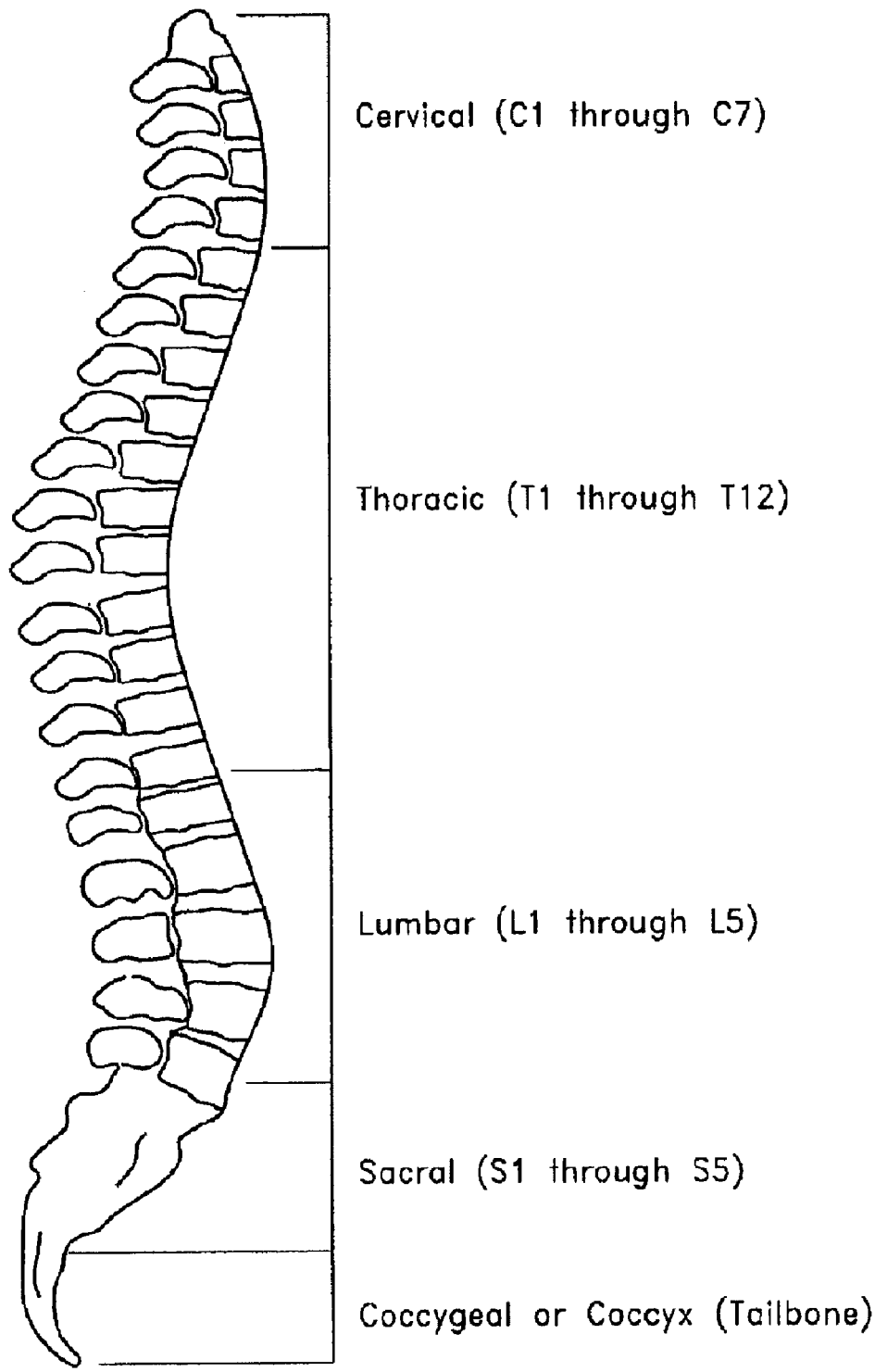
FIG. 1A provides a lateral view of a normal spinal column.
Figure 1B:
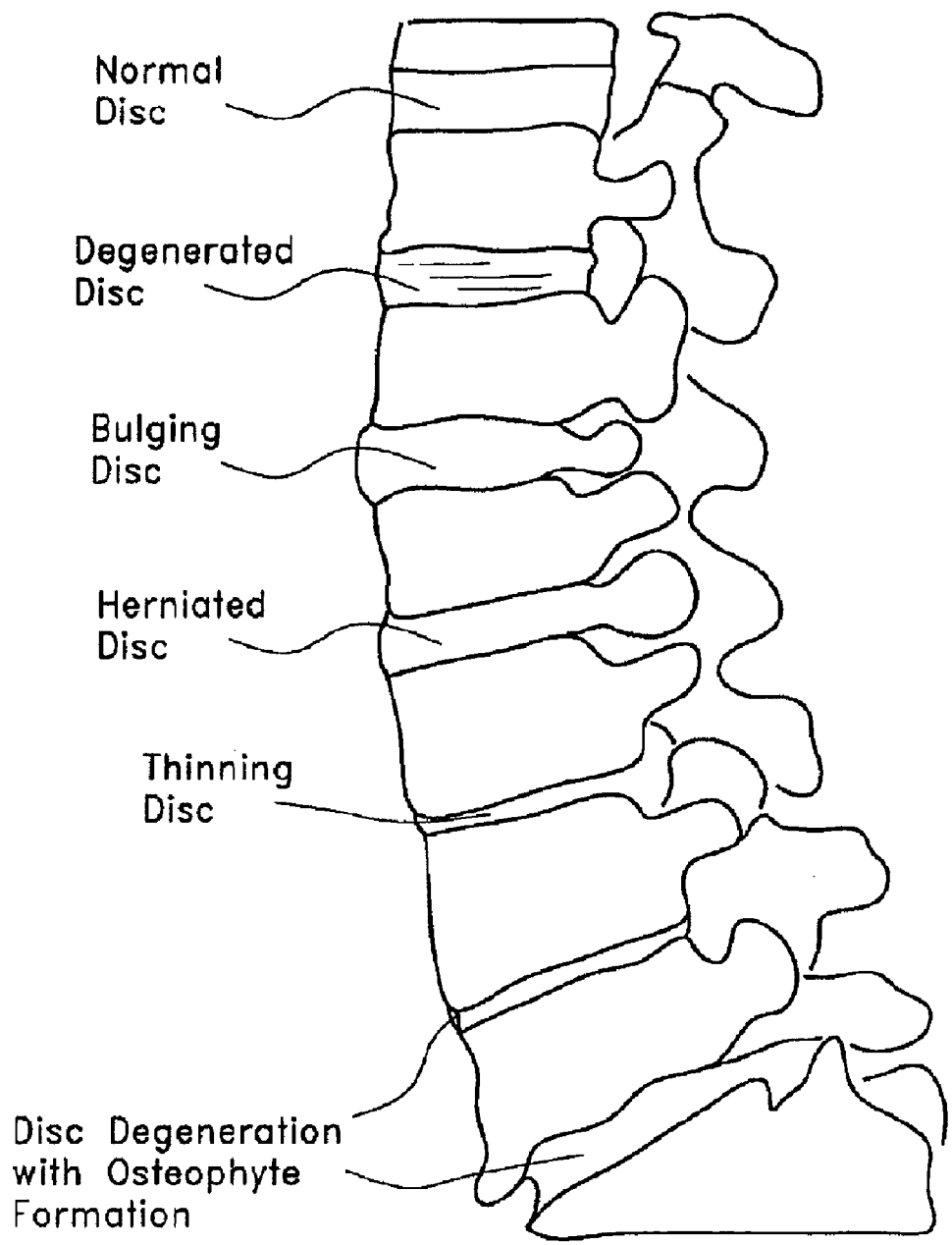
FIG. 1B illustrates examples of normal, degenerated, bulging, herniated, and thinning spinal discs.
Figure 1C:
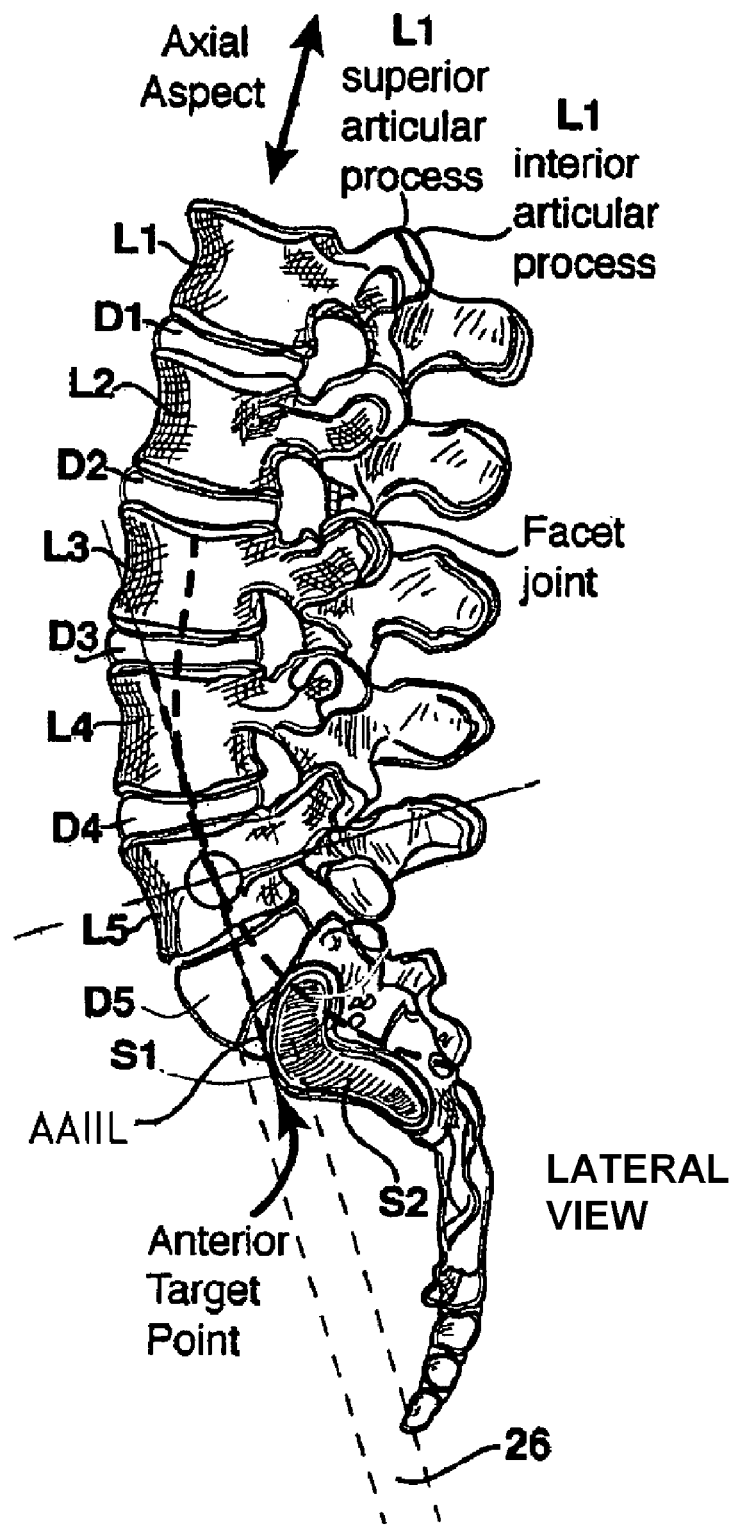
FIG. 1C is a lateral view of the lumbar and sacral portion of the spinal column depicting the visualized anterior axial instrumentation/implant line (AAIIL) extending cephalad and axially from the anterior laminectomy site target point.
Figure 1D:
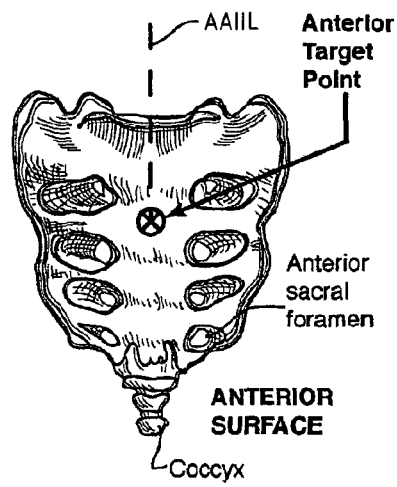
FIG. 1D is an illustration of an anterior target point on the sacrrum
Figure 1E:
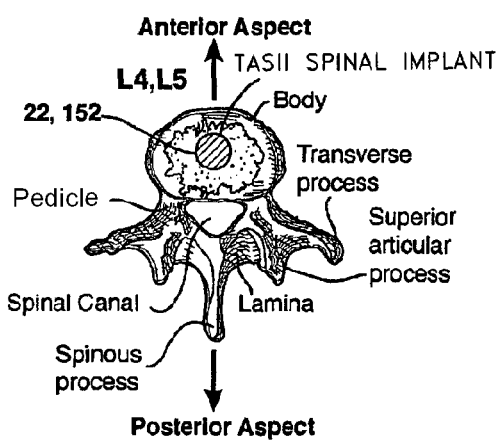
FIGS. 1E and 1F are cross-sectional caudal views of a lumbar vertebrae depicting one and two trans sacral axial implants respectively within corresponding TASII bores formed in parallel with the visualized AAIIL of FIG. 1C.
Figure 1F:
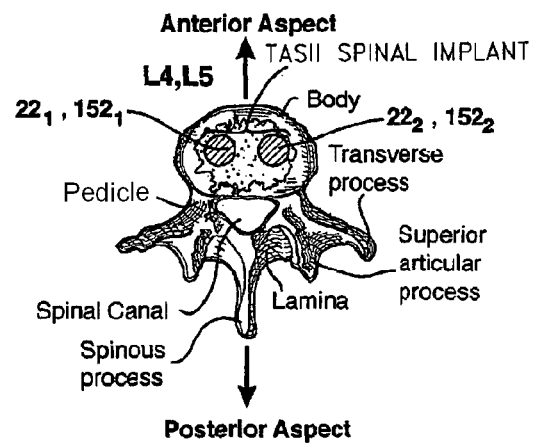

FIGS. 1C-D schematically illustrate the anterior trans-sacral axial spinal instrumentation/implant (TASII) approaches in relation to the lumbar region of the spinal column, and FIGS. 1E-F illustrate the location of a TASII implant or pair of implants within an anterior TASII axial bore 152 or pair of TASII axial bores $22_1$, $22_2$, or $152_1$, $152_2$. Two TASII axial bores and spinal implants or rods are shown in FIG. 1F to illustrate that a plurality, that is two or more, of the same may be formed and/or employed in side by side relation parallel with the anterior axial instrumentation/implant line (AAIIL).

The lower regions of the spinal column comprising the coccyx, fused sacral vertebrae S1-S5 forming the sacrum, and the lumbar vertebrae L1-L5 described above are depicted in a lateral view in FIG. 1C. The series of adjacent vertebrae located within the human lumbar and sacral spine have an anterior aspect, a posterior aspect and an axial aspect, and the lumbar vertebrae are separated by intact or damaged spinal discs labeled D1-D5 in FIG. 1C. FIG. 1D depicts the anterior view of the sacrum and coccyx.

The method and apparatus for forming an anterior TASII axial bore initially involves accessing an anterior sacral position, e.g. an anterior target point at about the junction of S1 and S2 depicted in FIGS. 1C and 1D. One (or more) visualized, imaginary, axial instrumentation/implant line extends cephalad and axially in the axial aspect through the series of adjacent vertebral bodies to be fused or otherwise treated, L4 and L5 in this illustrated example. The visualized AAIIL through L4, D4, L5 and D5 extends relatively straight from the anterior target point along S1 depicted in FIGS. 1C and 1D, but may be curved as to follow the curvature of the spinal column in the cephalad direction.

It will be noted that the terms trans-sacral axial spinal instrumentation/implant (TASII), and anterior axial instrumentation/implant line (AAIIL), as used herein, are analogous to the terms trans-sacral axial spinal instrumentation/fusion (TASIF), and anterior axial instrumentation/fusion line (AAIFL), The analogous terms generally refer to the same percutaneous pathways, the primary difference being the types of treatments and implants delivered through the respective percutaneous pathways.

U.S. Pat. No. 6,575,979, issued Jun. 10, 2003, titled METHOD AND APPARATUS FOR PROVIDING POSTERIOR OR ANTERIOR TRANS-SACRAL ACCESS TO SPINAL VERTEBRAE, hereby incorporated in its entirety into this disclosure by reference, discloses in detail tools and methodology for accessing targeted treatment sites, such as, for example, inter-vertebral motion segments.

Certain of the access and preparation surgical tools, as explained in U.S. Pat. No. 6,575,979, take the form of elongated solid body members extending from proximal to distal ends thereof. Elongated solid body members in medical terminology include, for example, relatively stiff or flexible needles of small diameter typically used to penetrate tissue, wire stylets typically used within electrical medical leads or catheters to straighten, stiffen, or impart a curved shape to the catheter, guidewires that are used to traverse body vessel lumens and access remote points therein (certain hollow body guidewires have lumens for a number of uses), and obturators. Obturators are typically formed as rods provided in various diameters with blunt distal tips that can be manipulated to penetrate, separate or manipulate surrounding tissue without cutting or damaging the tissue.

As used herein, the term "guide pin" can include solid body members (e.g., guidewires) employed to perform the functions of guide pin delivery and guidance described herein, unless the exclusive use of a given one of such solid body members is explicitly stated. Such solid body members can be stiff or flexible and can include distal anchoring mechanisms, e.g., sharpened or beveled tips.

Certain others of the surgical tools take the form of hollow body, tubular members having lumens extending from proximal to distal ends thereof. Such hollow body, tubular members can take the form of medical catheters, medical cannulas, medical tubes, hollow needles, trocars, sheaths, or the like, or variations thereof. Such hollow body tubular members employed in various embodiments described herein can be stiff or flexible and can include distal fixation mechanisms.

As used herein, anterior refers to in front of the spinal column (ventral) and posterior refers to behind the column (dorsal). As used herein, proximal (caudal) refers the end or region that is closer to the surgeon or sacral region of the spine, while distal (cephalad) refers to the end or region that is closer to the patient's head.

In accordance with one aspect of the embodiments described herein, there is provided a guide pin introducer that can be used to facilitate access to the sacrum for delivery of at least one guide pin, which in turn serves as means over which other instruments of the surgical tools set can subsequently be delivered to target sites to perform their intended procedural functions, individually or in combination, over or through one another.

With reference to FIGS. 2A-B, in one aspect the guide pin introducer 100 comprises an introducer tube 102 and an introducer handle 110. The introducer tube 102 extends between a distal end 104 and a proximal end 106, and defines an inner, tubular member lumen 108. The length of the tube 102 is typically in the range of about 4" (100 mm) to about 12" (310 mm), often about 5" (120 mm) to about 9" (230 mm). In one exemplary embodiment, the length of the tube 102 is approximately 7". The tube 102 is preferably long enough to extend from a skin incision 190 near the paracoccygeal region, through the pre-sacral space, to an anterior target point 192, as shown, for example, in FIGS. 4 and 5.

Figure 2C:
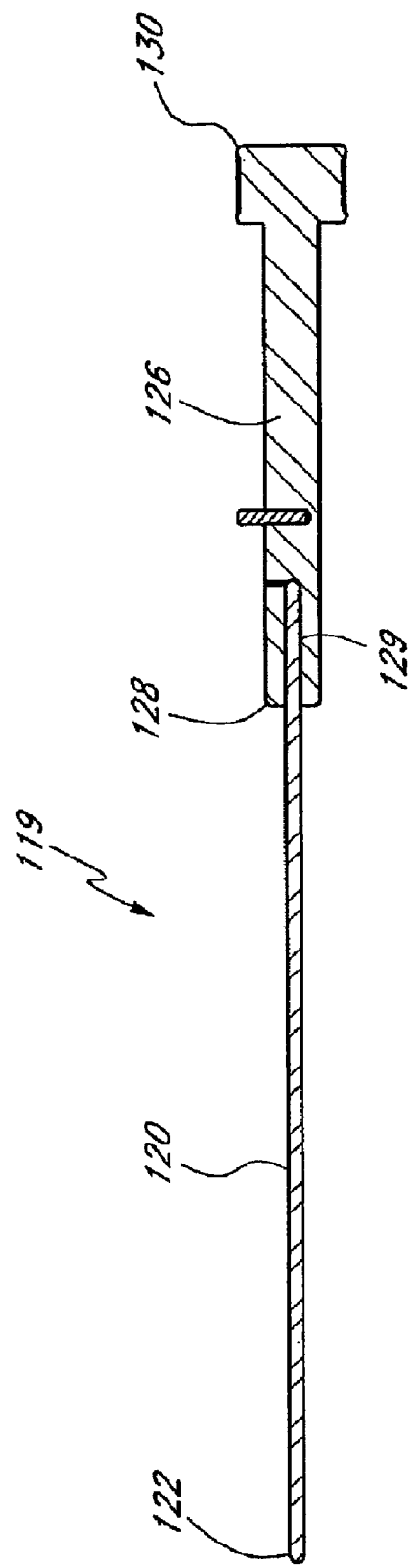
FIG. 2C is a side cross-sectional view of one embodiment of a stylet with pin configuration.
Figure 3C:
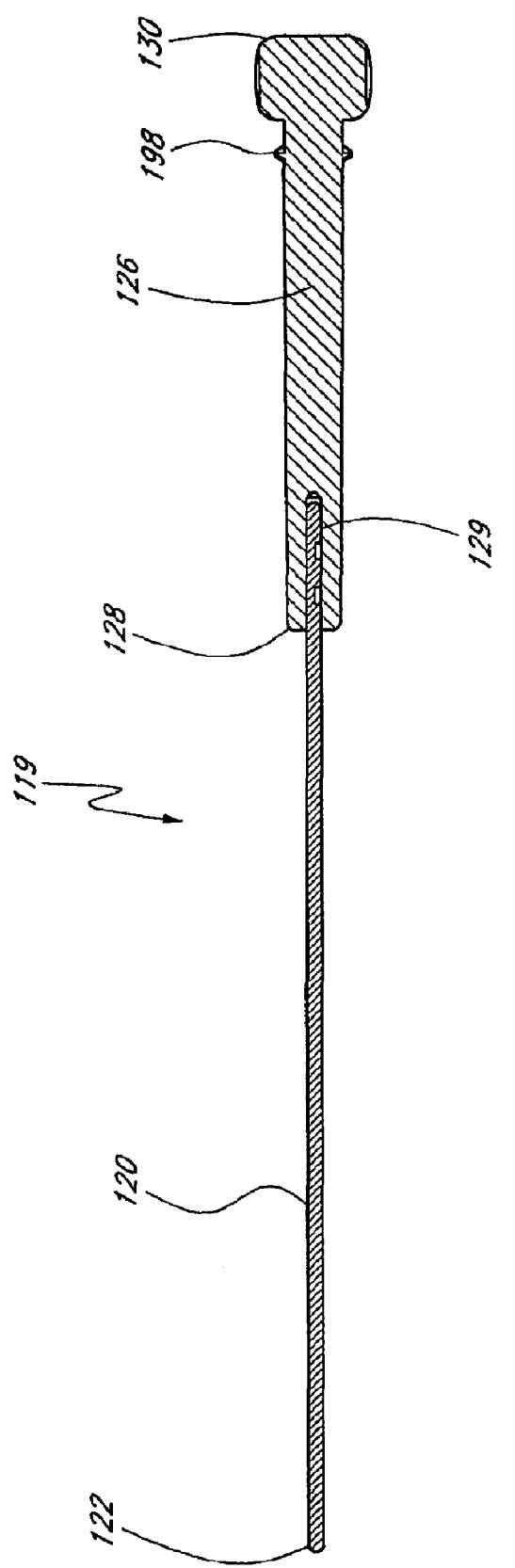
FIG. 3C is a side cross-sectional view of one embodiment of a stylet with multi-start thread configuration.
Figure 3D:
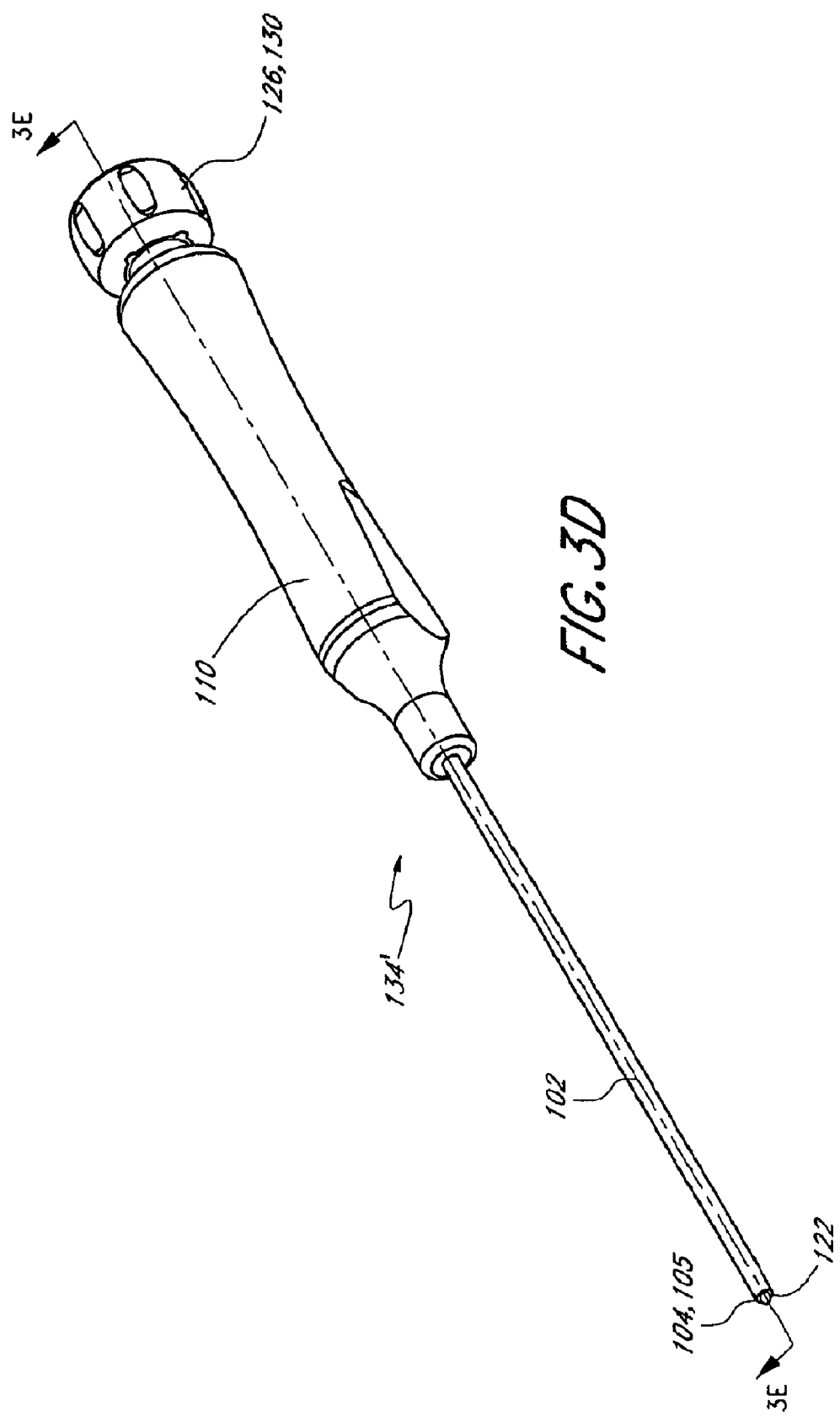
FIG. 3D is a perspective view of one embodiment of a guide pin introducer-stylet multi-start thread configured assembly.
Figure 3E:
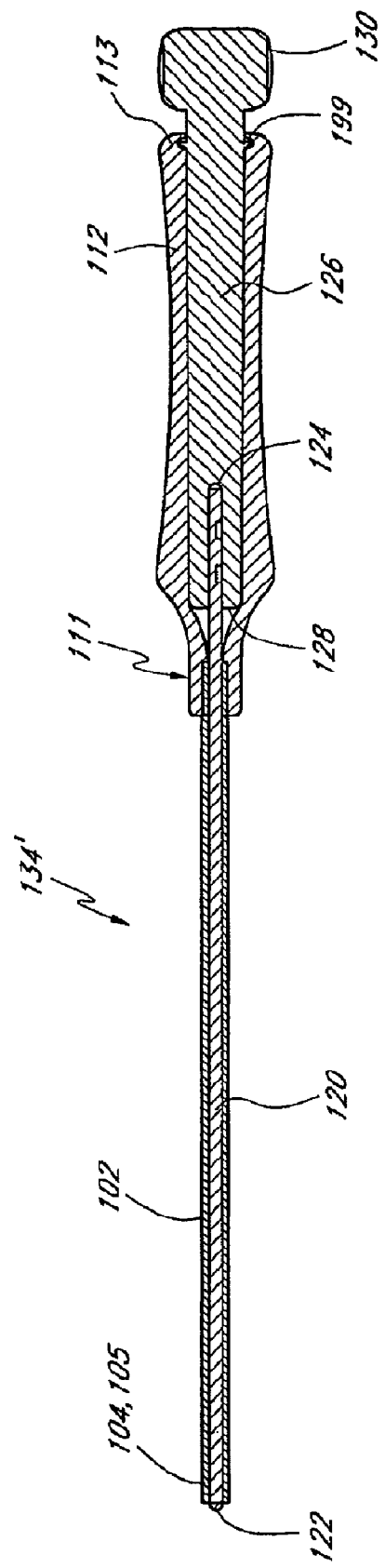
FIG. 3E is a side cross-sectional view of the assembly of FIG. 3D.

With reference to FIGS. 3A and 3B, an exemplary embodiment of a guide pin introducer with multi-start thread 199 assembly engagement means is shown. The inner diameter (I.D.) of the introducer tube 102 is typically in the range of about 2 mm to about 5 mm, often about 3 mm to about 4 mm. In one exemplary embodiment, I.D. of the tube 102 is about 3.5 mm (0.13"). The outer diameter (O.D.) of the tube 102 is typically in the range of about 4 mm to about 7 mm, often about 5 mm to about 6 mm. In one exemplary embodiment, O.D. of the tube 102 is about 5.5 mm, with an I.D. dimensioned to slidably receive the distally located blunt tip 122 of the stylet 119, as shown in FIGS. 2C-2E It will be noted that the actual dimensions (e.g., length, inner diameter, outer diameter, etc.) of the tube 102 or any of the tools and components parts thereof described herein will depend in part on the nature of the treatment procedure and the physical characteristics of the patient, as well as the construction materials and intended functionality, as will be apparent to those of skill in the art.

The edge 105 at the distal end 104 of the tube 102 can comprise any number of configurations. In one embodiment, the edge 105 is at approximately a 90 degree angle relative to the longitudinal axis of the tube 102. In another embodiment, the edge 105 is beveled at an angle relative to the longitudinal axis of the tube 102. In one exemplary embodiment, the edge 105 is beveled at an angle of about 45 degrees. The tube 102 can be made from any of a number of known suitable materials, such as, for example, stainless steel, Ni—Ti alloys, or structural polymeric materials, or composites thereof.

With continued reference to FIGS. 4 and 5, in one mode of use, the guide pin introducer tube 102 serves as an enlarged diameter anterior tract sheath through which a guide pin, described in further detail below, can be introduced into the targeted site 192.

With reference to FIG. 2A-2B, the introducer handle 110 extends between a distal end 111 and a proximal end 113, and defines a tubular member lumen 109 that is stepped or tapered toward the distal end 111. The handle 110 comprises a slot at its distal end which is dimensioned to receive a section of the tube 102 beginning at the tube proximal end 106. The handle 110 and tube 102 can be molded, machined or otherwise formed as an integral unit, or can be affixed to each other by any of a variety of known attachment means, such as, for example, thermal bonding, adhesives, or press fits.

The introducer handle 110 can be made from any of a number of known suitable materials, such as, for example, polysulfone, polyvinylidene fluoride, polyethylenes, PEEK, or composites thereof. In one embodiment, introducer handle 110 is fabricated from an injection-molded part, made from an acetal-based copolymer, such as Delrin™ obtained from the DuPont Company in Wilmington, Del., that is then machined with an I.D. of about 13 mm (0.50") and an O.D. of about 19 mm (0.75"). Here, the overall length of the guide pin introducer 100 (i.e., the length of the tube 102 and integral handle 110, in total) is about 300 mm (11.95").

In accordance with one aspect of the embodiments described herein, there is provided a stylet with a blunt distal tip that can inserted into the guide pin introducer described above to facilitate advancement of the guide pin introducer to the targeted site without causing damage to surrounding tissue.

With reference to FIGS. 2D-E, in one embodiment, the stylet 119 comprises an elongate body or rod 120 that extends between a distal end 122 and a proximal end 124. The distal end 122 of the stylet rod 120 preferably comprises a blunt tip, thereby preventing damage to surrounding soft tissue as the guide pin introducer-stylet-pin-slot configuration assembly 134 (the approach assembly), which comprises the introducer 100 and stylet 119, described in further detail below, is advanced toward the targeted site, such as, for example, target point 192, shown in FIG. 4B.

With reference to FIGS. 2C-2E and FIGS. 4 and 5, in order to advance the introducer tube 102 through an anterior tract to the target point 192 without concomitant damage to surrounding soft tissue, a stylet 119 can be used in combination with the guide pin introducer 100 by advancing the introducer-stylet-approach assembly 134 to the target area or point 192.

The length of the rod 120 should be designed so that the stylet's blunt tip 122 extends beyond the distal end 104 of the guide pin introducer tube 102. In one embodiment, the rod 120 has an O.D. of about 3.2 mm (0.125"), which is less than the I.D. of the guide pin introducer 100. The stylet rod 120 can be made from any number of known suitable materials, such as, for example, stainless steel or the like.

The stylet handle 126 extends between a distal end 128 and a proximal end 130, and comprises a distally located bore 129 to receive the section of the stylet rod 120 beginning at the rod proximal end 124.

The length of the stylet handle 126 is typically in the range of about 3" (75 mm) to about 7" (175 mm), often about 4" (100 mm) to about 6" (150 mm). The O.D. of the handle 126 is typically in the range of about 0.25" (6 mm) to about 0.75" (20 mm), and generally dimensioned to cooperate with the introducer handle 110 to form the introducer (approach) assembly 134.

In one embodiment, the stylet handle 126 has a diameter of about 12 mm to about 13 mm (e.g., about 0.50") at the distal end 128 that increases to about 20 mm (0.75") at the proximal end 130. The length of the exposed rod 120 and narrow portion of the handle 126 together is about 300 mm (12") so that just the tip 122 of the stylet 119 will protrude from the distal end 104 of the introducer tube 102 upon assembly with the guide pin introducer 100. The narrow portion of the stylet handle 126 is configured to fit in a tubular member lumen 109 machined to receive it within the handle 110 of the guide pin introducer 100.

The stylet handle 126 can be formed from any of a variety of materials, such as, for example, polymeric materials having desired properties (e.g., able to be machined or an injection-moldable polymer). Suitable materials include, but are not limited to polysulfone, polyvinilydene fluoride, acetal-copolymer; acrylic, high density polyethylene, low density polyethylene, nylon, polycarbonate, polypropylene, PVC, or the like, or combinations thereof.

With reference to FIGS. 2A-2E and FIGS. 4 and 5, in one aspect, the guide pin introducer 100 can be provided with a releasable interlock that prevents the blunt-tipped stylet 119 from retracting proximally within the lumens 108, 109 of the cannulated guide pin introducer 100, thereby maintaining the extension and exposure of the blunt tip 122 of the stylet 119 beyond the distal end 104 of the tube 102 as the introducer (approach) assembly 134 is advanced by the surgeon toward the target point 192, optionally with the assistance of any known suitable visualization technique.

The releasable lock may comprise any of a variety of interference fit or friction fit surfaces carried by the stylet 119 for cooperating with a complementary structure on the introducer 100. It will be noted that the releasable interlock can be on and between any of the approach assembly 134 components described herein.

In one embodiment, illustrated in FIGS. 2A-E the releasable interlock of the introducer 100 comprises a track 112 that is configured to accept the locking pin 139 of the stylet 119, described in further detail below. The handle 110 of the introducer 100 comprises an axially extending slot or track 112, machined or otherwise formed through the wall of the handle 110. Track 112 is positioned with an open end beginning at the proximal end 113 and extends longitudinally in the distal direction along the handle 110 with a circumferentially extending notch 107 at the distal end of the track 112.

The stylet handle 126 comprises a radially outwardly extending engagement structure such as a locking pin 139 that is configured to slideably fit within the track 112 of the introducer handle 110. As the stylet handle 126 is advanced distally into engagement with the introducer handle 110, the locking pin 139 advanced distally through the opening on the proximal end 113 of the introducer handle 110, and along the axially extending track 112. Once the stylet handle 126 has been advanced fully into engagement with the introducer handle 110, rotation of the stylet handle 126 with respect to the introducer handle 110 advances the locking pin 139 into the circumferentially extending notch 107. The locking pin 139 serves as an interior stop or locking lug that releasably secures the stylet handle 126 within the introducer handle 110. In one embodiment, the locking pin 139 comprises a 0.125" (3.2 mm)×0.625" (15.8 mm) dowel pin.

In one embodiment, shown in FIGS. 2D-2E, the approach assembly 134 comprises the introducer 100 and the stylet 119 which are releasably interlocked to each other. The stylet handle 126 and the guide pin introducer 100 can be mutually releasably engaged by the above-described locking pin 139, other complementary surface structures, twist-lock mechanisms, such as in a preferred multi-start thread configuration shown in FIGS. 3A-3E; a modified Luer lock, or any other known suitable mechanism that enables mechanical quick release (e.g., relative to another embodiment that uses a press-fit method of engagement of the respective handles). With respect to the multi-start thread configuration shown in FIGS. 3A-3E, the guide pin introducer 100 has internal threads 199 on the proximal end 113 that engage with external threads 198 on stylet handle 126. Engagement and disengagement of the assembly 134' is by means of twist-lock. These quick release mechanisms facilitate disengagement of the stylet handle 126 from the guide pin introducer handle 110 once the distal end 104 of the guide pin introducer tube 102 is brought into relatively close proximity to the target 192. The stylet 119 can be disengaged from the rest of the approach assembly 134 and removed from the patient's body.

With reference to FIGS. 2D-2E, in one exemplary method of use, the stylet 119 is inserted into the lumens 108, 109 of the introducer tube 100 in a manner and configuration such that the blunt tip 122 extends and is preferably exposed from about 1 mm to about 2 mm beyond the distal end 104 of the guide pin introducer 100. In this manner, the blunt tip 122 of the stylet 119 serves as a soft tissue dilator that assists in the safe and atraumatic positioning of the distal end 104 of the guide pin introducer tube 102 in close proximity to the anterior target site 192.

The stylet rod 120 is inserted into the cylindrical polymeric handle 126 so that about 200 mm (about 7.76") of the rod 120 extends out of the handle 126, into and through introducer tube 102, and beyond the introducer tube distal end 104, so that the distal end blunt tip 122 of the rod 120 is exposed at the distal most end of the approach or introducer assembly 134.

Figure 5:
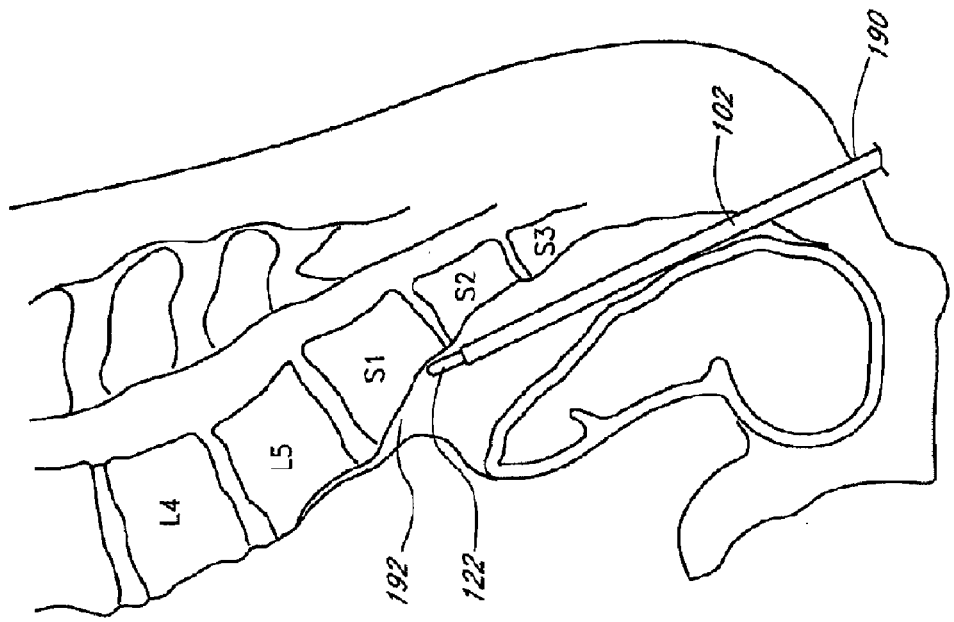
FIGS. 4 and 5 are lateral, partial cross-sectional views of the lumbar and sacral portion of the spine depicting delivery of the distal end of guide pin introducer-stylet-assembly to the anterior surface of the S1 vertebral body.
Figure 4:
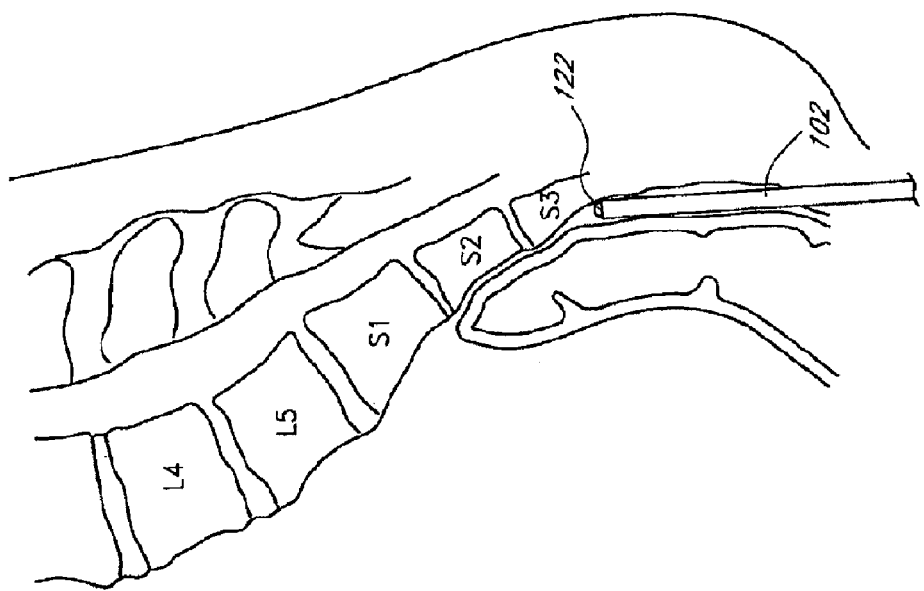

As shown in FIGS. 4 and 5, in one exemplary method of use, the spine is accessed via a small skin puncture 190 adjacent to the tip of the coccyx bone. The pre-sacral space is entered using any known suitable percutaneous technique. The introducer assembly 134, with the stylet's blunt tip 122 serving as a dilator, is advanced through the paracoccygeal entry site. Once the tip 122 of the stylet 119 is advanced through the facial layer, the blunt tip 122 is positioned against the anterior face of the sacrum and advanced along the anterior surface of the sacrum to the desired position or targeted site 192—here, the S1 vertebral body. In one embodiment, the distal portion of the approach assembly 134 is advanced to the targeted site under fluoroscopic guidance, as is described in co-pending U.S. patent application Ser. No. 10/125,771, filed on Apr. 18, 2002, titled METHOD AND APPARATUS FOR SPINAL AUGMENTATION.

The stylet 119 is released and removed from the approach assembly 134 after the distal portion of the assembly 134 is advanced to the targeted site 192, thereby leaving the distal portion of the introducer 100 at the targeted site, to preface the introduction of a guide pin through the introducter 100 to the targeted site 192

Figure 7A:
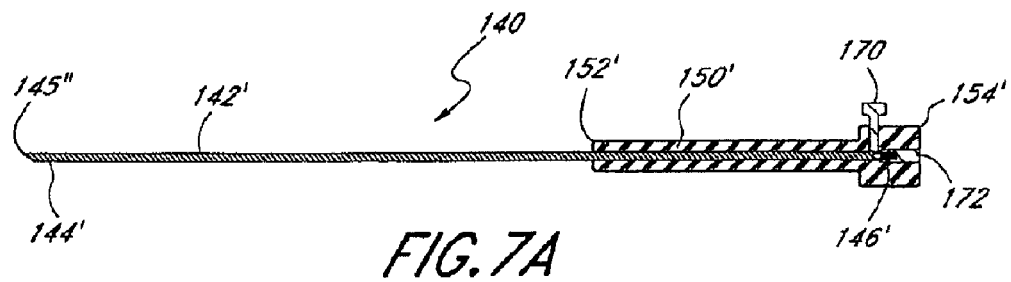
FIG. 7A is a cross sectional view of a guide pin-guide pin handle assembly.
Figure 7B:
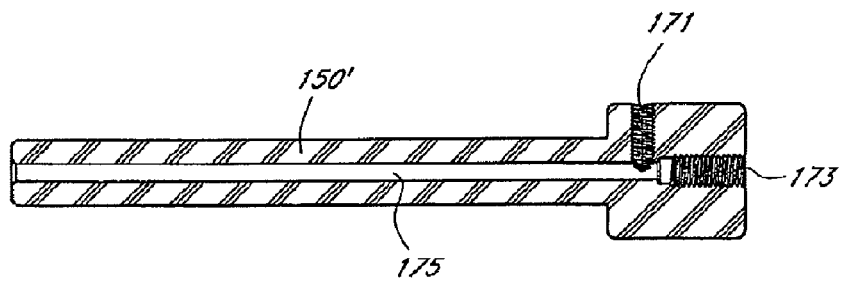
FIG. 7B is a cross sectional view of a guide pin handle.
Figure 7C:
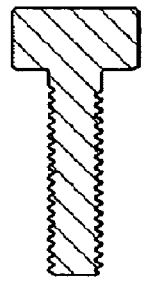
FIG. 7C depicts the thumb screw, for locking the guide pin.
Figure 7D:
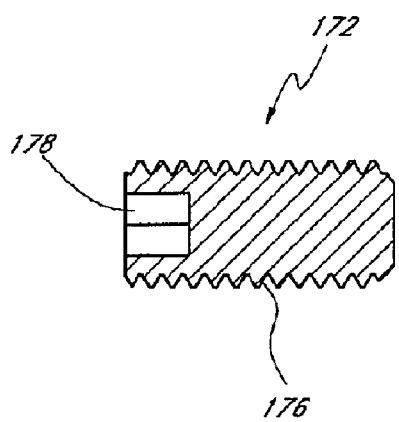
FIG. 7D illustrates a means for guide pin stop and steering.

In accordance with one aspect of the embodiments described herein, there is provided a guide pin that can be delivered to the targeted site through the use of a guide pin introducer, such as, for example, introducer 100 described above. In one embodiment, shown in FIG. 7A the guide pin assembly 140 has an elongate guide pin 142 that extends between a distal end 144 and a proximal end 146. The guide pin assembly 140 also has a sharp guide pin tip 145 at the distal end 144 and a preferably releasable handle 150 engaged at the proximal end 146.

Figure 7E:
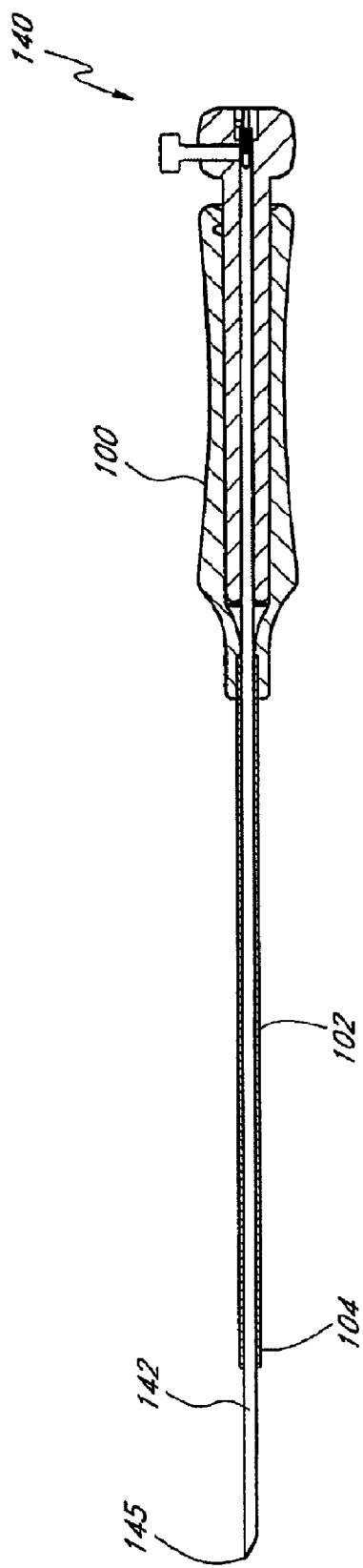
FIG. 7E depicts a guide pin assembly inserted within an introducer illustrating the guide pin tip extending beyond the distal end of the introducer.

The length of the guide pin 142 is typically in the range of about 9" to about 15", often about 11" to about 13". In one exemplary embodiment, the length of the guide pin 142 is approximately 12". The length of the guide pin 142 is typically sufficiently long so that the tip 145 extends beyond the distal end 104 of the guide pin introducer tube 102 when the guide pin assembly 140 is inserted within the introducer 100, as shown in FIG. 7E.

The guide pin 142 can be made from any of a number of suitable materials, such as, for example, stainless steel, NiTi alloys, or composites thereof. In one embodiment, the guide pin 142 is formed from substantially the same materials (e.g., stainless steel) as the stylet 119 and comprises a solid, elongated body 142 with an O.D. of between about 2.2 mm (0.090") to about 3.4 mm (0.13") and a length of about between about 300 mm (12.00")-600 mm (24").

Unlike the stylet 119, the guide pin tip 145 is not blunt, and may be shaped according to one among various configurations. In one embodiment, not illustrated, the guide pin tip is formed as a simple conical or two sided wedge pointed tip. In another embodiment, shown in FIG. 6B, the tip 145' is formed as a trocar tip that has a three-sided bevel at 15 degrees. In still another embodiment, shown in FIG. 6C, the tip 145" is formed as a beveled tip that has one side beveled at an angle. The angle can range, for example, from about 30 degrees to about 60 degrees relative to the longitudinal axis of the guide pin 142. The selection of the tip 145 geometry is influenced by the need to initially tack the guide pin 142 into the target, such as, for example, the sacral face, without having the guide pin 142 slip off or slide up the target surface. Pointed tip geometries enable the guide pin 142 to snag the sacral face, and thus eliminate "skidding" effects that may otherwise accompany tapping the target surface.

Figure 7F:
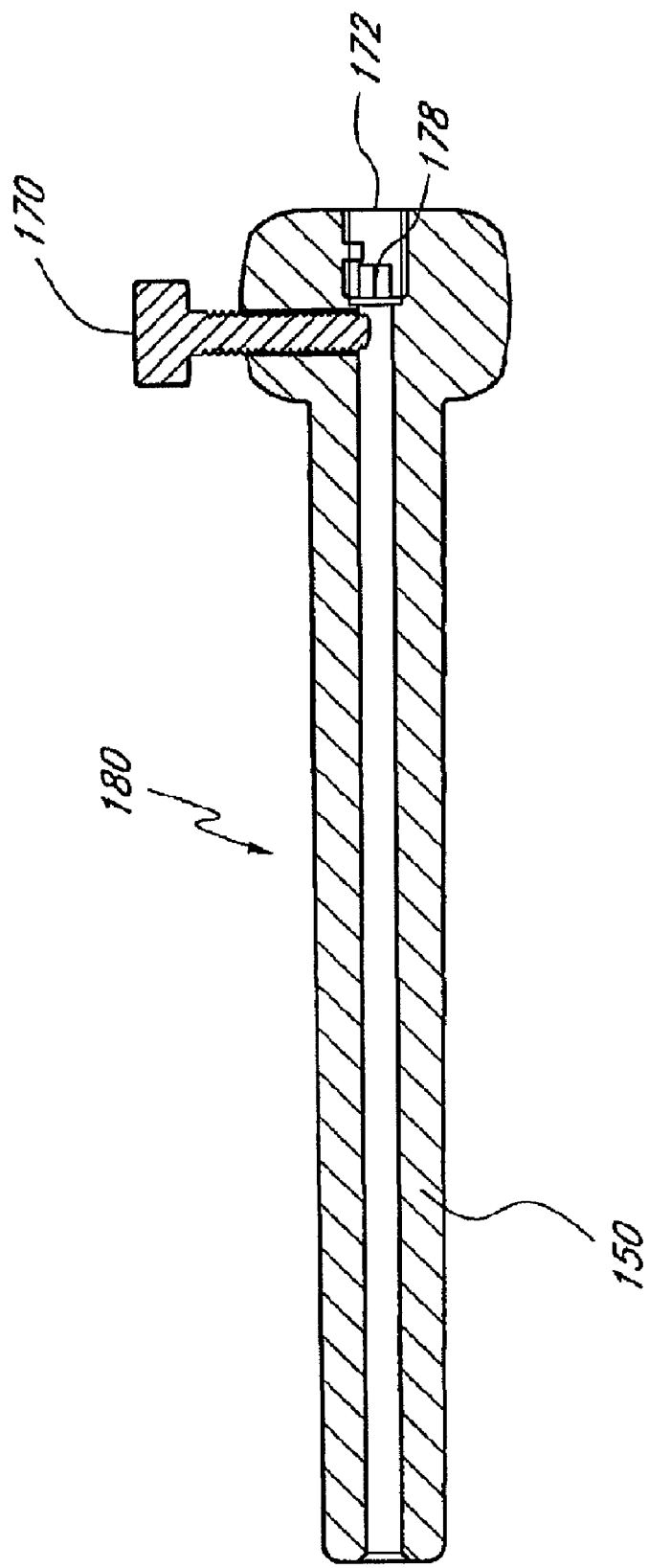
FIG. 7F is a cross section view illustrating a guide pin handle assembly, showing a releasable engagement means with the guide pin.

With continued reference to FIG. 7A-7D, in one embodiment, the guide pin assembly 140 comprises a guide pin handle 150' that comprises a distal end 152' and a proximal end 154', and comprises a distally located lumen 175 to receive a section of the guide pin 142' beginning at the guide pin proximal end 146'. In one aspect, the guide pin handle assembly 180 shown in FIG. 7F comprising the guide pin handle 150 and thumb/set screw element 170 is configured to align and releasably engage the guide pin 142. In method of use, for example, a flat on guide pin 142 (see FIG. 6D) is positioned in a predetermined relationship to the bevel on guide pin tip 145, so that when the guide pin is assembled and locked within the guide pin handle, wherein the thumb screw is advanced against the flat of the guide pin, this enables the clinician to determine, with reference to the thumb screw, visual or tactile indicia on the proximal handle which will indicate the rotational orientation of the beveled tip. Thus in this manner, the surgeon is able to determine, and adjust or "steer" the guide pin tip 145 position. In another aspect of alignment and releasable engagement mechanisms, the guide pin handle assembly 180 comprises a metal hexagonal or square socket 178 within the insert 172 of the guide pin handle assembly 180 when mated with the proximal end of the guide pin hex 181 and flat 182 (FIG. 6D) it provides a positive stop precluding longitudinal and rotational motion of the guide pin 142 relative to the guide pin handle 150.

In one embodiment, the handle 150 has an O.D. of about 12 mm (0.50") on its distal end 152, an O.D. of about 20 mm (0.75") on its proximal end 154, and is approximately 100 mm (4") in length. A bore 175 is formed in the distal end 152 extending substantially through the guide pin handel 150, of about 3.5 mm (0.13") (i.e., substantially the same as the O.D. of the guide pin 142), into which the guide pin 142 can be releasably inserted.

The guide pin handle 150 can be formed from any of a variety of materials, such as, for example, polymeric materials having desired properties (e.g., able to be machined or an injection-moldable polymer). Suitable materials include but are not limited to sterilizable polymeric materials, e.g., polyvinilidine fluoride; polysulfone; acetal-copolymer; acrylic, high density polyethylene, low density polyethylene, nylon, polycarbonate, polypropylene, PVC, or the like, or combinations thereof.

The guide pin handle 150 is configured to be able to "steer" a guide pin 142 in the event that there is axial misalignment of the its after insertion. In the context of the present invention, "steer" refers to an ability to manipulate by turning and make controlled positional adjustments of a guide pin 142 once it is tapped through the cortical bone of its anterior target 192. Specifically, the thumb/set screw 170 (FIG. 7C) serves as a point of reference to the tip 145 orientation and is particularly configured to mark the alignment of the guide pin's beveled tip 145, as opposed to the face of the beveled plane. When the guide pin is advanced it will tend to deviate in the direction of beveled tip, which is indicated, e.g., by the thumb screw. For example, if upon insertion the beveled plane of the tip 145 faces anterior, the guide pin 142 will track in the posterior direction when advanced.

While the visualization of the guide pin 142 in situ is facilitated, for example, by fluoroscopy, resolution limitations are frequently less ideal with respect to the guide pin tip 145 configuration. For this reason, the addition of the set screw 155 and thus the ability to steer the guide pin 142 via its handle 150 represent a significant procedural advantage enabled by the tools and techniques of the present invention.

One exemplary method of use involves: advancing the distal portion of a delivery assembly 159 to the targeted site; removing the guide pin handle 150; removing the introducer 100; and leaving the guide pin 142 at, and attached to, the targeted site 192. In one approach, the guide pin handle 150 and the introducer 100 are removed separately. In another approach, the handle 150 and the introducer 100 are removed together, leaving only the guide pin 142 in place.

Figure 8A:
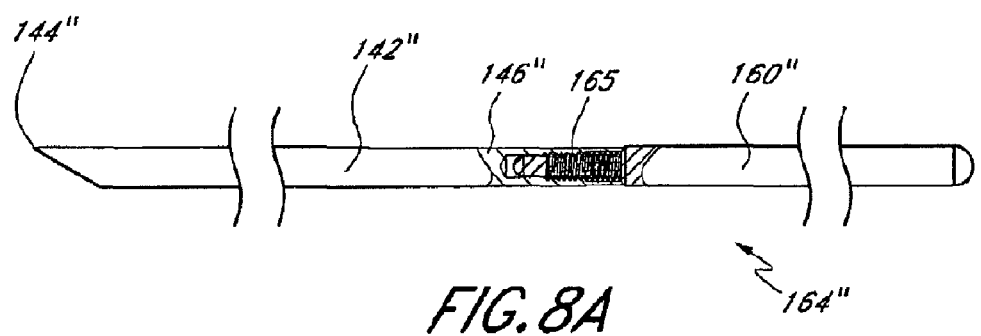
FIG. 8A illustrates a guide pin-guide pin extension assembly with a threaded engagement coupling.
Figure 8B:
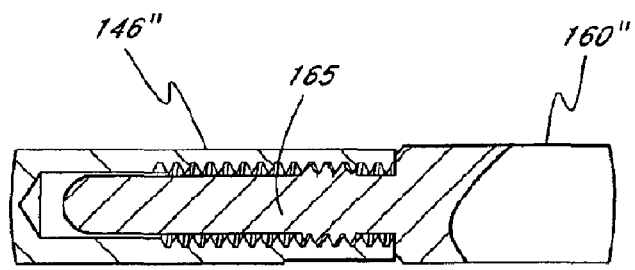
FIG. 8B is a detailed view of guide pin-guide pin extension assembly with a threaded engagement coupling.

Disengagement of the guide pin handle 150 from the proximal end 146 of the guide pin 142 enables extension of the guide pin's elongate body length through the addition of an extension 160 that can be attached to extend the length of the pins, thereby resulting in an extended guide pin, such as, for example, the long guide pin 164" of FIG. 8A which extends between a distal end 144" and a proximal end 146".

In accordance with one aspect of the embodiments described herein, there is provided a guide pin that can be extended in length to facilitate the subsequent delivery and utilization of other access and preparation tools.

Figure 8G:
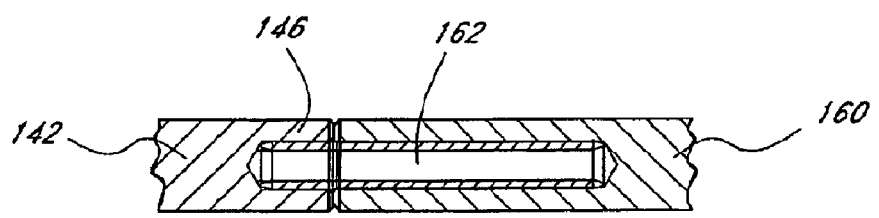
FIG. 8G illustrates an alternative embodiment of a guide pin-guide pin extension assembly with a friction fit engagement coupling.

With reference to FIG. 8G, in one embodiment, the guide pin 142 can be extended in length along its longitudinal axis via the addition of an extension 160, which has a connector 162 on its distal end. In this exemplary embodiment, the extension 160 comprises an exchange pin, and the connector 162 comprises a roll pin.

The guide pin 142 has a bore that is located at its proximal end 146 and that is dimensioned to receive a distal portion of the connector 162. The extension 160 has a bore that is located at its distal end and that is dimensioned to receive a proximal portion of the connector 162.

In one embodiment, the guide pin 142, extension 160, and connector 162 are releasably interconnected by any known suitable approach, such as, for example, an interference fit or friction fit or the like. In one embodiment, the connector 162 is fixedly secured to the distal end of the extension 160 and the connector is releasably secured to the proximal end of the guide pin 142.

With reference to FIGS. 8A-F, in a preferred embodiment, the extended guide pin 164" comprises a guide pin 142" and an extension 160" that are connected to each other through the use of a connector 165, which protrudes from the distal end of the extension 160". The proximal end of the guide pin 142" has a threaded bore 148 at its proximal end 146" that is dimensioned to receive the connector 165.

In this preferred embodiment, the connector 165 comprises a threaded stud. The connector 165 extends between a distal end 166 and a proximal end 167 and has a smaller outer diameter towards its distal end 166, as compared to the larger outer diameter toward its proximal end 167. The connector 165 comprises screw threads 168 for releasably securing the extension 160" to the guide pin 142", which itself has a threaded bore 148 having threads 149 that is complementary to the threads 168 of the connector 165.

The length of the extended guide pins (e.g., 164, 164") can range from about 400 mm to about 800 mm, often about 500 mm to about 700 mm. In one embodiment, the length of pin 164 is about 600 mm (24.00").

In one exemplary method of use, following the delivery of the introducer-stylet approach assembly 134 to the targeted site 192 and removal of the stylet 119 from the introducer 100, a guide pin-guide pin handle assembly 140 is inserted into the cannulated guide pin introducer 100. As the guide pin 142 is initially tapped into the sacrum it is in effect serving as a bone dilator. Once the guide pin tip 145 has been inserted (tapped) into the anterior face of the S1 vertebral body, the guide pin introducer 100 and the guide pin handle 150 are removed, to enable engagement of the guide pin 142 with the guide pin extension 160.

Subsequent components from among the surgical tools sets described herein, which generally have a greater O.D. than the extended guide pin 164, are introduced to the target site 192 by concentric passage over the extended guide pin 164. The subsequent components can be advanced over the extended pin 164 individually or in combination, over or through one another, to the targeted site 192. For example, in one approach, the first tools in the sequence of instruments to be delivered over the guide pin 164 are bone dilators, described in further detail below.

In accordance with one aspect of the embodiments described herein, there are provided certain materials which can enhance visualization of tools via radio-imaging (e.g., fluoroscopy). Examples of such materials include stainless steel where tools or portions thereof comprise metal, and powders, such as barium sulfate, for components configured from polymeric materials, e.g., bushings, that may be inserted within the body cavity. It will be understood that such materials can be incorporated during the formation of certain metal or polymeric compounds comprised in the surgical tools sets and devices disclosed herein.

Although dilation of soft tissue is common for certain surgeries, dilation of bone tissue is generally not a common technique for orthopedic procedures. In one approach, dilating bone in the spine involves: widening the axial pathway or channel in preparation for subsequent treatments by compressing cancellous bone or cortical bone shell to the side rather than removal via cutting or coring such bone material.

Compression is usually a less traumatic procedure than coring with, for example, an electrically powered drill, as the latter may inadvertently cut or tear soft tissue, including nerves or blood vessels. Less bleeding of the bone occurs with dilation, which is an unanticipated benefit. It is believed that the compression of the bone by the dilator results in a tamponade effect so that the amount of bleeding from bone accompanying this procedure is reduced. Compression appears to afford stronger "anchoring", for subsequent implants (e.g., implants with threading) within an inter-vertebral space. It is also possible that compression may have a long term beneficial impact via the initiation of subsequent osteogenic (bone growth) effects.

In accordance with one aspect of the embodiments described herein, there are provided bone dilators that can be used to create and widen one or more channels in the vertebral bodies for the ensuing passage of other instruments and devices. In one embodiment, the dilators are cannulated and can be delivered accurately to the target site, following removal of any preceding dilators, in succession one after another, each directly over the guide pin. In another embodiment, the dilators are configured to pass concentrically over a previously delivered smaller dilator (i.e., a dilator having a relatively smaller O.D than the ID of successive dilators.), without the extraction of the smaller dilator over the guide pin.

Figure 11:
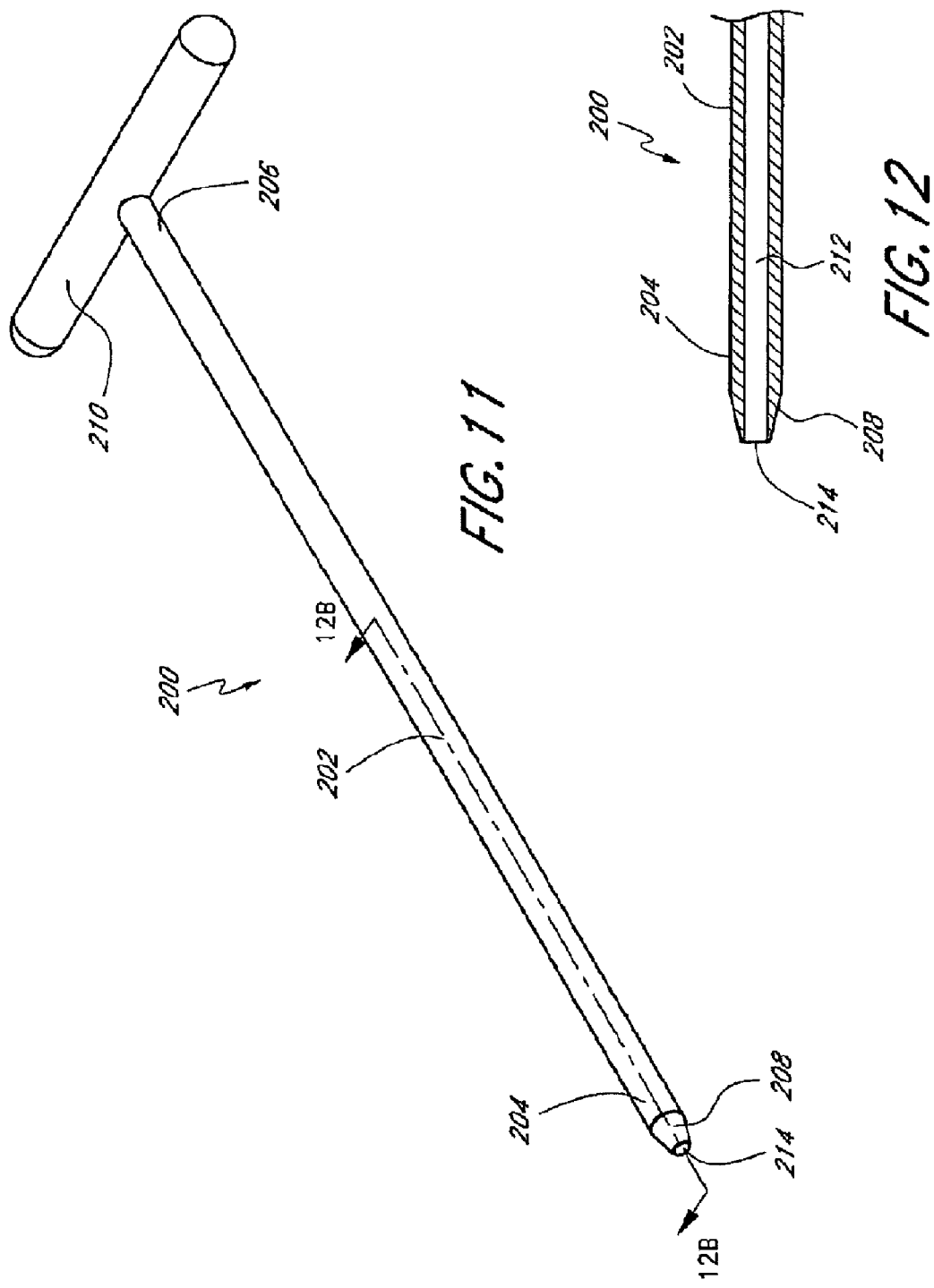
FIG. 11 is a perspective view of one embodiment of a dilator.
Figure 12:
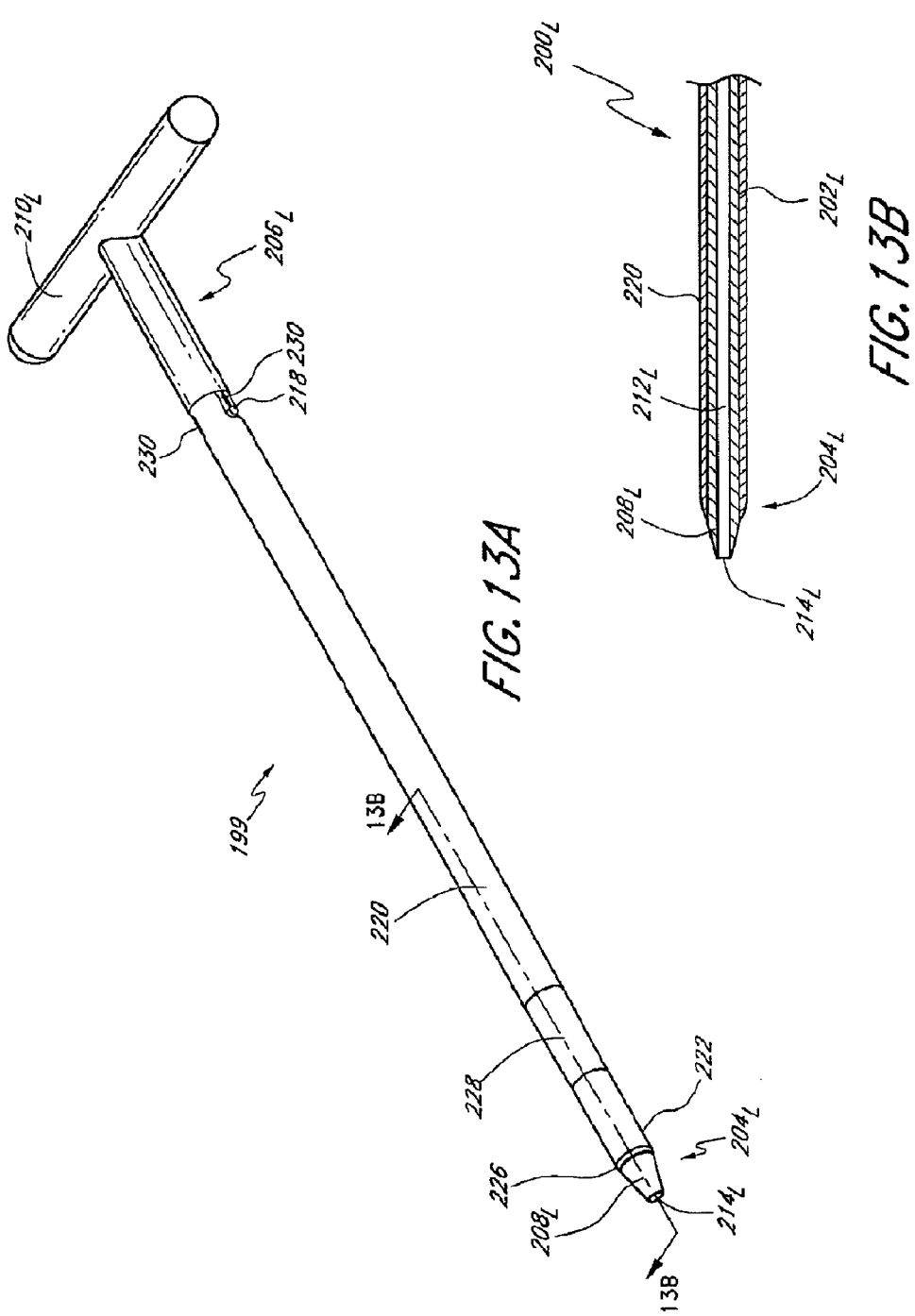
FIG. 12 is a side cross-sectional view of the distal portion of the dilator in FIG. 11.

With reference to FIGS. 11-12, in one embodiment, the dilator 200 comprises a cannulated dilator rod 202 extending between a distal end 204 and a proximal end 206, and defines an inner lumen 212. The dilator 200 comprises a tapered dilator tip 208 with a distal end opening 214 at the distal end 204 and a handle 210 at the proximal end 206.

The length of the cannulated dilator 202 is typically in the range of about 150 mm to about 450 mm, often about 250 mm to about 350 mm. In one exemplary embodiment, the length of the rod 202 is approximately 300 mm (12.00").

Figure 10:
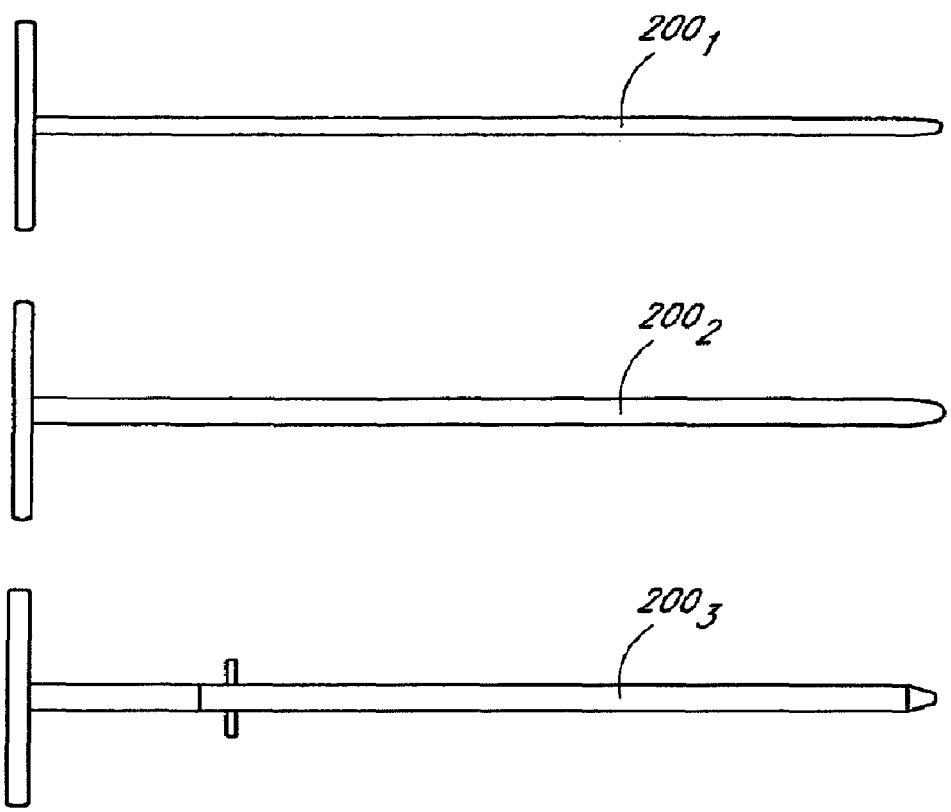
FIG. 10 is an elevated view of three differently sized dilators.

The I.D. of the cannulated dilator rod 202 is typically in the range of about 2.5 mm to about 4.5 mm, often about 3 mm to about 4 mm. In one embodiment, the rod 202 has an I.D. slightly larger than about 3.5 mm (i.e., greater that the O.D. of the extended guide pin 164) and an O.D. of about 6 mm. FIG. 10 illustrates three bone dilators $200_1$, $200_2$, and $200_3$ having O.D. of 6 mm, 8 mm, and 10 mm, respectively.

The tapered dilator tip 208 is usually tapered at about 5 to about 45 degrees from O.D. to I.D. In one embodiment, the tip 208 of the dilator 200 is tapered at approximately 8 degrees from O.D. to I.D. In another embodiment, the tip 208 is tapered at about 13 degrees from O.D. to I.D.

Figure 13:
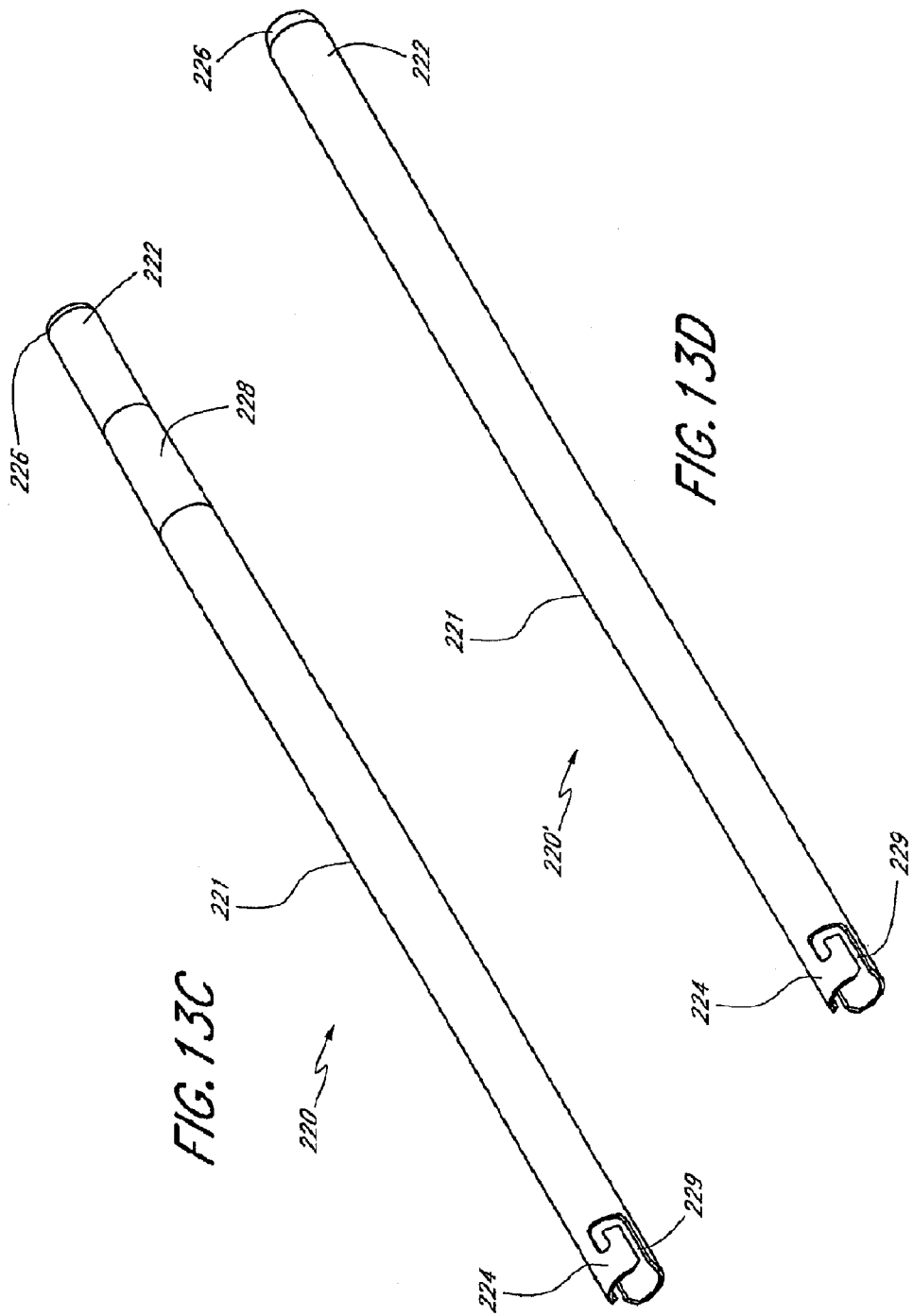
FIG. 13A is a perspective view of one embodiment of a large dilator with a dilator sheath.
FIG. 13B is a side cross-sectional view of a distal portion of the large dilator within the dilator sheath of FIG. 13A.
FIG. 13C is a perspective view of the sheath of the large dilator of FIG. 13A.
FIG. 13D is a perspective view of another embodiment of a large dilator sheath.

The cannulated dilator rods 202 can be made from any known suitable material, such as, for example, stainless steel, aluminum, or composites thereof. In one embodiment, the dilator 200 and its component parts are machined from stainless steel tubing. Here, each dilator 200 has a handle 210 that is affixed to the dilator proximal end 206. The handle 210 is about 100 mm (4.00") long and is engaged (e.g., by welding; press fit, etc) in the middle to assure a secure fit with the rod. With reference to FIGS. 13A-C, in one embodiment, there is provided a large dilator construct 199, configured as a dilator sheath 220 and a dilator rod assembly $200_L$ that comprises a dilator shaft $202_L$ a dilator handle $210_L$, and two pins 218 as engagement means for the construct 199 The cannulated dilator shaft $202_L$ extends between a distal end $204_4$ and a proximal end $206_L$ and defines an inner lumen $212_L$. The shaft $202_L$ comprises a tapered tip $208_L$ with a distal end opening $214_L$ at the distal end $204_L$. The dilator rod assembly $200_L$ comprises pins 218 extending out from the outer wall of the dilator shaft $202_L$.

The length of the cannulated dilator rod assembly $200_L$ is typically in the range of about 8" to about 16", often about 11" to about 13". In one embodiment, length of the dilator rod assembly $200_L$ is approximately 300 mm (12.00"). In one embodiment, the larger diameter proximal end $206_L$ of the dilator shaft $202_L$ is about 75 mm (3") in length while the overall length of the dilator rod assembly $200_L$ is about 300 mm. (12.00").

In one embodiment, the cannulated dilator shaft $202_L$ has two different outer diameters. More specifically, there is a smaller diameter section of the dilator shaft $202_L$ configured to be covered by the sheath 220. The O.Ds. are typically in the range of about 5 mm to about 12 mm, often about 6 mm to about 11 mm. In a preferred embodiment, the dilator shaft $202_L$ has a smaller O.D. of about 9 mm (0.35") and a larger O.D. of about 10 mm. The I.D. of the dilator shaft $202_L$ is typically in the range of about 2.5 mm to about 4.5 mm, often about 3 mm to about 4 mm.

The tapered dilator tip $208_L$ is usually tapered at about 5 to about 45 degrees from O.D. to I.D. In one embodiment, the tip $208_L$ of the dilator shaft $202_L$ is tapered at about 13 degrees from O.D. to I.D. In one preferred embodiment, this taper of tip $208_L$ is substantially the same as the taper of the tip 226 at the distal end 222 of the dilator sheath 220.

The sheath 220 comprises a sheath tube 221 that extends between a distal end 222 and a proximal end 224, and is configured to be releasably attachable to the dilator rod assembly $200_L$. In one embodiment, the sheath tube 221 comprises a tip 226 at the distal end 222 and two tracks (one shown) 229 machined into the wall of the tube 221, that is positioned to begin at the proximal end 224 and extend longitudinally along the sheath tube 221 with a slight circumferential notch at the distal end of the track 229.

The track 229 accepts the pin 218 mounted on the dilator shaft $202_L$, thereby providing a releasable interlock of the dilator shaft $202_L$ with the sheath 220. In another embodiment, the large dilator construct 199 comprises any known suitable releasable lock comprising any of a variety of interference fit or friction fit surfaces carried by the dilator shaft $202_L$ for cooperating with a complementary structure on the sheath 220.

In one embodiment, the large dilator construct 199 comprises two tracks 229 and two locking lugs 218. In another embodiment, the large dilator construct 199 comprises one track 229 and one pin 218.

Both the dilator shaft $202_L$, the sheath 220, and their respective component parts can be made from any known suitable material, such as, for example, stainless steel, aluminum, or composites thereof. The sheath 220 is preferably fabricated from a material of sufficient stiffness to maintain its structural integrity when other access and preparation tools are subsequently introduced and utilized through the sheath cannula.

In one embodiment, the distal end 222 of the sheath 220 is beveled to match the taper of the dilator tip $208_L$ of the large dilator rod assembly $200_L$ (e.g., 10 mm dilator), thereby facilitating insertion of the rod $202_L$ into the sheath 220.

The length of the sheath 220 is typically in the range of about 7" to about 10", often about 8" to about 9". In one embodiment, the sheath 220 is approximately 200 mm (8.5") in length.

The wall thickness of the sheath 220 is typically in the range of about 0.005" to about 0.040", often about 0.008" to about 0.030". In one embodiment, the sheath 220 has an I.D. of about 9 mm (0.35") and an O.D. of about 10.5 mm (0.413").

The actual dimensions of the large dilator rod assembly $200_L$ and its components will depend in part on the nature of the treatment procedure and the anatomical characteristics of the patient. For example, the O.D. is about 9.5 mm (0.375") for a sheath 220 used in treating relatively smaller patients, while the O.D. for the same is about 10.5 mm. (0.413") for relatively larger patients. As shown in FIG. 13C, in one embodiment, there is provided a distal end taper 228 as a transition to enable use of a smaller distal OD dilator sheath 220 (e.g., 0.375") with a sturdier proximal wall thickness, where clinically appropriate. In another embodiment, there is no taper to the distal end of the dilator sheath 220' (FIG. 13D). In another embodiment, the sheath 220, 220' has a beveled tip 226 at the distal end 222, which facilitates docking of the sheath 220, 220' to the targeted site 192, i.e., the anterior surface of the S1 vertebral body.

The large dilator rod assembly $200_L$ is preferably releasably interlocked to the proximal end 224 of the dilator sheath 220 and is preferably capable of being released and removed thereby facilitating the withdrawal of the large dilator rod assembly $200_L$ while leaving the sheath 220 to serve as a working cannula into the targeted site, such as, for example, the anterior surface of the S1 vertebral body.

Figure 9:
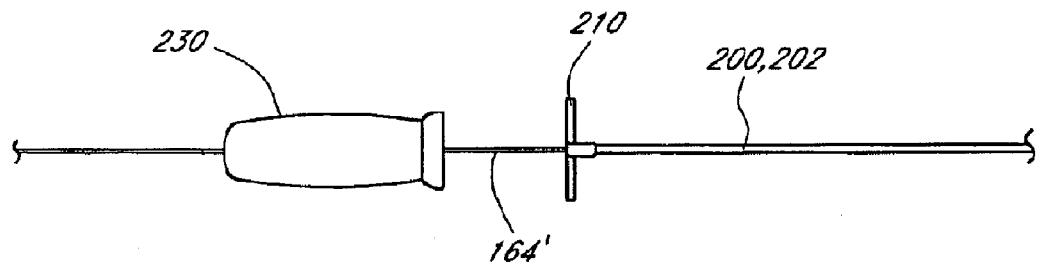
FIG. 9 is a side view of a slap hammer and a dilator handle on an extended guide pin.

With reference to FIG. 9, in one exemplary method of use, the dilator 200 is tapped with a cannulated slap hammer 230 that slides onto the extended guide pin 164. Successive movements distally and proximally over the extended guide pin 164 that repeatedly tap against the dilator handle 210 will to advance the dilator, longitudinally, into the sacrum. In one embodiment (not shown), the hammer 230 has a flat on it to give another hammering surface, as well as for ease of use, where the additional flat prevents the hammer from rolling off of the table.

The use of the slap hammer 230 engaged on the extended guide pin 164, as opposed for example, to the use of an unengaged mallet in "free space" on the proximal end 206 of a dilator 200, enables the surgeon to focus his attention on the visualization monitor while simultaneously tapping and dilating. The axial alignment of the slap hammer 230 resulting from its use in combination with the extended guide pin 164 is advantageous in that it transfers force solely in the longitudinal direction, which precludes misshapen pathways or misalignment of subsequently introduced tools.

In one embodiment, the hammer 230 has a length of about 4" (100 mm). The I.D. of the cannulated hammer 230 is configured to slide over the guide pin. In one exemplary embodiment, the hammer has a lumen ID of about 3.5 mm (0.13"). The cannulated slap hammer 230 can be made from any known suitable material, such as, for example, stainless steel or the like.

With reference to FIG. 10, in one exemplary method of use, a series of bone dilators $200_1$, $200_2$, and $200_3$, having O.D. of 6 mm, 8 mm, and 10 mm, respectively, are advanced directly over the guide wire 164, and tapped with a slap hammer 230 to progressively widen the intervertebral channel in a stepwise manner. The last and largest dilator $200_L$ ($200_3$ in the present embodiment) is assembled with a sheath 220. The dilator $200_L$ can be inserted as a preface to the subsequent introduction of successive instruments in the surgical tools sets described herein. The large dilator sheath 220 is preferably left behind to serve as a protected portal to the target location.

In one embodiment, the dilators and sheaths (e.g., sheath 220) are coated with a surfactant, hydrophilic hydrogel, or the like to facilitate passage of surgical tools and/or implants through the sheath 220. In another embodiment, the surgical tools and/or implants inserted into the sheath 220 are coated with a surfactant, hydrophilic hydrogel, or the like.

In accordance with one aspect of the embodiments described herein, there are provided twist drills that can be used to extend the working channel within the spine, such as, for example, a channel that extends cephalad from the anterior surface of the S1 vertebral body.

Figure 14:
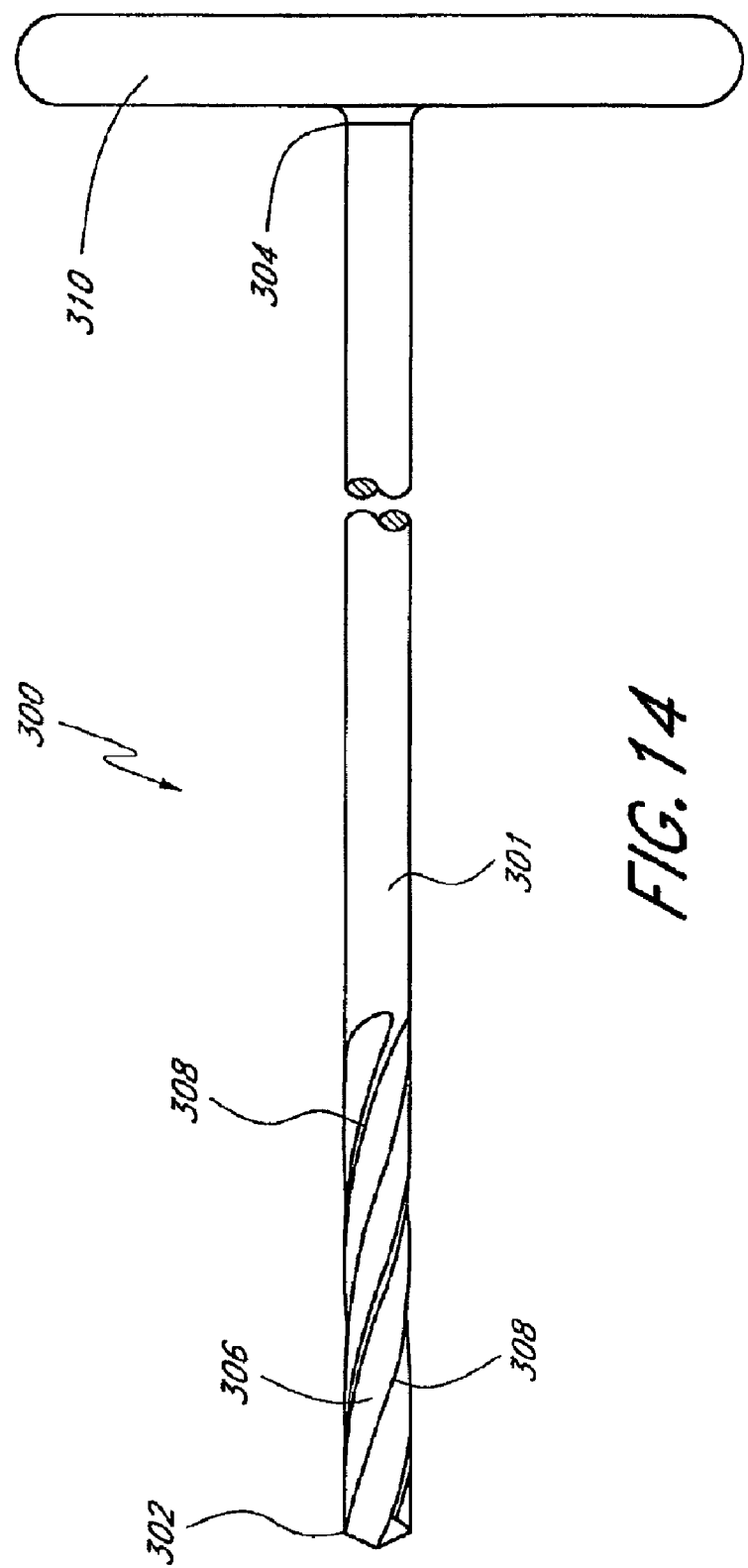
FIG. 14 is a side view of one embodiment of a twist drill.

With reference to FIG. 14, there is provided a twist drill with handle 300. that a configured as a twist drill 301 having a distal end 302 comprising a fluted section 306 with helical flutes 308 and a proximal end 304, and a handle 310 engaged at the proximal end 304 of the twist drill 301. The helical flutes 308 facilitate boring as the handle 310 is turned in the appropriate direction—here, clockwise to advance the twist drill 301 distally into the working channel.

The twist drill with handle 300 is typically fabricated from hardened stainless steel or the like. The length of the twist drill with handle 300 typically ranges from about 11" (275 mm) to about 13" 330 mm. In one embodiment, the twist drill with handle 300 is approximately 300 mm (12.00") long. The twist drill with handle 300 typically ranges in diameter from about 5 mm (0.20") to about 13 mm (0.50"). In one embodiment, the twist drill with handle 300 has a diameter of about 9 mm.

In one mode of use, the twist drill with handle 300 is used to extend the working channel in the spine to the treatment area (e.g., a disc space) after bone dilators are used to expand the diameter of the proximal portion or entry/targeted site 192 of the working channel.

In one exemplary method of use, where the targeted site 192 is the anterior surface of a sacral vertebral body and where the dermal entry site is near the paracoccygeal region, a twist drill with handle 300 having an O.D. of about 9 mm and is inserted into the lumen at the proximal end 224 of the dilator sheaths 220 or 220', each of which is used as a protected portal to the sacrum. The twist drill with handle 300 is advanced by turning the handle 310 at the proximal end 304 of the twist drill 301 so that the helical flutes 308 at the distal end 302 of the twist drill 301 progressively bore into and penetrate through the superior S1 bone end plate and into the L5-S1 disc space. Following nucleectomy and preparation of the disc space by means of the cutters and tissue extraction tools and methods described below, the twist drill with handle 300 can again be used to penetrate the L5 inferior bone end plate and vertebral body, prior to the removal of the dilator sheath 220 or 220', using, for example, a 6 mm or a 7.5 mm twist drill with handle 300 as needed based on the patient's anatomy.

In one mode of use, the twist drill with handle 300 is used to drill about halfway into the depth of the L5 vertebral body in preparation for subsequent anchoring of implants, or through the vertebral body to gain axial access to more distal inter-vertebral disc spaces, e.g., L4-L5, for therapeutic procedures.

In one embodiment, not illustrated, the twist drill unit comprises a bushing portion configured to compensate for the (mismatch) differences between the I.D. of the dilator sheath 220 or 220' and the O.D. of the twist drill with handle 300, thereby precluding "wobble" in the disc space en route to the L5 target, and thus enabling on-center axial alignment and use. The bushing portion is preferably located on the twist drill 301 near the proximal end 304 that is sufficiently distant from the distal end 302 so that it remains within the confines of the dilator sheath 220 or 220' during operation of the tool for its intended purpose. In one embodiment, the bushing portion is made from a polymer, such as, for example, Delrin™, PTFE, PVDF, or the like. In a preferred embodiment the bushing is integral with the twist drill 301, i.e., formed from the same rod blank.

On advantage of the present embodiment is that the twist drill configuration, mode of delivery, and use at the target site are no longer dependent on electrical or motorized drilling, thereby eliminating the risks of tissue damage associated with electric drill slippage and recoil.

In accordance with one aspect of the embodiments described herein, there are provided nucleectomy and cutting tools and techniques having advantages over conventional cutting tools and techniques. Certain conventional procedures rely on brute force to scrape, tear or break away the material. For example, rongeurs, or "pliers-like" devices, are often utilized to reach in through an access hole cut into the annulus, grab an amount of nucleus tissue and then to rip it out. In another example, curettes or various flat blades with sharpened edges are inserted and scrapped against the bone in an attempt to separate the nucleus from the bone. Another conventional approach involves using enzymes, such as, for example, chemopapain, to chemically dissolve or breakdown the nuclear tissue. Such conventional approaches and techniques are often inexact, incomplete and potentially dangerous to the patient. Often the extent of the surgical exposure, and therefore the resulting trauma, is dictated by the nucleus removal procedure and not the subsequent fusion or repair procedure, which is the true end goal of the procedure. In contrast to the conventional techniques, methods, and instrumentation described above, the apparatuses and methods described herein are not reliant on the application of strength and high forces and are designed be more effective in complete removal of tissue and clean preparation of any bone surfaces.

Co-pending U.S. patent application Ser. No. 10/853,476, filed May 25, 2004, teaches various types of instrumentation and techniques for the removal of tissues and preparation of treatment sites in the spine, such as, for example, inter-vertebral motion segments located within the lumbar and sacral regions.

With respect to the present invention, it is anticipated that one or more nucleectomies can be performed extending into successively cephalad intervertebral disc spaces. For example, a disc recess 354' is depicted in disc L4-L5 A wide variety of cutter blade and edge configurations as bore enlarging means can be employed to perform nucleectomies of the L5-S1 354, and L4-L5 354' disc spaces, wherein the cutter means are delivered and operated through the anterior TASII axial bore(s). Certain of these methods are described in further detail in U.S. patent application Ser. No. 09/710,369, the content of which is incorporated in its entirety into this disclosure by reference.

Co-pending U.S. patent application Ser. No. 09/782,534, filed on Feb. 13, 2001, teaches various types of techniques for using cutting tools for removing disc material and preparation of spinal treatment sites that comprise a spinal disc, for example, a method of removing at least a portion of the nucleus through a TASII axial bore while leaving the annulus AF intact.

Figure 15:
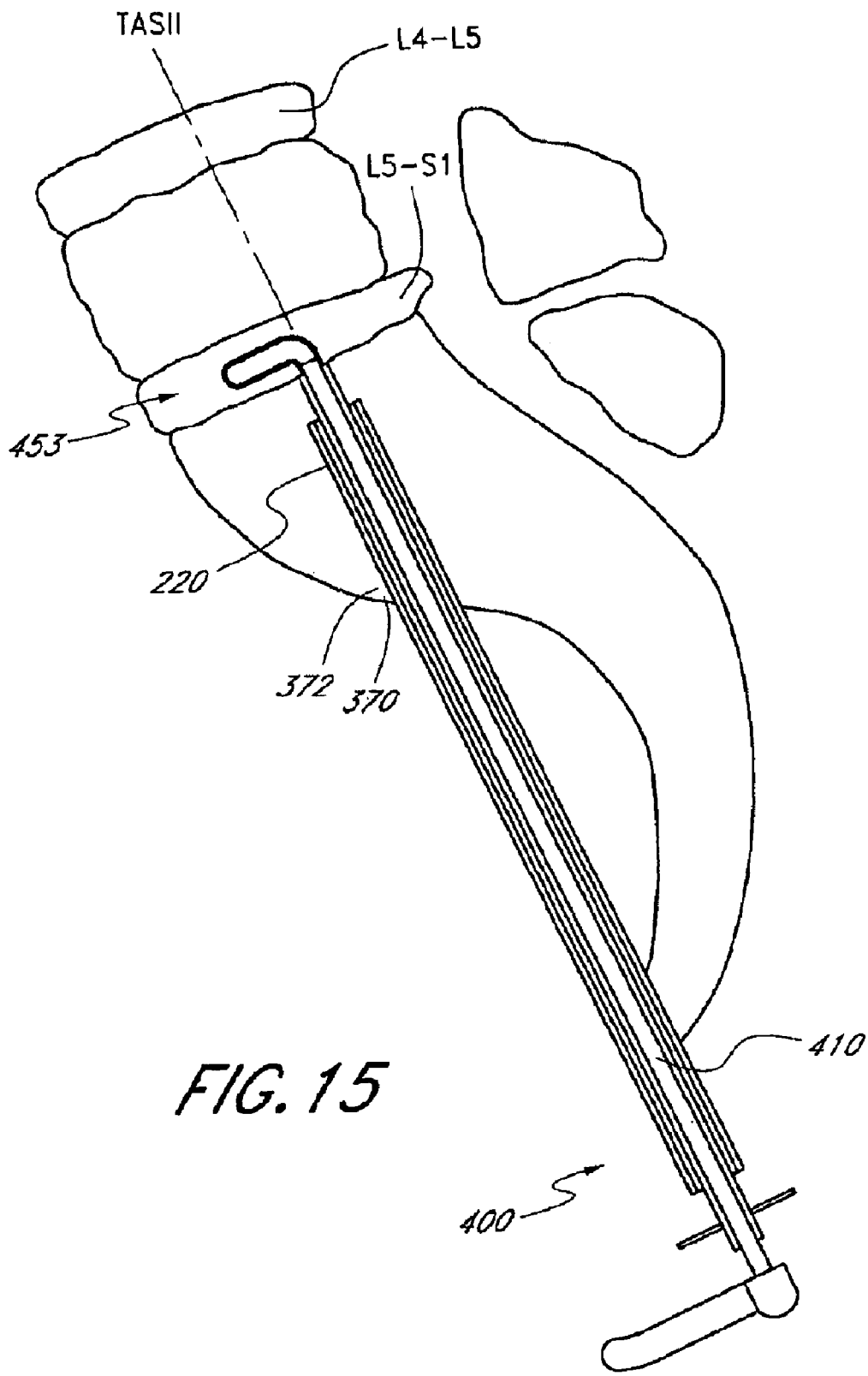
FIG. 15 shows a cutter extending through a dilator sheath (docking cannula) in the L5-S1 disc space.

Referring to FIG. 15, a nucleectomy instrument 400 is inserted through the axially aligned anterior tract 372 defined by the lumen of the dilator sheath 220 and the TASII axial bore 370. The nucleectomy instrument 400 comprises a cutting blade (e.g., cutter blade 453 which refers collectively to any blade configuration) which is remotely manipulatable, i.e., a retracted cutter blade 453 is first advanced through the TASII axial bore 370 and then extended laterally into the nucleus of the spinal disc. More specifically, the cutting blade 453 is mounted into an extendible or steerable distal end section 382 of nucleectomy instrument, i.e. cutter assembly 400 extending through the TASII axial bore 370 and anterior tract 372.

The cutter assembly 400, cutter blade 454 and cutter assembly shaft 410 are shown schematically in FIGS. 16-18 and not necessarily to scale to one another or to the TASII axial bore 370.

In accordance with one aspect of the embodiments described herein, there are provided surgical cutters that can be used to perform nucleectomy via insertion into a disc space to excise, fragment and otherwise loosen nucleus pulposus and cartilage from endplates from within the disc cavity and from inferior and superior bone end plate surfaces. The cutters described herein represent a significant advance to current clinical techniques for access and preparation of intervertebral bodies for the subsequent insertion of therapeutic devices, such as prosthetic nucleus and fusion implants, and in particular for axially aligned implants, or for insertion of therapeutic materials, e.g., for osteogenesis, spinal arthroplasty, or annuloplasty.

Figures 16A, 16B:
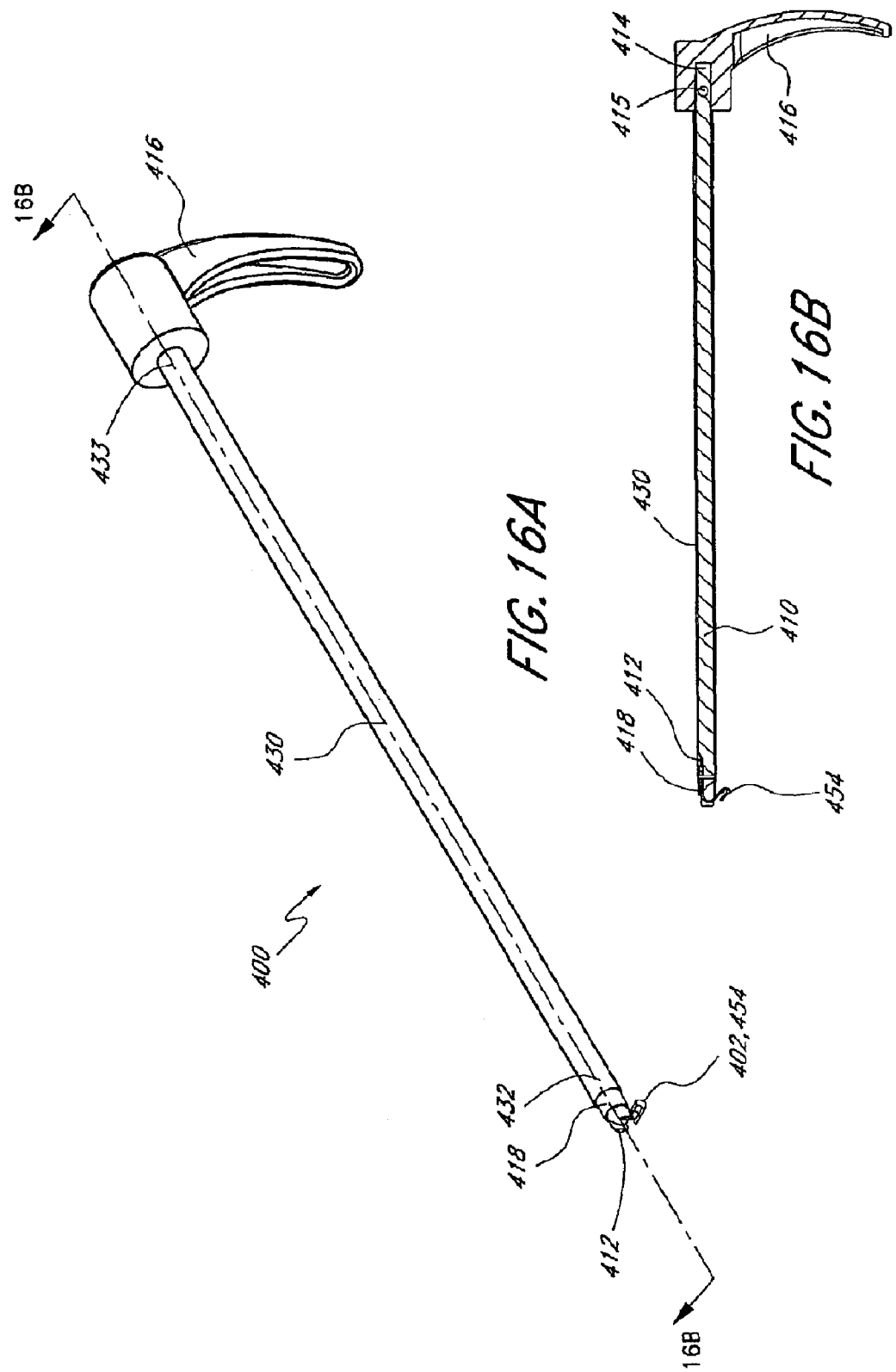
FIG. 16A is a perspective view of one embodiment of a cutter assembly that comprises a down-cutter.
FIG. 16B is a side cross-sectional view of the cutter assembly of FIG. 16A.
Figure 16C:
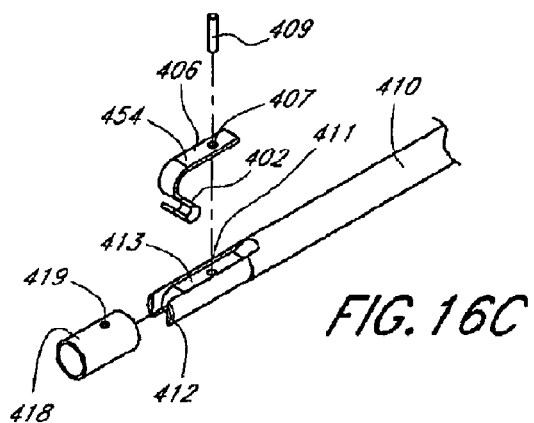
FIG. 16C is an exploded, perspective view of the distal portion of the cutter assembly of FIG. 16A.

With reference to the exemplary embodiments of FIGS. 16A-C, the cutter assembly 400 comprises: a cutter shaft 410 extending between a distal end 412 and a proximal end 414; a cutter blade 453 at the distal end 412; a handle 416 at the proximal end 414; a cutter sheath 430 placed concentrically over the shaft 410; and a shaft sleeve 418 at the distal end 412.

It will be understood, however, that the cutter components and structures described herein are suitable for the assembly and application of cutter assemblies that comprise, for example, up-cutters 452, debulkers 450, down-cutters 454, or the like, or variations thereof. In FIGS. 16A-16E, the cutter comprises a down-cutter 454. In another embodiment, the cutter comprises an up-cutter 452 (see FIG. 16H) In still another embodiment, the cutter comprises a debulker 450 (see FIGS. 17A-E). These and other types of cutters are described in further detail below, with reference to preferred embodiments which comprise teardrop-shaped cutter blades 460, 460', 490, 490', 490" shown in FIGS. 18A-18G.

Figure 17A:
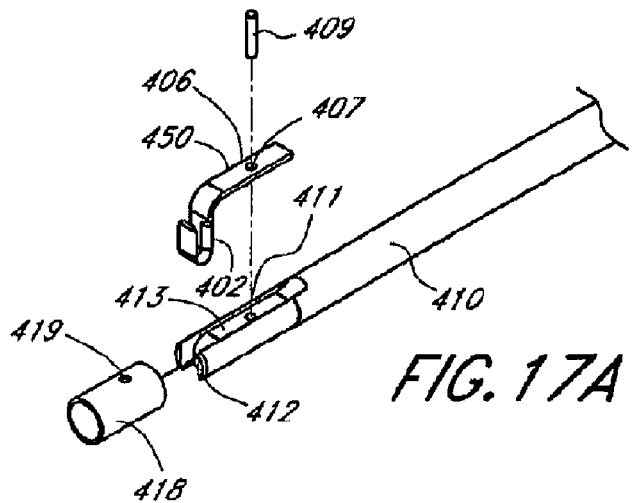
FIG. 17A is an exploded, perspective view of the distal portion of a cutter assembly that comprises a debulker.

With reference to the embodiments of FIGS. 16C and 17A, in assembling the cutter assembly 400, the longitudinal portion 406 of the cutter blade (e.g., debulker 450, up-cutter 452, or down-cutter 454) is placed into a slot 413 near the distal end 412 of the shaft 410. In one embodiment, the cutter blade hole 407 is aligned with a strategically placed cutter shaft hole 411 within the shaft slot 413.

The shaft slot 413 is dimensioned to accommodate a cutter blade 453, such as, for example, a debulker 450 (17A), an up-cutter 452, a down-cutter 454 (16C), or the like, or variations thereof. The width of the slot 413 is approximately the same as the width of the longitudinal portion 406 of the cutter blade 453. The curvature at the distal end of the slot 413 accommodates the curvature of the cutter blade 453 between the longitudinal portion 406 and the laterally extending portion of the blade arm 402 (which defines the reach or throw of the cutter blade 453). The slot 413 provides torsional support to the cutter blade arm 402 while the curvature at the distal end of the slot 413 provides axial support to the cutter blade arm 402, necessary, in conjunction with cutter blade edge geometries (described in detail below; see FIGS. 16D-6H and 17B-17E, and 18A-18F) to the cutting effectiveness of the cutter blade 453.

A shaft sleeve 418 may be placed over the assembly shown in FIGS. 16C and 17A comprising the shaft 410 and the cutter blade 453. The shaft sleeve 418 when pinned effectively serves to align and fix the shaft 410 and the longitudinal portion 406 of the cutter blade 453. While any of variety of other fastening techniques may also be used, the preferred pin technique is described below.

In one embodiment, the shaft sleeve 418 comprises a strategically placed shaft sleeve hole 419 that aligns with the cutter shaft hole 411 of the shaft slot 413 and the cutter blade hole 407. The sleeve 418 can be securely fixed to the rest of the assembly by inserting a cross pin 409 through the shaft sleeve 418 and the longitudinal portion 406 of the cutter blade 453 into the shaft 410. In one embodiment, the cross pin 409 that fixes the cutter blade 453 to the shaft 410 is approximately 0.06" in diameter. The rest of the assembly 400 components can be fixedly secured to each other using any known suitable fixation mechanisms, as described in further detail below.

Figure 16D:
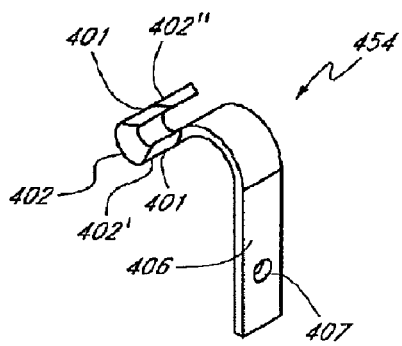
FIGS. 16D and 16E are elevated views of one embodiment of a small down-cutter.
Figure 16E:
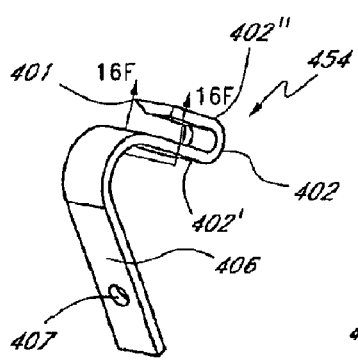

With reference to an exemplary embodiment in FIGS. 16D-E, the cutter blade 453 (as shown, a down-cutter 454) comprises a blade arm 402 and a longitudinally-extending portion 406. The blade arm 402 begins from the proximally-located, longitudinally-extending portion 406, and extends laterally to comprise any number of suitable shapes or configurations, such as, for example, a "J" shape or "S" shape, as shown. It is understood that in the context of the present invention, configurations of the types as just described may comprise a plurality of cutter blade arms 402. In a preferred embodiment, described in further detail below, the cutter blade 453 comprises a "teardrop" shape (460, 460', 490, 490', 490") shown in FIGS. 18A-18G.

The cutter blades 453 generally comprise at least one sharpened cutter blade edge 401 (collective). With reference to FIGS. 16D-E, in one embodiment, the cutter blade arms 402 (collective) of the down-cutters 454 have three cutter blade edges 401 including cutter blade arms 402' (proximal), and 402" (distal) separated lateral bend 403. In other words, the cutter blade edges may be continuous with each other around the lateral bend 403 or may be interrupted. The illustrated blade edges 401 are illustrated on a leading surface 405 of the cutter blade arm 402. A trailing surface 415 is illustrated as a blunt side, without a sharpened cutter blade edge 401. Since the cutter blade edges 401 are on the same (leading) edge or side of the cutter blade arms 402, the cutter blade 454 is considered to be single-sided in this regard. In this embodiment, the single-sided cutter blade arms 402 cut when turned in a clockwise manner but do not cut when rotated in a counter-clockwise direction. The direction of the rotation (clockwise or counterclockwise) is determined from a perspective that is proximal relative to the distally-located cutter. In another embodiment, not illustrated, the cutter blade arms 402 have cutter blade edges 401 on both the leading surface 405 and trailing surface 415 of the cutter blade arms 402, so that cutting can be accomplished with this double-sided cutter blade arms 402 by means of either clockwise or counterclockwise rotation.

As will be described in further detail below, all of the cutter blade edges 401 disclosed herein may be optimally configured for preparing an intervertebral motion segment for either a subsequent fusion procedure or a subsequent procedure in which mobility of the intervertebral motion is to be preserved. More specifically, for nucleectomies preceding fusion procedures, cutter blade edges 401—regardless of cutter blade arm 402 configuration—will contact the spinal disc inferior or superior endplates, while for mobility procedures, the cutter blade edges 401 will be spaced apart from the spinal disc endplates.

Figure 16F:
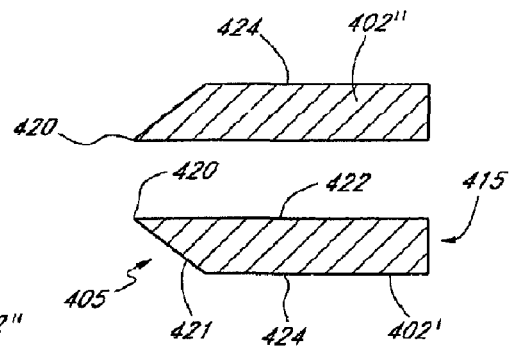
FIG. 16F is a cross sectional view of a proximal cutter blade arm (402') for nucleectomy prior to a mobility preservation procedure taken along the line 16F-16F in FIG. 16E.
Figure 16G:
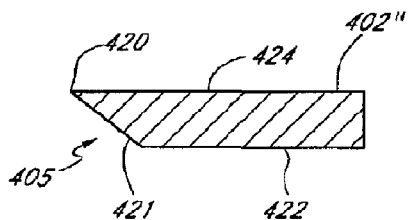
FIG. 16G is a cross sectional view of a proximal cutter blade arm (402') for nucleectomy prior to a fusion procedure taken along the line 16F-16F in FIG. 16E. The inclined plane (421) is a mirror image of that in of FIG. 16F.

As an example. referring to FIG. 16G, there is illustrated a cross-sectional view through cutter blade arm 402 of the cutter blade 454 illustrated in FIG. 16E. In that illustrated embodiment, a leading side 405 is provided with a sharpened edge 420 fabricated by means of cutting, grinding or other manufacturing technique. The sharpened edge 420 is formed at the intersection of the declined face 421 and the surface 424 of the cutter blade arm 402' and 402". This cutter blade 454 configuration is optimized for use against an inferior endplate in preparation for a fusion procedure. When the proximal surface 424 is placed in contact with an inferior endplate of a spinal disc and rotated in a clockwise direction, the sharpened edge 420 on leading surface 405 will scrape against said endplate. This can be used to scrape away the cartilaginous endplate and roughen the vascularized vertebral body so as to cause bleeding, which is desirable in order to facilitate bone growth and achieve fusion of the vertebral bodies that are superior and inferior to the spinal disc being treated However, in a procedure to prepare the nucleus space for implantation of a mobility preserving device, roughening the endplate of the spinal disc may be undesirable. As shown in FIG. 16F, for this procedure, the sharpened edge 420' is desirably positioned at the intersection of the inclined face 421 and the surface 424, such as by mirroring the angle of inclination of the declined face 421. In this configuration, the sharpened edge 420' will be spaced apart from the inferior endplate of the spinal disc by a distance which is equal to the thickness of the proximal cutter blade arm 402', thereby minimizing the chance of the bone bleeding, that would promote unwanted fusion.

With respect to the cutter arm blade 402, the mirrored blade of proximal cutter blade arm 402' is shown in FIG. 16F and FIG. 16G as distal cutter blade arm 402".

A sharpened edge (not shown) may alternatively be positioned partway between the proximal surface 422 and the distal surface 424, such as providing a first and second inclined face on the leading surface 405, which intersect at a sharpened edge 420. In the atraumatic cutter design, intended for use in preparation for a procedure which preserves mobility, the sharpened edge 420 is preferably spaced apart from the surface of the cutter adapted for sliding contact with a boney end plate. Although the sharpened edge 420 may optimally be spaced apart from the bone contacting surface by the full thickness of the cutter blade, as discussed above, a sharpened edge 420 may be positioned in-between the proximal surface 422 and the distal surface 424 by a sufficient distance to prevent injury to the bone. The distal and proximal orientation of the sharpened edge 420 described above may be mirrored on a given cutter blade, depending upon whether the cutter is intended to be placed in sliding contact with an inferior or superior spinal disc endplate, as will be apparent to those of skill in the art in view of the disclosure herein. Again, the foregoing sharpened edge orientation may be applied to any of the cutter configurations disclosed herein.

Figure 16H:
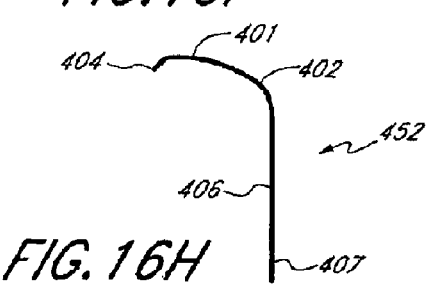
FIG. 16H illustrates one embodiment of an upcutter (452).

In one embodiment, shown in FIG. 16H, the cutter of the assembly 400 comprises an up-cutter blade 452. As with the above-described down-cutter blade 454, the up-cutter blade 452 generally comprises a cutter blade arm 402 and a longitudinally extending base portion 406. The cutter blade arm 402 begins from a proximally located, longitudinally extending base portion 406 that extends generally distally and inclines laterally outwardly to a radial limit 404. The arm 402 curves to form a proximally facing concavity with a distal limit. The cutter may comprise any number of suitable shapes or configurations, such as, for example, a "J" or question mark shape. In another embodiment, described below, the cutter comprises a "teardrop" shape.

With reference to the embodiments shown in FIGS. 16D-H, the down-cutters 454 and up-cutters 452 have single-sided blade arms 402 that are bent at an angle from between about 40 degrees to about 140 degrees relative to the longitudinally extending portion 406. The blade arms 402 can optionally be canted between about 5 to about 25 degrees, preferably about 15 degrees, so that the cutting edge is rotated radially outwardly relative to the trailing edge. The blades arms 402 of the up-cutters 452 and down-cutters 454 are preferably angled vertically steeper relative to the longitudinal axes of the shafts to which they are affixed, as compared to those of debulkers 450, described in further detail below.

The tilt of the blade arm 402 in the proximal direction in FIGS. 16D, 16E and 16H is configured to allow for maximum engagement of the blade cutting edge with the distally facing surface of the bone end plate, while severing nucleus material. Thus, for an up-cutter 452, an angle less than about 90 degrees relative to the axis of the shaft 410 generally would not enable adequate engagement of the blade cutting edge(s) 401 with the superior bone end plate. For a down-cutter 454, an angle greater than about 90 degrees relative to the axis of the shaft 410 generally would not facilitate adequate engagement of the blade cutting edge with the inferior bone end plate, and a blade arm 402 at about a 40 degree angle of tilt of the blade arm 402 operates preferably (is "vertically steeper") than one at 70 degrees.

The "throw" i.e., the reach of the blade arm 402 is measured from the central longitudinal axis of the cutter shaft 410 radially outward to its radial limit 404 (FIG. 16H). In other words, blade arm throw as used herein refers to the radius of the circle cut by a full revolution of the blade arm.

For up-cutters 452 and down-cutters 454, the blade arm 402 throw are generally within the range of from about 6 mm to about 18 mm. In one embodiment, the blade arm throw of the cutters 452, 454 are about 12 mm.

In accordance with one aspect of the embodiments described herein, the cutter blade of the assembly 400 comprises a debulker 450 Up-cutters 452 and down-cutters 454, as illustrated in FIGS. 16D, 16E and 16H may not be ideal initiators of nucleus tissue fragmentation. For one, their blade arms 402 and cutting edges 401 do not easily bend or sweep without space, particularly in terms of angles, having first been created by one or more debulkers 450.

With reference to FIGS. 17B-E, a debulker 450 comprises a cutter blade arm 402 that begins from a proximally-located, longitudinally-extending base portion 406 and extends laterally to comprise any number of suitable shapes or configurations, such as, for example, a "J" or "U" shape, as shown.

Figure 17B:
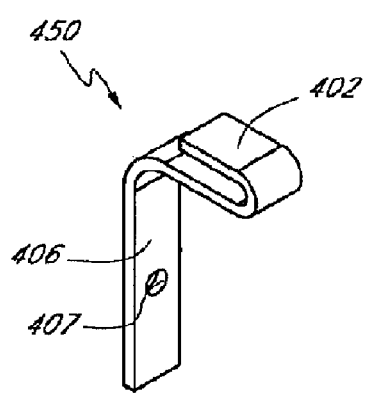
FIGS. 17B-17C are elevated views of the debulker of the cutter assembly of FIG. 17A.
Figure 17C:
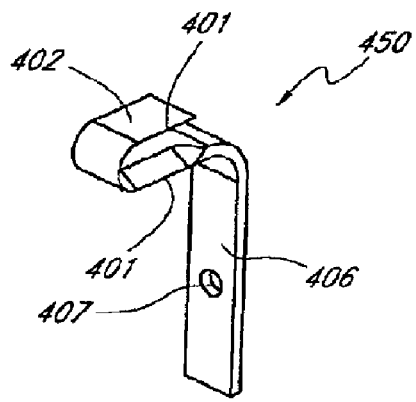
Figure 17D:
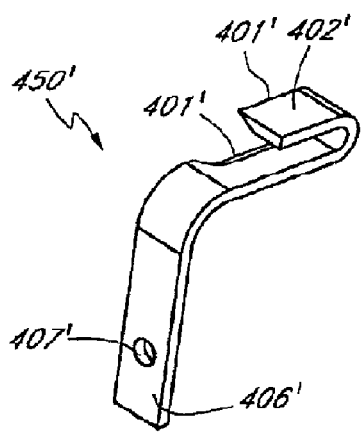
FIGS. 17D-17E are elevated views of one embodiment of a large debulker.
Figure 17E:
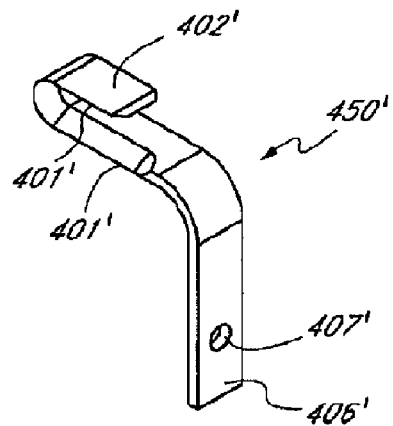

In one embodiment, the debulker 450 comprises a shorter throw than the cutter blade 454, which allows debulkers 450 to retain their shape better than cutters with longer arms upon initial entry into the disc space, providing improved engagement of effective cutting edge surface with nucleus material. FIGS. 17B-C illustrated one embodiment of a relatively smaller sized debulker 450. FIGS. 17D-E show one embodiment of a debulker 450' having a greater cutting radius.

In one embodiment, the blade arm 402 configuration of a debulker 450 resembles a "J" in shape. The functional advantage of such blade vertical elements in the "J" shape is the increased efficiency of cutting per unit of throw or the increased cutting edge surface contact with the material to be fragmented.

In the embodiments of FIGS. 17B-C and 17D-E, the debulkers 450, 450' have single-sided blades (i.e., cutter blade edges 401 on one of the cutter lateral sides). In another embodiment, not illustrated, the debulkers 450 have double-sided blades (i.e., blade edges on both of the cutter lateral edges), which enables bi-directional cutting when the cutter handle 416 is manipulated to rotate the blade arm 402.

In one mode of operation, debulkers 500 with shorter arm lengths, and hence shorter "throws" in terms of circumferential cutting diameter, are first introduced through the large dilator sheath 220 into the disc space and used to fragment the tissue within the disc space. In one mode of operation, one or more down-cutters, up-cutters, or the like, or variations thereof are used to further fragment the tissue within the disc space.

In accordance with one aspect of the embodiments described herein, there are provided cutters that comprise a closed loop such as a "teardrop" shape configuration, which provides more cutter rigidity and reduces the risk of fracture of the cutters during use (e.g., when a leading cutting edge of the cutter becomes embedded in bone during use). It will be understood that the any of the cutters (e.g., down-cutters, up-cutters, debulkers) described herein can comprise a "teardrop" or other closed loop shape.

Cutters (e.g., debulkers, up-cutters, down-cutters, etc.) that comprise a closed loop generally provide a more robust and overall more efficient cutting device that can be used for any number of surgical procedures, such as, for example, nucleectomy. Closed loop cutters may have a variety of advantages over cutters having only a single attachment point to the rotatable support. For example, in one embodiment, the closed loop shape allows for two fully supported cutting edges (e.g., top and bottom) on any given lateral side of the cutter. The closed loop shape also allows for side or end edges in the curve where the blade or cutter arm doubles back on itself.

With reference to embodiment shown in FIGS. 18A-B, there is provided a standard size closed loop debulker 460. In the illustrated embodiment, the cutter arm 462 of the closed loop debulker 460 doubles back upon itself to form a distal segment 470 and a proximal segment 468. Both the distal segment 470 and proximal segment 468 are secured to the rotatable shaft 410, resulting in the distribution of any stress in the arm 462 over two segments rather than over a single segment arm. The distributed stress can result from the torque of turning the shaft 410 or the resistance of the disc material on the blade(s) 461.

The arm 462 of the closed loop cutter begins from a proximally located end 480, extends distally to provide an attachment surface and then laterally outward to form the lower segment 468. The arm 462 then doubles back at juncture 482, the location of which defines the cutting radius. The arm 462 then extends laterally inward, turns, and then proximally toward proximal end 484, to provide an attachment surface. The proximal and distal segments 468, 470 each comprise a sharp edge 461.

The distal segment 470 comprises an attachment structure such as a slot 472 near the proximally located end 484. The lower segment 468 also comprises an attachment structure such as a cutter blade hole 467 near the proximally located end 480. The shaft slot 472 enables end 470 to slide relative to the cross pin 409 during extension and retraction of the cutter blade (e.g., 460 or 490) of the assembly 400.

With reference to the embodiment shown in FIGS. 18C-D, there is provided a large teardrop shaped debulker 460', having a longer laterally extending portion and longer blades 461', relative to the debulker 460 of FIGS. 18A-B. A longer teardrop configuration generally allows for further reach than smaller ones. In general, the cutter blades 460, 460', 490, 490' of FIG. 18A-FIG. 18D, when rotated through a complete revolution will cut a transversely circular cavity having a diameter within the range of from about 10 mm to about 30 mm, In each of the closed loop cutters illustrated in FIGS. 18A through 18D, the proximal segment 468, 468' and distal segment 470, 470' extend radially outwardly from the axis of rotation generally in parallel with each other. However, alternative configurations may also be used, such as by imparting curvature to one or both of the proximal segment 468 and distal segment 470. One or both of the segments may be provided with a curve having a concavity facing in the distal direction; a concavity facing in the proximal direction, or concavities opposite to each other, depending upon the desired clinical result. In addition, in the illustrated embodiments, the cutter blade arm 462 formed by the proximal segment 468 and distal segment 470 extends radially outwardly at approximately a 90 degree angle from the longitudinal axis of the rotatable shaft 410. The cutter blade arm 462 may alternatively be inclined in either a proximal or distal direction (not shown) depending upon the desired performance, and, for example, whether the cutter is intended to operate against an inferior or superior spinal disc endplate. For example, the cutter blade arm 462 may incline in a distal direction or a proximal direction by as much as 45 degrees away from the perpendicular With reference to the embodiments shown in FIGS. 18E, 18F, and 18G, there are provided teardrop shaped down-cutters 490, 490', 490" having large, medium, and small sizes, respectively. The length of the teardrop shaped cutters varies in the range between about 0.25" to about 1.00". These arcuate cutters can extend linearly within a deployment sheath and "curve" as they are advanced distally out of the sheath into the disc space, instead of extending axially until fully deployed from the sheath and then "flopping over" which requires a lateral advance through the nucleus material as well as sufficient axial clearance to allow deployment within the disc. Due to the limited disc height in most fusion/mobility patients, the cutter preferably has a low profile during extension, use, and retraction. Straight bladed cutters will extend linearly in the axial direction of the deployment sheath during extension and long versions may actually hit the upper endplate, causing the cutter to get stuck or inhibiting complete deployment.

With reference to the exemplary embodiment of FIG. 18E, the double-back structure of the teardrop down-cutter 490 begins from a proximally located end 480, extends distally along the lower segment 468, extends laterally outward and downward (i.e., proximally) to form a proximally facing concavity, along the lower segment 468, doubles back at juncture 482, extends laterally inward and upward (i.e., distally), and then extends proximally along the upper segment 470 toward proximally located end 484. At least one and preferably both of lower and upper segments 468, 470 comprise a blade 461.

The upper segment 470 comprises a slot 472 near the proximally located end 484. The lower segment 468 comprises a cutter blade hole (not shown) near the proximally located 480. The shaft slot 472 enables end 484 to slide relative to the cross pin 409 during extension and retraction of the cutter blade (e.g., 490, 490', 490") of the assembly 400.

In the embodiments illustrated in FIGS. 18E through 18G, the separation distance between the first and second cutting edges is a controllable variable in manufacturing (e.g., predetermined during cutter blade formation, i.e., heat treatment of the pinned Nitinol shape memory alloy) and varies from about 2 mm to about 8 mm, and, often is about 3 mm to about 4 mm. The maximum separation 483 in the illustrated embodiment is located within about the radially outwardly most one third of the total blade length. Alternatively, the maximum separation 483 may be positioned within the radially inwardly most third of the blade length, or within a central region of the blade length, depending upon the desired deployment and cutting characteristics.

In accordance with one aspect of the embodiments described herein, the blade arms 402 and the cutter blades 453 in general can be formed from strip material that is preferably a shape memory alloy in its austenitic phase at room and body temperature and that ranges in width from about 0.10-0.20" and in thickness from about 0.015-0.050". Blade arms 402 formed in accordance with the present embodiment are generally able to be flexed in excess of 100 cycles without significant shape loss, and twisted more than 1 and ½ full turns (about 540 degrees) without breakage.

In one embodiment, the cutting blade 453 and cutter blade edge 401 is formed from a super-elastic, shape memory metal alloy that preferably exhibits biocompatibility and substantial shape recovery when strained to 12%. One known suitable material that approximates the preferred biomechanical specifications for cutter blades 453 and cutter blade edges 401 and blade arms 402 is an alloy of nickel and titanium (e.g., $Ni_{56}$—$Ti_{45}$ and other alloying elements, by weight), such as, for example, Nitinol strip material #SE508, available from Nitinol Devices and Components, Inc. in Fremont, Calif. This material exhibits substantially full shape recovery (i.e., recovered elongation when strained from about 6%-10%, which is a factor of ten better than the recovered elongation at these strain levels of stainless steel).

The shape and length of the formed cutter blade 453 in general varies for the different cutting modes. The shape memory material can be formed into the desired cutter blade 453 configuration by means of pinning alloy material to a special forming fixture, followed by a heat-set, time-temperature process, as follows: placing the Nitinol strip (with the blade's cutting edge(s) 401 already ground) into the forming fixture and secured with bolts; and placing the entire fixture into the oven at a temperature ranging from about 500° C. to about 550° C. (e.g., where optimum temperature for one fixture is about 525° C.) for a time ranging from between about 15 to about 40 minutes (e.g., where the optimum time for one fixture is about 20 minutes). Flexible cutter blades formed from Nitinol in this manner are particularly suited for retraction into a shaft sleeve, and are able to be extended to a right angle into the disc space. Moreover, they are able to mechanically withstand a large number of cutting "cycles" before failure would occur.

The cutting blade edges 401 are preferably ground with accuracy and reproducibly. The angle of the inclined surface (e.g., 421, 421', 461, 461'. 461") of the blade relative to the blades's flat side surface typically ranges from about 5 degrees to about 60 degrees, often about 20 degrees to about 40 degrees. In one embodiment, the blade angle is approximately 30 degrees relative to the blade's side surface.

In one embodiment, the shaft 410 of the assembly 400 is formed from solid stainless steel or other known suitable material. In one embodiment, the shaft has a diameter of approximately 0.25" (6.3 mm). The shaft sleeve 418 may be formed from stainless steel tubing or other known suitable material tubing, and has a length of about 0.7".

Figure 16I:
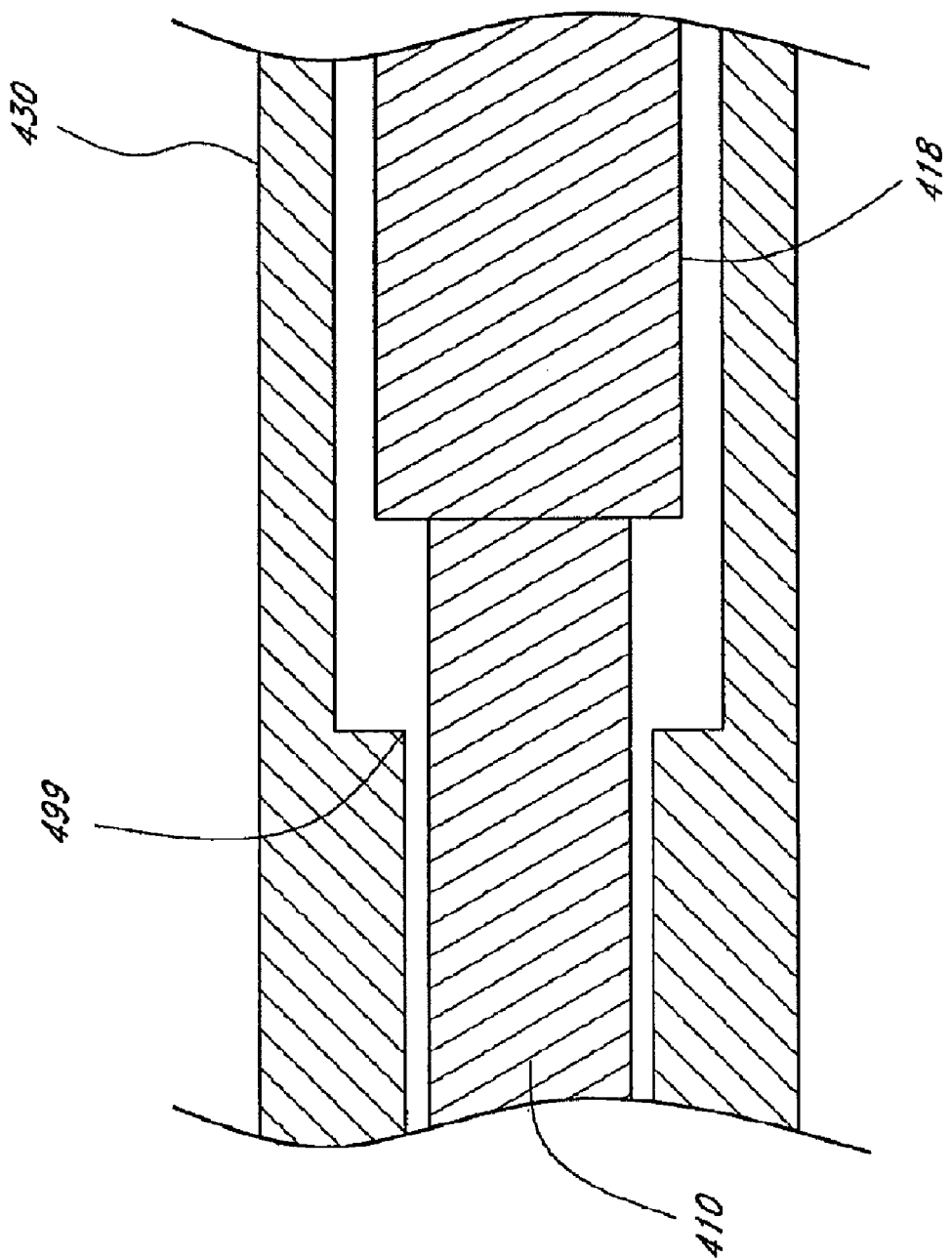
FIG. 16I is a cross sectional view of a distal sleeve-shaft configuration showing a retraction stop mechanism for both a tissue cutter.

The cutter sheath 430 can be fabricated from polymeric material, stainless steel, or other metal tubing. The sheath 430 typically has an outer diameter (O.D.) of about 0.31" (7 mm) to about 0.35" (9 mm). With reference to FIG. 16I, in a preferred embodiment, the sheath 430 is configured with a shoulder 499 bored into its inner wall which serves as a stop that precludes the shaft 410, along with its attached blade arm 402 and handle 416, from becoming fully disengaged from the cutter sheath 430 when the blade arm 402 is retracted into the sheath 430. When retracted proximally, the proximal end of the shaft sleeve 418 bumps into the shoulder 499, thereby preventing the shaft 410 from being fully disengaged from the sheath 430. It will be understood that one or more analogous shoulder structures can be implemented in any of the tools described herein, such as, for example, the sheaths used with the tissue extractors, etc.

In accordance with one aspect of the embodiments described herein, there is provided a handle configured as a lever which is affixed to the proximal end of the cutter shaft. Referring to FIGS. 16A-B, the illustrated handle 416 is affixed to the proximal end 414 of the cutter shaft by means of a cross-pin set screw 415, which reduces the risk of handle 416 disengagement from the cutter shaft 410 (e.g., unthreading by rotational manipulation during cutting). The handle 416 is preferably affixed so that it is in rotational positional alignment with the blade arm 402 and serves as a reference marker for the blade arm's in situ orientation.

In one embodiment, the handle 416 of the cutter assembly 400 is configured as a turn knob fabricated from a polymeric material, such as, for example, ABS polymer or the like, that is injection moldable and that may be machined, and is affixed to the cutter shaft 410 by means of threaded or other engagement to the cutter shaft proximal end 414.

The handle 416 may serve as a stop against which the proximal end of the cutter sheath 430 abuts, thereby maintaining the engagement of the shaft 410 and cutter sheath 430, when the blade arm 402 is extended distally and is exposed from the distal end of the cutter tube lumen, for example, as a result of having pushed on the handle 416 to advance the shaft 410 distally to expose the cutter blade 453 and cutter blade edge 401.

Due to the inevitable accumulation of severed tissue on and within the debulker 250 and other cutter assembly components (e.g., up-cutters 452, down-cutters 454, etc.), it is preferred that they be disposable. In accordance with one aspect of the embodiments described herein, there are provided cutter assembly components that are disposable. Two or three or four our more of any of these components may be provided in a kit, enabling the clinician to dispose of one as desired and to introduce a new one into the procedure.

In accordance with one aspect of the embodiments described herein, there are provided blade arms and cutters that are designed to be rotated and used in one direction (i.e., clockwise or counter-clockwise). In one aspect, for the single-sided cutter blades 450 illustrated in FIGS. 17B-C, rotational motion of blade arms 402 in only one direction (e.g., clockwise) will initiate severing of nucleus material (see also up-cutters 452 and down-cutters 454 described herein). The intended motion during the use of these blades 401 is similar to the back and forth motion of a windshield wiper—wherein the excision with respect to these cutters occurs in the sweep that is clockwise in direction.

In one embodiment (not shown), one or more stops are placed within the cutter shaft 410 to control blade arc or range of motion. In another embodiment (not shown), one or more stops are fitted onto the dilator sheath 220 to control the blade arc or range of motion.

The shaft 410, cutter sheath 430 and the handle 416 components are preferably co-configured to enable the cutter blade arm 402 and the shaft 410 to which it is attached be able to be "pushed-pulled" so as to retract the blade arm 402 into and extended the blade arm 402 from the lumen 434 at the distal end 432 of the cutter guide tube 430, as needed. More specifically, the cutter blade edges(s) 401 of the cutter blade 453 are retracted into the cutter sheath 430 for delivery into the disc space. Once the sheath 430 is in position, the cutter blade edges (s) 401 are extended distally and rotated using the handle 416 to cut nucleus material. The cutter blade edge(s) 401 are again retracted into the cutter sheath 430 for removal of the cutter assembly unit 400 from the spine.

In one mode of use, particularly suitable for performing a nucleectomy of the L5-S1 intervertebral disc space, a series of cutting tools comprising debulkers, up-cutters, and/or down-cutters are used to separate disc material (e.g., nucleus pulposus and cartilage from within the disc space).

In one embodiment, the terms "debulking", "up-cutting", and "down-cutting" refer to the blade arms configurations that are used in a sequential and progressive fragmentation of the core nucleus pulposus within the central or core portion of the disc, the surface of the superior bone end plate, and the surface of the inferior bone end plate, respectively.

In one method of use, one or more debulkers 450, with blade arm lengths successively increasing from about 8 mm to about 15 mm, are used in the initial steps of performing nucleectomy. In one mode of operation, three debulkers—namely, a small debulker $450_S$, a medium debulker $450_M$, and a large debulker $450_L$—having blade arm lengths of about 8 mm, 11 mm, and 15 mm, respectively, are used prior to introduction of the cutters (e.g., up-cutters 452 and/or down-cutters 454).

In accordance with one aspect of the embodiments described herein, there are provided cutter configurations that advantageously enable the surgeon to have more precision and control with respect to the excision of nucleus material from the endplates. Some level of bone bleeding is generally associated with decortication (i.e., the scraping of the cutters against the surfaces of the end plates). Such bleeding can advantageously promote bone healing and/or osteogenesis in the normally a vascular area of the disc. This is particularly advantageous when the disc space is being prepared for subsequent procedures or implants where there is a need for accompanying bone growth. The cutter configurations and techniques of the present invention assist the surgeon in achieving an appropriate amount of bleeding in a controlled manner which does not otherwise compromise the bone endplate or adjacent structures.

In accordance with one aspect of the embodiments described herein, there are provided extraction tools for extracting tissue fragments from a treatment site, such as, for example, a disc space. While the extraction tools and devices are described in the context of their application to the removal of nucleus pulposus and cartilage material excised from the a spinal disc via axial access to a disc space, it will be understood that they can be used to remove other tissue fragments from the same or different treatment sites, or for lateral access into a disc space as well.

The extractor devices include configurations that can be inserted into the disc space through an axial approach to the lumbar spine. Such configurations include, but are not limited to, "wheel", "end" or "bottle" multifilament configurations. At the same time, the tools should be small enough to allow atraumatic entry into the disc via a cannulae (e.g., the large dilator sheath). The extractor tools are generally used to remove tissue fragments in the treatment site by snagging and pulling them out.

With reference to the embodiment of FIGS. 19A-D, there is provided a retractable tissue extractor 500 comprising an elongate extractor shaft 512 that extends between a distal end 514 and a proximal end 516. The extractor 500 preferably comprises a delivery sheath 520 that extends between a distal end 522 and a proximal end 524.

The extractor 500 comprises an extractor head 509 engaged with the distal end 514 and a handle 518 affixed to the proximal end 516. The extractor head 509 may be glued and pinned into or otherwise attached to the distally located receiving section of the extraction tool 500. The extractor handle 518 may be configured, constructed, and affixed to the extractor shaft in accordance with substantially the same means and materials as previously described and disclosed herein for cutter handles.

The extractor assembly 500 of FIGS. 19A-D is shown in its "pre-splayed" state, which refers to a first configuration or first, reduced cross sectional profile in which the filaments or wires 530 of the extractor head 509 on the distal end of extractor assembly 500 are in a reduced cross sectional orientation, to facilitate assembly into the shaft 512. In one aspect, the "pre-splayed" individual wires or filaments 530 of extractor head 509 are comprised as part of a multi-filar and/or multi-layer wound coil. The windings of the layers can be left-handed and/or right-handed, although it is preferred that all layers be wound in the same direction, and that a wound configuration for the individual filaments is preferable to a straight-filament configuration in order to assure that the filaments 530 will retain a helical or coiled configuration when unwound.

In the context of the present invention, as used herein the terms spiral, helical, or kinked refer to the fact that the filaments are not straight, and it is understood that they are not necessarily "uniformly" formed (e.g., not as reproducibly spaced coils).

In one embodiment, the extractor head 509 may be formed from a cable that is wound as 4 concentrically coiled, multi-filar layers (e.g., 6, 7, 8, 9 filaments or filars per layer) fabricated from the highest-tensile strength stainless steel wires commercially available. As will be described below, it is the combination of the tensile strength, diameter and helical or coiled configuration of the wires 530 when unraveled enable wire entanglement to effectively extract tissue fragments. The extractor head 509 is capable of being transformed from a first "pre-splayed" state (e.g., where the wires are wound together in a cable that has a bundle diameter of about 0.15") to a second, "splayed" state (i.e., a second, expanded cross sectional profile) by the unwinding of the wires 530 (e.g., stainless steel wires) with diameters of about 0.01".

Figure 20:
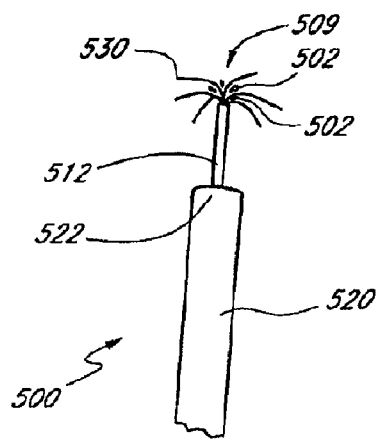
FIG. 20 illustrates the distal end of one embodiment of an extraction tool with tissue fragments within its wire strands.

With reference to FIG. 20, there is provided one embodiment of the extractor assembly 500 (with the extractor head 509 in a splayed state) that can be used to remove entrapped tissue fragments 502 from the treatment site. As shown, the tissue fragments 502 are entangled in the inter-wire spaces of the multiple strands 530.

In one embodiment, the extractor head 509, once unraveled and splayed, the reach or total spread of the extraction filaments 530, tip-to-tip is from about 0.50" to about 1.50". In a preferred embodiment, the reach of the extraction filaments 530 tip-to-tip is about 1.00".

The wires or filaments 530 are preferably stainless steel and of a diameter and tensile strengths, that enable retraction and delivery through the delivery sheath 520 without deforming extensively e.g., the individual filaments 530 retain their helical configuration and collectively maintain the radial reach of extractor head 509. In alternative embodiments, the wires can comprise, nickle alloys, nickel-titanium alloys, cobalt alloys, or the like.

Figure 21A:
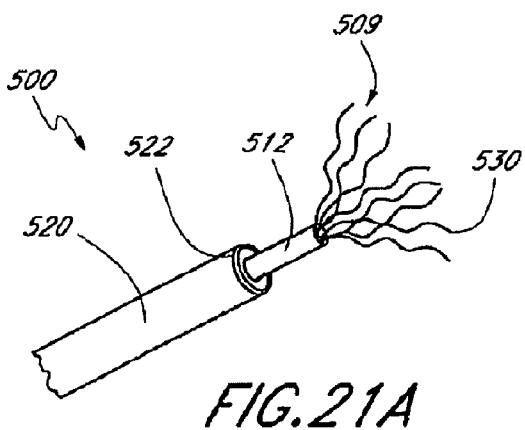
FIGS. 21A-B illustrate one embodiment of an extractor tool with its head extended into an exposed position and then pulled back into a delivery sleeve.
Figure 21B:
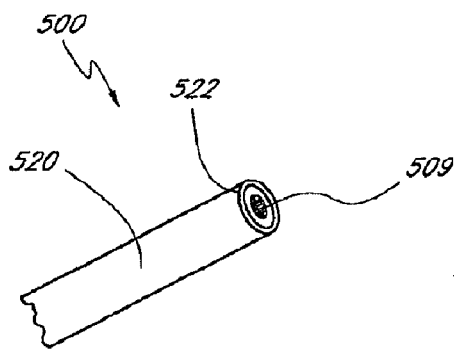
Figure 21C:
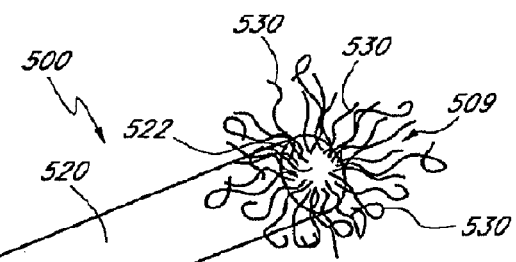
FIGS. 21C-D illustrate another embodiment of an extractor tool with its head in the extended position.
Figure 21D:
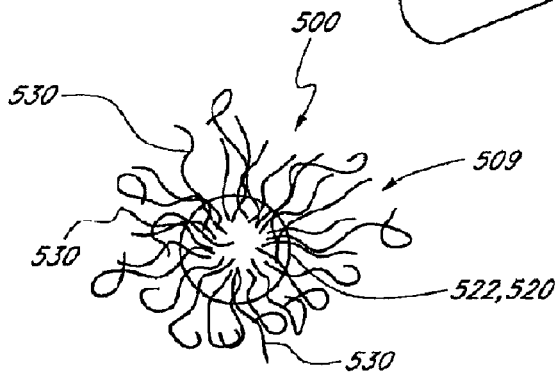

In one embodiment, shown in FIGS. 21C-D, the helical wires 530 of the extractor head 509 are splayed in a non-uniform pattern, so that the wires 530 overlap with each other. The wires 530 are preferably sufficiently stiff to snag tissue fragments 502, yet be pliable enough to compress and bend when tugged with tissue fragments 502 in tow. The mechanical properties, number, and spatial relationship among of the wires 530 impact effective tissue extraction of tissue fragments 502 as will be explained below.

Tissue fragments 502 are captured by the extractor head 509 in part as a result of the wires' surface areas, in part due to their own (inter-wire) physical entanglement with a concomitant entrapment of additional material as the extractor tool 500 is manually rotated or twisted and the spatial orientation among wires 530 changes. The tips at the distal end of the wires 530 are also sharp to assist in snagging.

The wires 530, however, are preferably not so stiff as to preclude deflection upon contact with stiffer/more solid elements other than fragmented and loosened tissue. The tissue extractor wires 530 are preferably soft enough to deform and conform to the irregularities of the bone surface and neither cut or erode other vertebral structures, such as bone or the annulus, so there is also no concomitant risk of further spine or spinal cord damage.

The density of wires 530 within the disc space is also a significant factor with respect to maximum tissue removal. When wire or bristle density (# wires per unit volume of disc space) is too high, the extractor head 509 tends to push material to the disc perimeter rather than collecting it. In one embodiment, the extractor head 509 comprises about 30 wires 530, each with a diameter of about 0.010". The disc space is typically small, with a cavity volume of about 6-8 cc, so a density with too many wires 530 (e.g., 50 strands, each with a diameter of about 0.010"), precludes their optimum interaction in removing tissue fragment 502. Extractor heads having at least about 5 to about 10, but often no more than about 40 or 50 strands, depending upon strand length and diameter, and desired clinical performance, are contemplated.

In one embodiment, the proximal end 534 of the wire cable comprising the extractor head 509 is brazed to the extractor shaft 512, which is formed of stainless steel tubing. In another embodiment, (FIG. 19B), the proximal end 534 of the extractor head 509 is affixed to the extractor shaft 512 by means of a pin 508, as well as adhesively affixed. Any of a variety of other attachment techniques may also be used, such as gluing, crimping and various potting techniques. Alternatively, the extractor head 509 may be sufficiently axially enlongated to extend to the proximal end 516 of the extractor shaft 512.

In one embodiment, the shaft 512 is formed from a solid polymer rod. Suitable rod materials include, but are not limited to, polymers which are machined and/or injection molded, and are able to be sterilized. Examples of such materials include acetal copolymer, acrylic, polyethylene, nylon, polycarbonate, polypropylene, PVC, ABS, or the like.

In one embodiment, the extractor shaft 512 is about 0.25" in diameter and is approximately 12.00" in length. As previously noted, the extractor assembly 500 should be small enough to allow atraumatic entry into the disc via a cannulae (e.g., the large dilator sheath 220).

In one embodiment, the extractor sheath 520 is formed from stainless steel tubing with an I.D. of about 0.26" and an O.D. of about 0.35".

With reference to FIGS. 19A-19 C, the extractor shaft 512 also may comprise a handle 518 that is affixed to its proximal end 516, to facilitate manipulation of the tool when removing tissue, and also to enable extension and retraction of the extractor head 509 as noted and described elsewhere. In order to prevent over-extension and over-retraction the extractor assembly 500 comprises stop means. One such stop means is shown in FIG. 19A, comprising a stop pin 515 and a slot 562. The stop pin 515 is affixed to the shaft 512 and configured to extend through slot 526 in the extractor sheath 520. The length of the slot 526 limits the travel of the pin and in turn the shaft 512, limiting extension and retraction of the shaft 512 and thus the extractor head 509. In one embodiment, the handle 518, which is of larger diameter then the extractor sheath 520, serves as an extension stop. More specifically, distance between the proximal end 524 of the sheath 520 and the distal end of the handle 518 controls the amount of exposure of the extractor head 509. A longer distance between end 524 and the handle 518 will result in an extractor 500 with a shaft 512 that can be distally advanced a longer distance, thereby resulting in increased exposure of the extractor head 509.

With reference to FIG. 16 I, as was previously described with respect to the cutter sheath 430, in a preferred embodiment, the extractor sheath 520 is configured with a shoulder 499 bored into its inner wall which serves as a stop that precludes the shaft 512, along with its extractor head 509 and handle 518, from becoming fully disengaged from the extractor sheath 520 when the extractor head 509 is retracted into the extractor sheath 520.

Figure 22A:
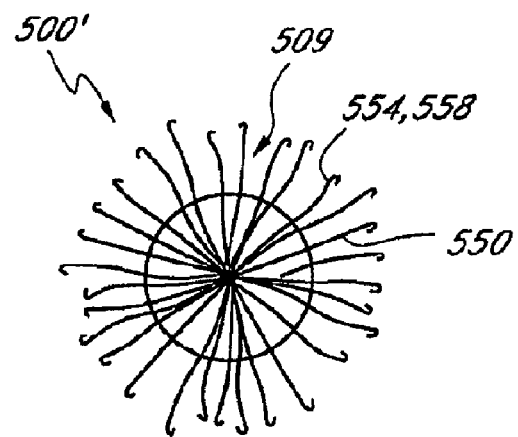
FIGS. 22A-B illustrate another embodiment of an extraction tool.
Figure 22B:
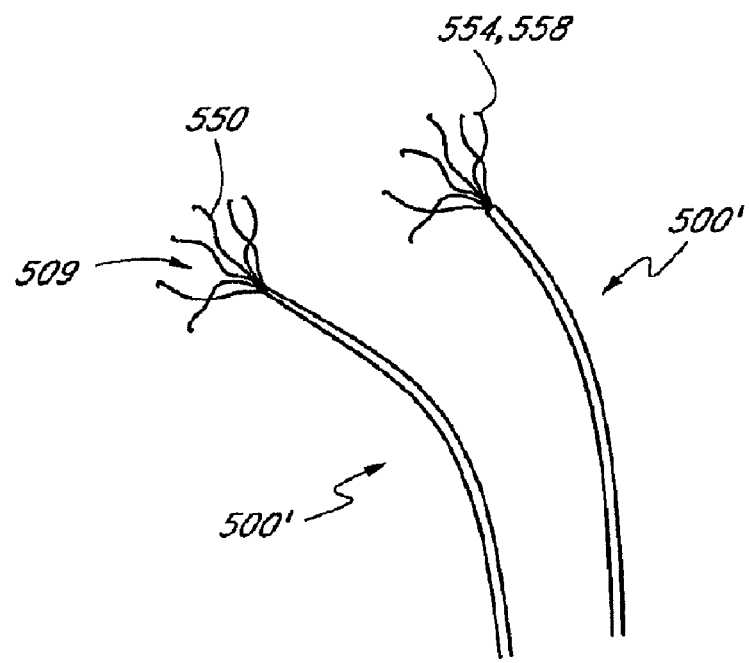

With reference to FIGS. 22A-B, in another aspect, the extractor head 509 comprises wires(s) 550 at least some of which, and in one embodiment all of which, are configured with hooks 558 on the distal ends 554 of the strands 550, for extracting tissue. The wires 550 are constructed from a metal such as stainless steel with a wire strand diameter from about 0.004" to about 0.020". Again, for the extended extractor head 509, the reach or total spread of the hooked wires 550, tip-to-tip is from about 0.50" to about 1.50". In a preferred embodiment, the reach of the extraction filaments 530 tip-to-tip is about 1.00".

The extractor head 509 comprising the hooked wires 550 is affixed to the extractor shaft 512 in substantially the same manner as previously described, above. In this embodiment as just described it is the hooked configuration of the wires 550 which extract tissue fragments 502 as opposed to the entanglement among individual wires with respect to the preferred kinked fimaments 530. The hooked wires 550 are configured so as not to excise, abrade, or otherwise compromise adjacent structures (e.g., the annulus).

Extractor heads 509 configured according to the embodiment of FIGS. 22A-B can snag material for removal with a lower strand density (i.e., number of strands per unit volume of disc space). In one approach, as few as two strands can be used operatively. Again, if the density of strands 550 is too high, the extractor head 509 tends to push tissue fragments 502 to the disc perimeter rather than collect it. In one embodiment, the head comprises fewer than about 30 wires 550.

With reference to FIGS. 19A-D and 21A-D, there is provided an extractor sheath 520 which restrains the extractor head 509 in the first, reduced configuration, which is retracted into or extended from the lumen at the distal end 522 of the extractor sheath 520 as the extractor assembly unit 500 is inserted or removed from the disc space, through the protected portal of the large dilator sheath 220.

In one mode of use, the targeted tissue site comprises a disc space and the tissue fragments to be extracted comprise nucleus material. In one mode of use, the extractor 500 is used to remove nucleus material after tissue cutters (e.g., debulkers, down-cutters, up-cutters, etc.) have been used to loosen up nucleus material within the disc cavity and end plate surfaces. In another approach, extractors 500 are used concurrently with the tissue cutters. In one method of use, approximately five extractor assembly units 500 are utilized in each procedure (i.e., during the nucleectomy of one disc).

In one embodiment, the extractor assembly 500 is a disposable, one-time use unit. Here, each extractor head 510 is only inserted once, in situ, into a disc cavity.

In accordance with one aspect of the embodiments described herein, there are provided various material inserters than can be used to deliver any number of suitable materials to a treatment site.

In accordance with one aspect of the embodiments described herein, there is provided a bone graft insertion tool that can be used to insert and pack bone material or paste into the disc following nucleectomy.

With reference to FIGS. 23A-D, in one embodiment, the bone graft inserter assembly (or bone growth material inserter) 600 comprises a packing instrument 602 and a delivery cannula 604, as shown in FIGS. 23C and 23D.

Referring to FIG. 23C, the packing instrument or packer 602 comprises a rod 610 that extends between a distal end 612 and a proximal end 614. In one embodiment, the rod is made from stainless steel or the like. The rod 610 is configured to be inserted into a central lumen extending through the delivery cannula 604. In one embodiment, the rod 610 has a diameter of about 0.156".

The packer 602 comprises an impactor mass such as a ball or handle 616 which may be attached to the proximal end 614. In one embodiment, the impactor ball 616 is press fit to the proximal end 614. The ball 616 is preferably solid and may be formed from a polymeric material, such as, for example, an acetal copolymer. In one embodiment, the ball 616 comprises a bore or aperture for receiving the proximal end 614 of the rod 610. In one embodiment, this bore is about 0.15" in diameter and about 0.50" deep. In one embodiment, the diameter of the ball is about 1.00".

The illustrated packer 602 comprises a bushing 618 attached to the distal end 612. In one embodiment, the bushing 618 is press fit to the distal end 612. The bushing 618 may be a solid cylindrical structure and formed from a known suitable polymeric material. In one embodiment, the O.D. of the bushing 618 is about 0.29".

In one embodiment, the bushing 618 comprises one or more O-rings 619 which provides a tight sliding fit between the bushing 618 and the inside wall of the central lumen extending through the delivery cannula 604, enabling insertion of bone growth facilitation materials which are less viscous, e.g., paste or liquid.

Referring to FIG. 23D, the delivery cannula 604 comprises a tube 620 that extends between a distal end 622 and a proximal end 624. In one embodiment, the tube 620 is machined from stainless steel tubing with an O.D. of about 0.31" and an I.D. of about 0.30".

The distal end 622 of the cannula 604 comprises a tip 626 that is preferably beveled at an angle to facilitate directional control of material as it is delivered into the treatment site, such as, for example, a disc space. In one embodiment, the tip 626 is beveled at an angle of approximately 45 degrees relative to the longitudinal axis of the cannula 604.

The proximal end 624 of the cannula 604 comprises a funnel 628. In one embodiment, the distal portion of the funnel 628 has an I.D. of about 0.30". The funnel increases in diameter toward its proximal end. In one embodiment, the funnel 628 is engaged with the tube 620 via brazing. In another embodiment the funnel 628 is engaged with the tube 620 by means of press fit. In one embodiment, the overall length of the tube 620 and funnel 628 is about 13.00". The funnel 628 may be fabricated from a polymeric material such as acetal copolymer.

In one mode of use, the cannula 604 is docked or otherwise secured to the entry to the treatment site. Bone paste or osteogenic material is inserted into the cannula 604 via the cannula tip 626 or by means of the funnel 628. The packer 602 is inserted into the funnel 628 and advanced distally to push bone paste out of the cannula distal end 622 and into the treatment site (e.g., a disc space). In one embodiment, as the packing rod 610 is advanced distally into the cannula 604, the impactor ball 616 hits the funnel 628 just as the bushing 618 reaches the distal end 622 of the cannula 604.

Figure 24A:
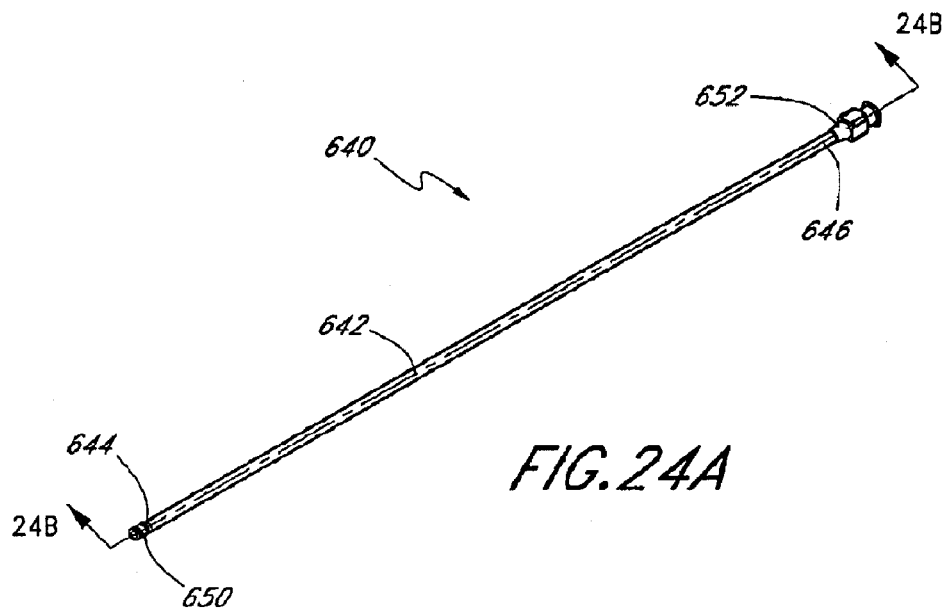
FIG. 24A is a perspective view of one embodiment of a paste-inserter assembly.
Figure 24B:
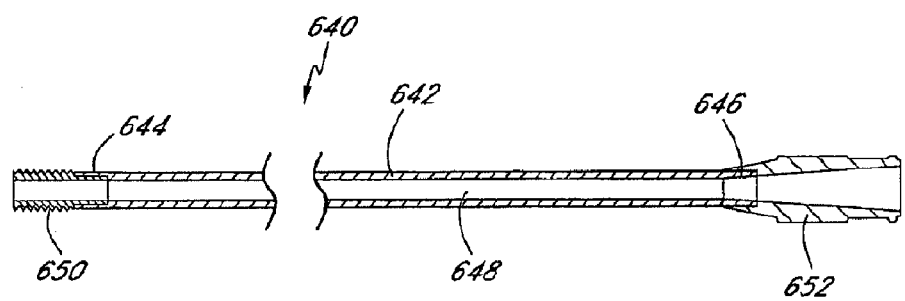
FIG. 24B is a side cross-sectional view the assembly of FIG. 24A.

In accordance with another aspect of the embodiments described herein, FIGS. 24A-24B illustrate a bone paste inserter 640 comprising a cannulated tube 642 that extends between a distal end 644 and a proximal end 646. The tube 642 defines an inner lumen 648.

A preferred assembly 640 also comprises a distally-located threaded portion 650 that may be formed directly on the tube 642 or engaged to the distal end 644 via any known suitable attachment technique. The threaded portion 650 is configured to engage with the threaded proximal ends of implants (e.g., and axial fusion rod) to facilitate the delivery of bone paste into the treatment site. In another embodiment, the assembly 640 lacks a threaded portion 650.

The assembly 640 also comprises a quick connect fitting such as a luer lock 652 at the proximal end 646. In one embodiment, the luer lock 652 is a 10 gauge luer lock. The tube 642 and threaded portion 650 is typically machined from stainless steel or other suitable material known in the art.

In one mode of use, bone paste is delivered through the paste inserter assembly 640 beginning at the luer lock 652, and through the tube 642, and into the treatment site via distal end 644.

In accordance with one aspect of the embodiments described herein, there is provided an allograft placement tool. With reference to FIGS. 25A-C, in one embodiment, the allograft placement tool (or augmentation material inserter) 950 comprises a cannulated tube 952 that extends between a distal end 954 and a proximal end 956, and that defines an inner lumen 955.

The tool 950 comprises an allograft delivery tip 958 attached to the distal end 954 via any known suitable attachment technique, such as, for example, press-fit, adhesive material, or the like. In one embodiment, the tip 958 is secured to the tube 952 with one or more pins 953 positioned within one or more transverse hole(s) on the tube 952 and into corresponding apertures 968 on the tip 958. The tip 958 comprises a stop such as an annular flange structure 970 which abuts the distal end of the tube 952 and which supports the position of the allograft during insertion.

The tip 958 comprises a distal opening 960, a proximal opening 962, and an inner lumen 964 that is in communication with the tube lumen 955. The tip 958 comprises threads 966 or other engagement structure to engage with the allograft being inserted into the treatment site.

It will be understood that any of the material inserters described herein can be used with any suitable material(s), depending on the particular type of treatment procedure and treatment site. For example, any one the material inserters described above (e.g., 600, 640, and 950) can be used for the delivery of augmentation materials (e.g., a hydrogel) to a treatment site (e.g., a disc space), thereby making the material inserter an augmentation material inserter.

In accordance with one aspect of the embodiments described herein, there is provided an exchange system providing a protected portal to the treatment site (e.g., the sacrum) for the insertion of instrumentation or implants having O.D. dimensions (e.g., greater than about 0.35") that are too large to be accommodated through the working and docking portal provided by the large dilator sheath (e.g., sheath 220 described above).

With reference to FIGS. 26-27 and 28A-B, in one embodiment, the exchange system assembly comprises an exchange bushing 702 and an exchange cannula 704.

The shaped exchange bushing 702 extends between a distal end 710 and a proximal end 712. The elongate, cannulated exchange bushing 702 is shaped and tapered toward its distal end 710. In one embodiment, the bushing 702 is cannulated with a central lumen having an inner diameter of about 0.14" (i.e., slightly larger than a diameter of a typical guide pin). In one embodiment, the length of the bushing 702 is approximately 14.00".

Bushing 702 has a tapered tip 714 at its distal end 710. In one embodiment, the tapered tip 714 starts at the inner diameter of the bushing 702 and continues at approximately an 18 degree angle for about 0.5" after which the taper cuts sharply back (i.e., flares out) towards the center of the bushing 702 and begins the taper again at about an 18 degree angle out to the outer diameter of the bushing 702. This creates an annular recess region in which the exchange fingers 724 of the cannula 704 can nest, thereby providing a protected profile during delivery (i.e., the bushing 702 protects the exchange fingers 724) See FIG. 27. Delivery may be accomplished over an extended guide pin.

In one embodiment, the exchange bushing 702 comprises a polymeric material, such as an acetal copolymer or the like. In another embodiment the exchange bushing 702 is fabricated from a metal or metal alloy, e.g., stainless steel. The exchange bushing 702 can be either machined or injection molded.

With reference to the embodiments in FIGS. 27 and 28A-B, there is provided an exchange system that comprises a "fingered" exchange cannula 704, which works in combination with the bushing 702. The exchange cannula 704 extends between a distal end 720 and a proximal end 722 and defines an inner lumen 728.

The exchange cannula 704 comprises a plurality of distally extending "fingers" 724 at the distal end 720 that are generally triangular in shape. FIG. 28A shows the exchange cannula 704 in the "open" position with its fingers 724 extended radially outward compared to the "closed" position. FIG. 28B shows the exchange cannula 704 in the "closed" or insertion position with its fingers 724 congregated about a central axis, thereby forming a conical tip 726. The conical tip 726 is designed to enter the sacral bore, and to hold dilation and position intact during subsequent deployment of instrumentation or implants.

In one embodiment, the exchange cannula 704 is formed from polymeric tubing (e.g., such as acetal copolymer) In one embodiment, the cannula 704 is about 8.00" in length, and comprises from 3 to 8 "fingers" 724 at the distal end 720 that are approximately triangular in shape. Here, the fingers 724 are approximately 1.00" in length and configured so as to collapse towards the longitudinal axis of the cannula at approximately a 30 degree angle.

In one mode of use, the exchange cannula 704 is seated on the outside of the shaped exchange bushing 702 during insertion into the sacrum following removal of the large dilator sheath 220 (i.e., working cannula that was used for cutting and extraction). Once the shaped exchange bushing 702 is seated in the sacrum, the exchange cannula 704 is advanced distally and into place. The fingers 724 of the exchange cannula 704 slip into the hole or entry point leading to the treatment site, and the shaped exchange bushing 702 is withdrawn enabling the insertion of subsequent instrumentation or other devices and implants through the lumen 728 of the exchange cannula 704 and into the treatment site. In one approach, the subsequent instruments can optionally be advanced through the cannula 704 in combination with a guide pin.

With reference to FIGS. 29A-B, the largest O.D. of the to-be-deployed device 800 (i.e., the O.D. toward the proximal end of the device 800) exceeds that of the dilator sheath 220 and that of the exchange cannula 704 while in its "closed" configuration. The device 800 is subsequently delivered to the treatment site by radially outwardly displacing the fingers 724 of the exchange cannula 704 to create a pathway that has a diameter large enough to accommodate the passage of the device 800, while isolating the working channel from adjacent organs or anatomical structures.

In accordance with another aspect of the embodiments described herein, there is provided an exchange system that provides a protected a portal to a treatment site, and that comprises an exchange bushing and an exchange tube. With reference to FIGS. 30A-C, in one embodiment, there is provided exchange system assembly 730 comprising an exchange bushing 732 and an exchange cannula 734.

The exchange bushing 732 comprises a tube 740 that extends between a distal end 742 and a proximal end 744, and defines an inner lumen 741. The bushing distal end 742 is typically beveled at an angle of about 20° to about 70°, often about 30° to about 60°. In one embodiment, the distal end is beveled at an angle of about 45°. The outside diameter may also be tapered to a reduced diameter at the distal end 742 to facilitate advance through the tissue tract.

The bushing 732 is typically machined or injection molded from stainless steel, delrin etc. or any other known suitable material.

The exchange cannula 734 comprises a tube 750 that extends between a distal end 752 and a proximal end 754, and defining an inner lumen 751. The tube distal end 752 is typically beveled at an angle of about 20° to about 70°, often about 30° to about 60°. In one embodiment, the distal end 752 is beveled at an angle of about 45°.

The exchange cannula 734 is typically formed from stainless steel, or from a suitable polymer, such as acetal copolymer, or the like.

With reference to the exchange assembly 730 shown in FIG. 30A, the distal portion of the exchange bushing 732 protrudes from distal end 752 of the exchange tube 734. In one mode of use, the bushing 732 is distally advanced into the sacrum over the dilator sheath 220 described above. Once the bushing 732 is advanced over the sheath 200 and seated on the sacrum, the exchange cannula 734 is distally advanced over the bushing 732 and into place. The bushing 732 is then withdrawn over the dilator sheath 220, which is then also removed, enabling the insertion of subsequent instruments, devices, or implants through the lumen 751 of the tube 734. In one embodiment, the subsequent instruments, devices, or implants are advanced through the lumen 751 over a guidewire. In another embodiment, the subsequent instruments, devices, or implants are advanced through the lumen 751 without the aid of a guidewire.

Figure 30D:
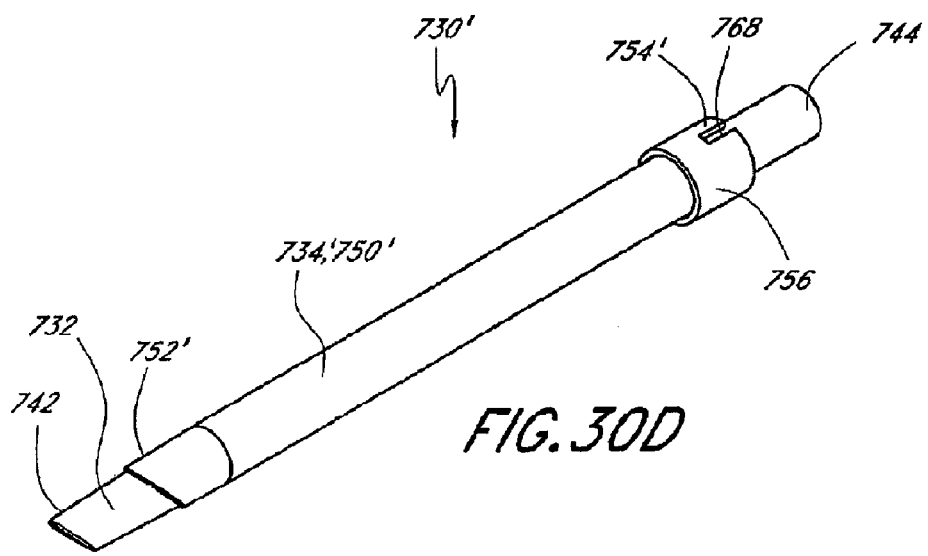
FIG. 30D is a perspective view of another embodiment of an exchange system comprising an exchange bushing and an exchange tube.
Figure 30E:
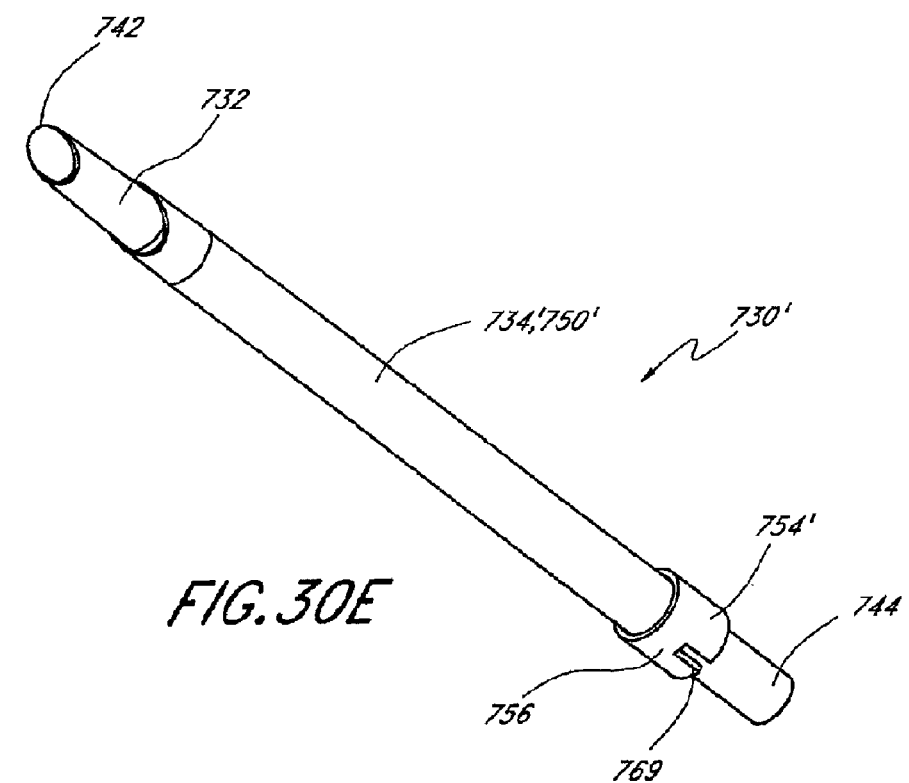
FIG. 30E is a bottom perspective view of the exchange system of FIG. 30D.

With reference to FIGS. 30D-E, in a preferred embodiment, the exchange system 730' comprises a bushing 732 and an exchange cannula 734'. The exchange cannula 734' comprises a handle such as an annular band 756 at the proximal end 754'. The annular band 756 or other aspect of proximal end 744 comprises one or more indicium such as lines, pins or notches 768, 769, as orientation indicators to show the rotational alignment of the bevel of the distal end 752' of the exchange cannula 734'.

In accordance with one aspect of the embodiments described herein, there is provided a temporary distraction device for separating adjacent vertebral bodies. In one mode of use, the temporary distraction tool is used for preparation of a disc space for receipt of augmentation materials (e.g., osteogenic materials, or annulus repair or sealant materials). In another mode of use, the temporary distraction tool is used to prepare a disc space for subsequent soft fusion (e.g., osteogenic, osteoconductive, or osteoinductive procedure without a fusion rod). In another mode of use, the temporary distraction tool is used to accommodate subsequent implantation of fusion or motion preservation devices. Background information on distraction devices in general appears in co-pending U.S. patent application Ser. No. 10/309,416, filed on Dec. 3, 2002, the content of which is incorporated in its entirety into this disclosure by reference.

In an application where only temporary distraction is desired, a temporary distraction device should be able to cause a separation of the adjacent vertebral bodies, and thereafter be removed without causing compression of the intervening disc. This is accomplished in accordance with the present invention by providing a temporary distraction working tip on a temporary distraction tool which is similar to the distraction implant 800 previously described. However, by providing the device in two pieces as described below, the structure may be utilized to achieve distraction by rotation in a first direction, and the device may thereafter be removed from the patient without causing compression.

In accordance with one aspect of the embodiments described herein, there is provided a two-piece temporary distraction device for achieving separation of adjacent vertebral bodies, while permitting removal of the device without recompressing the intervening disc space. In one embodiment, shown in FIGS. 31, 32A-B and 33A-E, the two-piece temporary distraction device 860 comprises a distal piece 862 and a proximal piece 864.

The distal and proximal pieces 862 and 864 comprise screw external threads 863 and 865, respectively. The thread pitches of the external threads 863 and 865 are chosen to achieve the desired or targeted level of distraction, as explained in further detail in co-pending and commonly assigned U.S. patent application Ser. No. 10/309,416 filed on Dec. 3, 2002, which is incorporated herein in its entirety by reference.

Figure 33A:
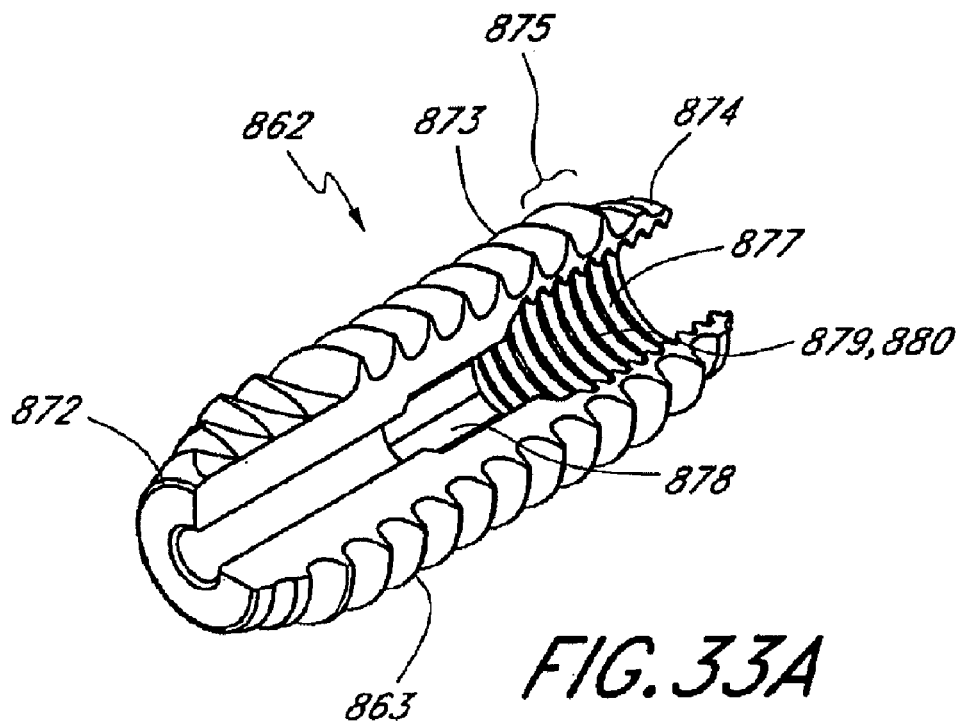
FIG. 33A is a perspective, partial cut-away view of the distal portion of one embodiment of a temporary distraction rod.
Figure 33B:
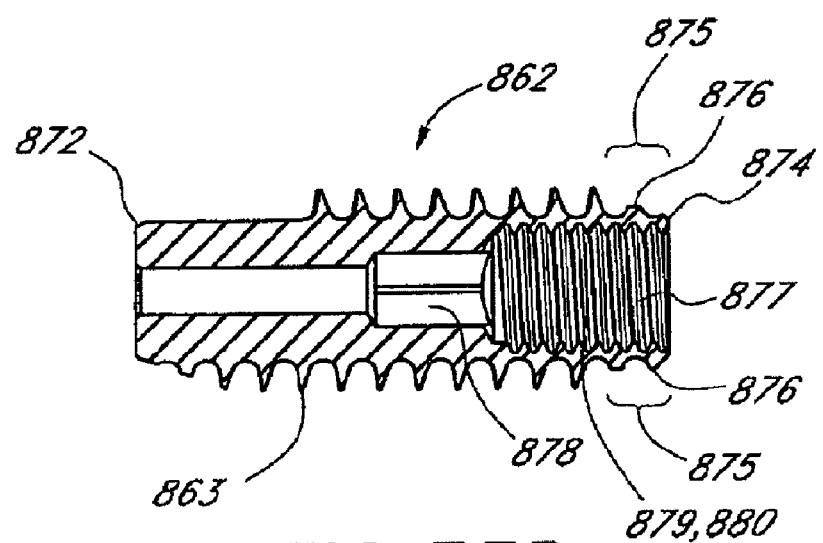
FIG. 33B is a side cross-sectional view of the rod distal portion of FIG. 33A.

With reference to FIGS. 33A-B, the distal piece 862 extends between a distal end 872 and a proximal end 874 and has external threading 863 along at least a portion of its longitudinal axis. The proximal end 874 of the distal piece 862 comprises an external non-threaded segment 875. In the present embodiment, non-threaded segment 875 comprises the male portion of a lap joint that engages female portion 885 of proximal piece 864, as described in further detail below.

The external threading 863 typically has a pitch of about 10 to about 16 threads per inch, often about 10 to about 14 threads per inch. The external threading 863 typically has a major diameter of about 0.350" to about 0.550", often about 0.400" to about 0.500". The external threading 863 typically has a minor diameter of about 0.230" to about 0.490", often about 0.280" to about 0.380". In one embodiment, the external threading 863 on distal piece 862 extends about 1.00" along the longitudinal axis of the distal piece 862.

The distal piece 862 comprises a cavity 877 defined by an internal unthreaded segment 878 and an internal threaded segment 879. The dimensions of segments 878 and 879 are chosen to facilitate temporary engagement with the insertion tip 900 of the insertion assembly 901, as well as temporary engagement with the extraction tip 920 of the extraction assembly 921, as described in further detail below.

Internal segment 878 is typically non-circular in cross-section. For example, in the present embodiment, the segment 878 comprises a rectangular cross-section. In another embodiment, not illustrated, the segment 878 comprises a hexagonal or other polygon or non circular cross-section. In general, cross-sectional shape of the segment 878 is complementary to the shape or geometry of segment 910 of the insertion tip 900 of the insertion assembly 901, described in further detail below, to allow torque transmission from the insertion assembly 901 to the distal piece 862.

Internal threaded segment 879 comprises internal threading 880 that is complementary to external threading 930 on the extraction tip 920 of the extraction assembly 921, described in further detail below. The portion of the cavity 877 defined by the segment 879 typically has a larger diameter than that defined by the segment 878.

The length of the distal piece 862 is typically in the range of about 0.5" to about 2.00", often about 1.00" to about 1.25". In one exemplary embodiment, the length of the distal piece 862 is approximately 1.125".

The actual dimensions (e.g., length, inner diameter, outer diameter, etc.) of the distal piece 862, proximal piece 864, device 860, etc. described herein will depend in part on the nature of the treatment procedure and the physical characteristics of the patient, as well as the construction materials and intended functionality, as will be apparent to those of skill in the art.

Figure 33C:
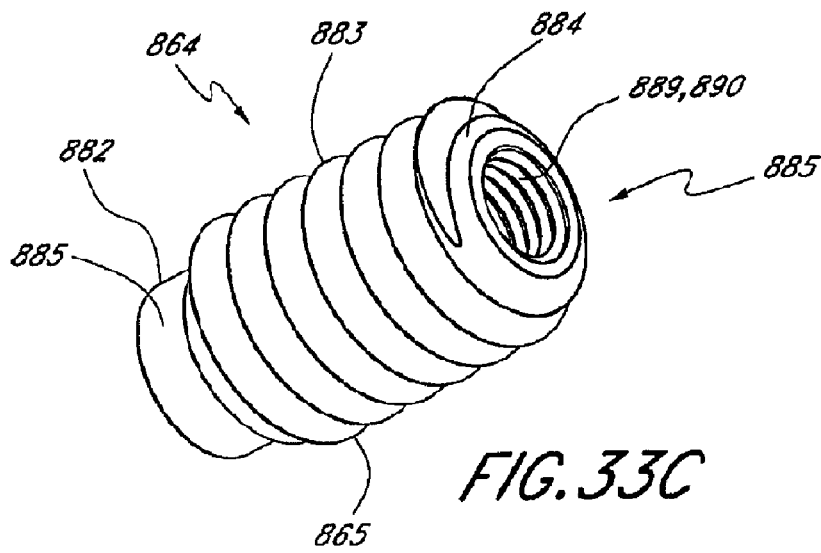
FIG. 33C is a perspective view of the proximal portion of one embodiment of a temporary distraction rod.
Figure 33D:
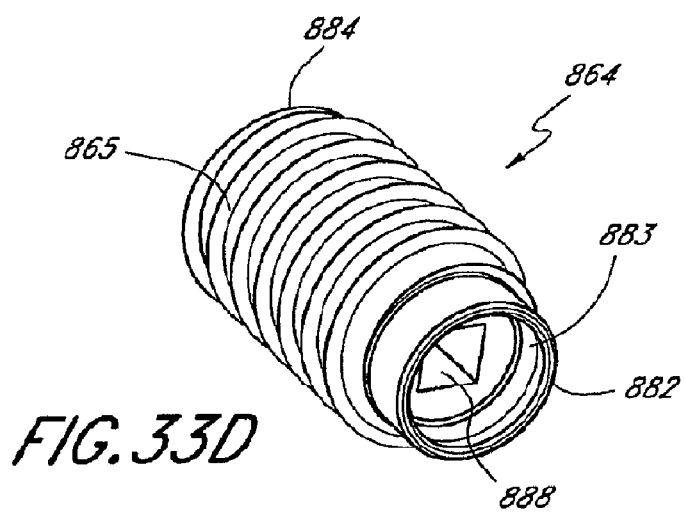
FIG. 33D is another perspective view of the rod proximal portion of FIG. 33C.
Figure 33E:
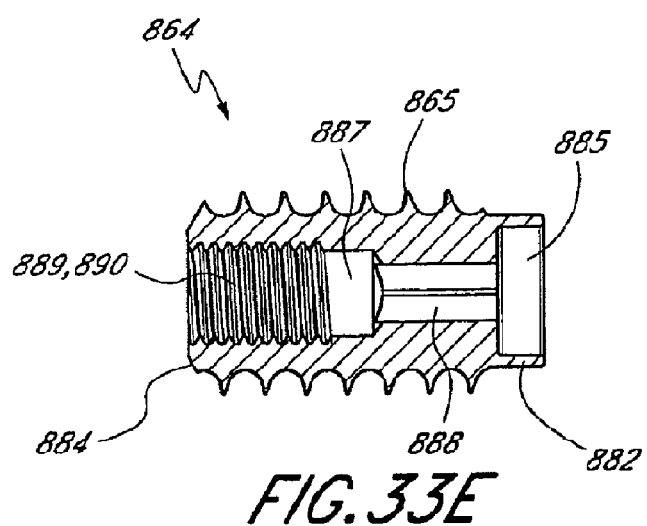
FIG. 33E is a side cross-sectional view of the rod proximal portion of FIG. 33C.

With reference to FIGS. 33C-E, the proximal piece 864 extends between a distal end 882 and a proximal end 884 and has external threading 865 along a portion of its longitudinal axis. The distal end 882 of the proximal piece 864 comprises an internal non-threaded segment 885 In the present embodiment, non-threaded segment 885 comprises the female portion of a lap joint that engages male portion 875 of distal piece 862.

The proximal piece 864 comprises a cavity 887 defined by internal unthreaded segment 888 and internal threaded segment 889. The dimensions of segments 888 and 889 are chosen to facilitate temporary engagement with the insertion tip 900 of the insertion assembly 901, as well as temporary engagement with the extraction tip 920 of the extraction assembly 921, as described in further detail below.

As with internal segment 878 described above, internal segment 888 is typically non-circular in cross-section. For example, in the present embodiment, the segment 888 comprises a polygon such as a rectangular cross-section. The cross-sectional shape of the segment 888 is complementary to the cross-sectional shape of segment 910 of the insertion tip 900 of the insertion assembly 901.

As with internal threaded segment 879 described above, internal threaded segment 889 comprises internal threading 890 that is complementary to the external threading 930 on the extraction tip 920 of the extraction assembly 921. The portion of the cavity 887 defined by the segment 889 typically has a larger diameter than that defined by the segment 888.

The length of the proximal piece 864 is typically in the range of about 0.5" to about 1.75", often about 0.75" to about 1.25". In one exemplary embodiment, the length of the proximal piece 864 is approximately 1.00".

The outer diameter (O.D.; i.e., the major thread diameter) of the proximal piece 864 is typically in the range of about 0.40" to about 0.70", often about 0.5" to about 0.6". In one exemplary embodiment, the O.D. of the proximal piece 864 is approximately 0.550".

The threading 865 typically has a pitch of about 8 to about 12 threads per inch, often about 9 to about 11 threads per inch. The threading 865 typically has a minor diameter of about 0.240" to about 0.620", often about 0.380" to about 0.480".

In one embodiment, internal threaded segment 889 has a length of about 0.375" along the longitudinal axis. In one embodiment, the internal unthreaded segment 888 has a length of about 0.625" along the longitudinal axis.

In one embodiment, the distal piece 862 and proximal piece 864 of the temporary distraction device 860 are positioned relative to each other by engaging the male portion of lap joint 875 with the female portion 885.

The length of the assembled device 860 is typically in the range of about 1.50" to about 2.50", often about 1.90" to about 2.10". In one exemplary embodiment, the length of the device 860 is approximately 2.00".

The distal and proximal pieces 862, 864 are typically made from any known suitable material, such as, for example, stainless steel, titanium, aluminum, or the like, or composites thereof.

In accordance with one aspect of the embodiments described herein, there is provided an insertion assembly for delivering a two-piece temporary distraction device into the treatment site.

In one embodiment, shown in FIGS. 32A and 34A-C, the assembly 901 comprises a two-piece temporary distraction device 860, an insertion tip 900, and a driver tool 855.

Figure 34C:
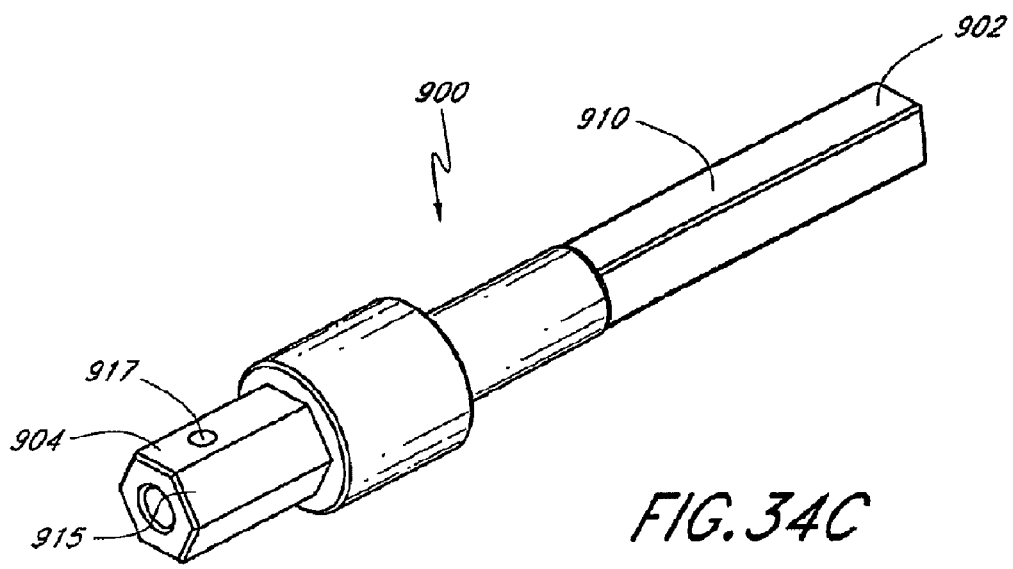
FIG. 34C is another perspective view of the insertion tip of the assembly of FIG. 34A.

With reference to FIGS. 34A-C, the insertion tip 900 extends between a distal end 902 and a proximal end 904 and comprises a distally-located segment 910 that is designed to releasably engage with internal segments 878 and 888 of the two-piece device 860. In the present exemplary embodiment, the segment 910 comprises a rectangular structure. In another embodiment, not illustrated, the segment 910 comprises a hexagonal, or other noncircular longitudinally extending structure.

The insertion tip 900 comprises a proximally-located segment 915 that is shaped and dimensioned to engage with the driver tool 855, described in further detail below. In the present exemplary embodiment, the segment 915 comprises a hexagonal cross-section. In another embodiment, the segment 915 comprises an octagonal or other non-circular longitudinally extending structure.

The insertion tip 900 may also be provided with one or more attachment structures such as holes or recesses 917 positioned to align with corresponding structure such as hole(s) 859 of the driver tool 855 to receive one or more screws or pins 854 to secure the tip 900 into the driver tool 855.

The length of the segment 910, is typically in the range of about 0.50" to about 1.50", often about 0.90" to about 1.10". In one exemplary embodiment, the length of the insertion tip 900 is approximately 1.00".

The insertion tip 900 is typically made from any known suitable material, such as, for example, stainless steel (e.g., 17-4 alloy), titanium, or the like, or composites thereof.

With reference to FIGS. 31, 32A and 34A-C, the driver tool 855 comprises a shaft 899 that extends between a distal end 856 and a proximal end 857. The tool 855 comprises a proximally-located handle 858 and one or more distally-located holes 859 positioned to align with the hole(s) 917 of the insertion tip 900 (described above) or the extraction tip 920 (described below), and to receive one or more screws or pins 854 to secure tips 900 or 920 into the tool 855.

The distal end 856 of the driver tool 855 comprises an aperture 850 for receiving the proximally-located segments 915 and 935 of the tips 900 and 920, respectively. In general, the cross-sectional shape and longitudinal length of the aperture 850 is complementary to that of segments 915 and 935. For example, in the illustrated embodiment, both the aperture 850 and segments 915 and 935 comprise a hexagonal cross-section and have a length of about 0.375".

The overall length of the driver tool 855 is typically in the range of about 12.00" to about 16.00", often about 13.00" to about 15.00". In one exemplary embodiment, the length of the driver tool 855 is approximately 14.00".

The outer diameter (O.D.) of the driver tool 855 is typically in the range of about 0.25" to about 0.50", often about 0.35" to about 0.40". In one exemplary embodiment, the O.D. of the driver tool 855 is approximately 0.375".

The driver tool 855 and its component parts are typically made from any known suitable material, such as, for example, stainless steel, titanium, aluminum, or the like, or composites thereof. The handle 858 is typically welded over the proximal end 857 of the tool 855.

In accordance with one aspect of the embodiments described herein, there is provided an extraction assembly for removing a temporary distraction device without causing compression across the intervening disc space.

In one embodiment, shown in FIGS. 32B and 35A-C, the assembly 921 comprises a two-piece temporary distraction device 860, an extraction tip 920, and a driver tool 855.

Figure 35A:
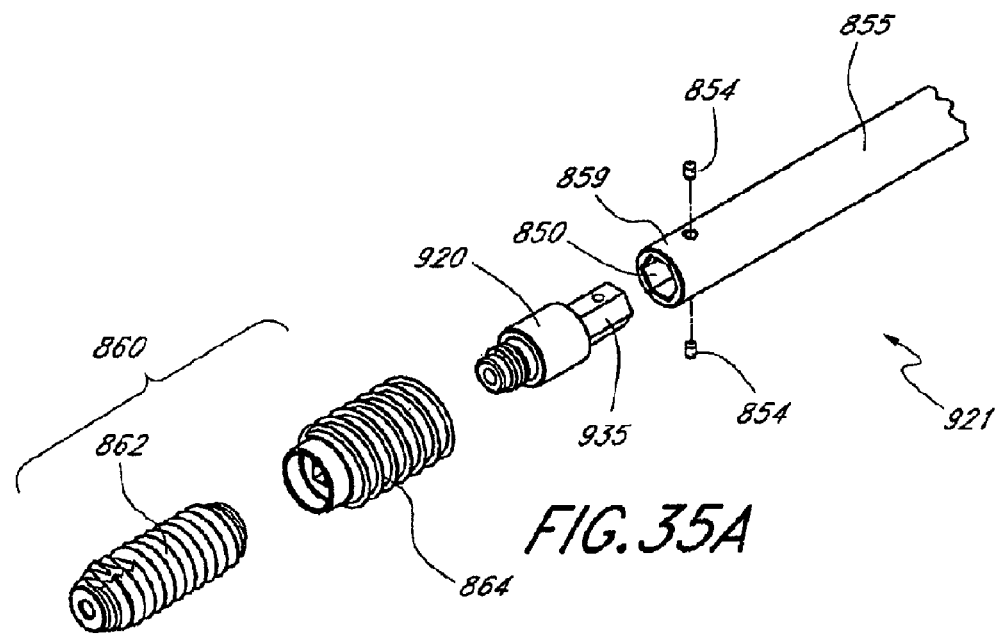
FIG. 35A is a perspective, exploded view of one embodiment of a temporary distraction-rod-assembly, shown with the removal tool.
Figure 35B:
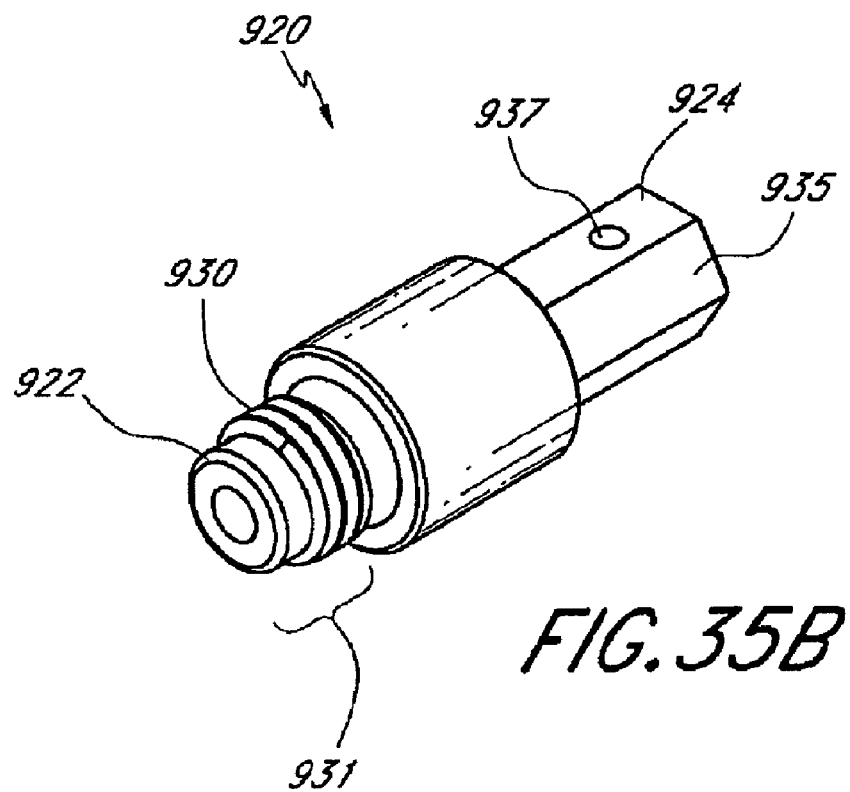
FIG. 35B is a front perspective view of the tip of the removal tool assembly of FIG. 35A.
Figure 35C:
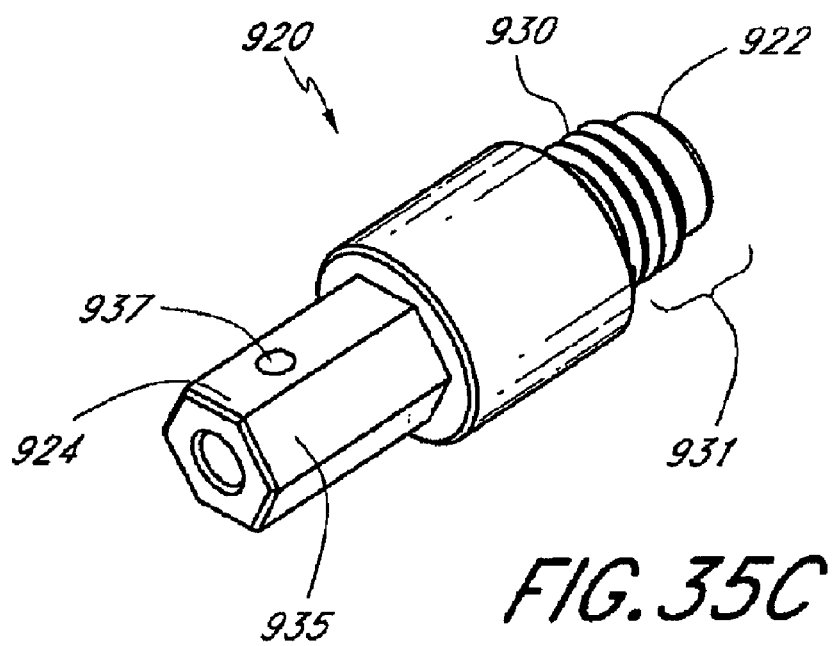
FIG. 35C is a rear perspective view of the tip of the removal tool assembly of FIG. 35A.

With reference to FIGS. 35A-C, in one embodiment, the extraction tip 920 extends between a distal end 922 and a proximal end 924 and comprises a distally-located threaded segment 931 that is designed to releasably engage with the receiving segments 879 and 889 of the distal piece 862 and proximal piece 864, respectively of the distraction device 860.

In one embodiment, the distally-located threaded segment 931 of the extraction tip 920 comprises left-handed external threads 930 that complement left-handed internal threads 880 and 890 of the receiving segments 879 and 889, respectively. The left-handedness of the threads 880, 890, 930 make it possible to rotate the extraction tool assembly 921 in a counter-clockwise direction, to engage each piece 862 and piece 864, and remove or extract each of them sequentially, proximal 864 first, from the treatment site while rotating the assembly 921 in the counter-clockwise direction to unscrew each of the pieces of the distraction device 860 from the bone.

The extraction tip 920 comprises a proximally-located attachment surface on segment 935 that is shaped and dimensioned to releasably engage with a corresponding surface on driver tool 855. In the present exemplary embodiment, the segment 935 comprises a hexagonal cross-section. In another embodiment, not illustrated, the segment 935 comprises an octagonal cross-section or other non-circular longitudinally extending structure.

The extraction tip 920 also comprises a releasable engagement structure such as one or more holes 937 positioned to align with hole(s) 859 of the driver tool 855 and receive one or more screws or pins 854 to secure the tip 920 into the driver tool 855. Preferably, the components of the system are configured such that the same driver tool 855 can be used to extract both the proximal piece 864 and distal piece 862 from the treatment site.

The length of the extraction tip 920 is typically in the range of about 0.50' to about 1.50", often about 0.90" to about 1.10". In one exemplary embodiment, the length of the extraction tip 920 is approximately 1.00". The extraction tip 920 is typically made from any known suitable material, such as, for example, stainless steel, titanium, or the like, or composites thereof.

In accordance with one aspect of the modes of use described herein, there are provided methods of using a two-piece distraction device to temporarily separate two or more vertebral bodies in the spine.

In one mode of use, for a two vertebral body application, the two-piece temporary distraction device 860 is introduced into the treatment site by advancing segment 910 of the insertion tip 900 coaxially into engagement with internal segments 878 and 888 of the device 860, and then rotating the device 860 into an axial bore as described elsewhere herein, under force applied generally distally. In one typical application, the device 860 is used to cause the separation of two adjacent vertebral bodies along the AAIIL. The device 860 is advanced through a caudal, proximal vertebral body, through an intervertebral disc, and into a cephalad, distal vertebral body, thereby causing distraction of the cephalad and caudal vertebral bodies, relative to each other. Rotation is continued until the desired degree of distraction has been achieved, as may be evaluated using conventional imaging technology. Over distraction can be corrected by rotating the distraction device 860 in an opposite direction.

Once the desired distraction has been achieved, the device 860 may be removed from the treatment site piece-by-piece by sequentially removing the proximal piece 864 and the distal piece 862 in a proximal direction. Following proximal retraction of the insertion tool, segment 931 of the extraction tip 920 is distally advanced to and rotatably engaged with the internal segment 889 of the proximal piece 864, and then rotated in a predetermined direction to cause disengaged of the proximal piece 864 from the distal piece 862, and thereby facilitating removal of the proximal piece 864 from the treatment site. The segment 931 is then readvanced distally through the access bore and engaged with the internal segment 879 of the distal piece 862, and then rotated in a predetermined direction to cause of the distal piece 862 to be extracted from the treatment site.

In one mode of use, the above-described two-piece device 860 and assemblies 901 and 921 are used to achieve temporary distraction (i.e., restoration of disc height) in preparation for implantation of either a fusion or a mobility restoration or preservation device as noted above. In one approach, distraction is maintained following removal of the distraction device 860 and before implantation of the therapeutic implant by having the patient lie in a prone or flat position on a horizontal surface, thereby relieving the patient's spine of axial compressive forces resulting from load bearing, motion, and the effects of gravity. In a fusion application, an implantable distraction device or other fusion implant may be supplemented by subsequent posterior insertion of facet or pedicle screws.

Various combinations of the tools and devices described above may be provided in the form of kits, so that all of the tools desirable for performing a particular procedure will be available in a single package. Kits in accordance with the present invention may include access kits, such as for achieving percutaneous access to the sacrum, and access kits for achieving soft tissue access to the sacrum and access through the sacrum into the desired treatment zone. Kits may also be provided with the tools necessary for disc preparation. Further kits may be provided with temporary distraction and/or insertion tools for insertion of implants.

Access kits may include all or any sub-combination of the following components, which have been described previously herein: one or more guide pin introducers, stylet, guide pin, guide pin handle, and guide pin extension. Each of these components may be either reusable or disposable. The access kit may additionally include one or more dilators, such as a 6 mm dilator and 8 mm dilator, and a 10 mm dilator with sheath. In one implementation of the kit, each of the dilators is reusable, and the sheath is disposable. The access kit may additionally include twist drills, such as a 6 mm, 7.5 mm and 9 mm drills which may be reusable.

Disc preparation kits may differ, depending upon whether the procedure is intended to be one level or multi-level. The disc preparation kit may include a plurality of cutters. In a single level kit, anywhere from 3 to 7 cutters and, in one embodiment, 5 cutters are provided. In a two level kit, anywhere from 5 to 14 cutters may be provided, and, in one embodiment, 10 cutters are provided. All of the cutters may be one time use disposable.

The disc preparation kit may additionally include one or more tissue extraction tools, for removing fragments of the nucleus. In a one level kit, 3 to 8 tissue extraction tools, and, in one embodiment, 6 tissue extraction tools are provided. In a two level disc preparation kit, anywhere from about to 8 to about 14 tissue extraction tools, and, in one embodiment, 12 tissue extraction tools are provided. The tissue extraction tools may be disposable.

The disc preparation kit may additionally include a bone graft inserter, which may be disposable.

An allograft kit may be provided including, in addition to the tools in the access and disc preparation kits, an allograft inserter tool and a temporary distraction tool. A selection of twist drills may be provided, such as a 9.5 mm, 10 mm, 10.5 mm, 11 mm or 11.5 mm twist drill, depending upon the size of the desired graft. The allograft kit may additionally include an exchange system, including a cannula and bushing, as have been described previously herein.

A fusion kit intended for a one level fusion may include, in addition to the tools in the access and disc preparation with bone graft inserter kits a one piece fusion rod, a rod driver, and a paste inserter. The fusion kit may additionally include a plug, a plug driver, and one or more twist drills such as a 7.5 mm and a 6 mm. The fusion kit will additionally include an exchange system as has been discussed. The rod driver and twist drills may be reusable.

In an alternate fusion kit, intended for two-level fusion, the kit may include one, two-pieces fusion rods, or one, one-piece fusion rod and one mobility implant, or a two-piece implant, one of which is a fusion implant and one of which is a mobility device The fusion kit additionally includes a rod driver, a paste inserter, one proximal and one distal plugs and two plug drivers. The fusion kit may additionally include one or more twist drills, such as a 7.5 mm and a 6 mm twist drill. The fusion kit will additionally include an exchange system.

Although the present invention has been described in terms of certain preferred structures and embodiments, variations on the foregoing will become apparent to those of skill in art in view of the disclosure herein, and are considered to be within the scope of the present invention. Accordingly, the present invention is not intended to be limited by any of the forgoing disclosure, and is instead intended to extend to the full scope of the following claims.

What is claimed is:

1. A method of implanting and removing a spinal implant comprising a first section and a second section, the method comprising:

advancing the first and second sections of the spinal implant into a spine;

using a tip of an extraction member to engage and withdraw the first section of the spinal implant from the spine; and using the tip of the extraction member to engage and withdraw the second section of the spinal implant from the spine, wherein the tip of the extraction member comprises a thread configured to complement and releasably engage at least one of the first and the second sections of the spinal implant.

2. The method of claim 1, wherein the tip of the extraction member releasably engages the first section of the spinal implant.

3. The method of claim 1, wherein the tip of the extraction member releasably engages the second section of the spinal implant.

4. The method of claim 1, wherein the tip of the extraction member comprises a non-circular longitudinally extending structure configured to complement and releasably engage at least one of the first and the second sections of the spinal implant.

5. The method of claim 1, wherein the tip of the extraction member is configured to engage at least one of the first and the second sections of the spinal implant with the spine through rotation in a first direction.

6. The method of claim 5, wherein the tip of the extraction member is configured to withdraw at least one of the first and the second sections of the spinal implant with the spine through rotation in a second direction, the second direction opposite the first direction.

7. The method of claim 1, wherein the tip of the extraction member is configured to engage both the first and the second sections of the spinal implant with the spine.

8. The method of claim 1, wherein the tip of the extraction member is configured to withdraw both the first and the second sections of the spinal implant from the spine.

9. A method of implanting and removing a spinal implant extending trans-axially between at least two adjacent vertebral bodies in a spine, the method comprising engaging a drive member with a non-circular cross-section with a corresponding non-circular portion of an internal bore of a spinal implant;

rotating the drive member and the spinal implant in a first direction to advance the spinal implant trans-axially into at least one vertebral body;

disengaging the drive member from the spinal implant;

engaging a threaded member with a threaded portion of the internal bore of the spinal implant by rotating the threaded member in a second direction that is opposite the first direction;

continuing to rotate the threaded member in the second direction to rotate the spinal implant in the second direction; and withdrawing the spinal implant from the least one vertebral body.

10. The method of claim 9, wherein the engaging the non-circular cross-section comprises interfacing at least three corresponding longitudinally extending surfaces between the drive member and the internal bore of the spinal implant.

11. The method of claim 9, further comprising aligning a releasable engagement structure between the drive member and the spinal implant.

* * * * *

UNITED STATES PATENT AND TRADEMARK OFFICE
CERTIFICATE OF CORRECTION

| | |
|---|---|
| PATENT NO. | : 8,308,777 B2 |
| APPLICATION NO. | : 12/870000 |
| DATED | : November 13, 2012 |
| INVENTOR(S) | : Assell et al. |

It is certified that error appears in the above-identified patent and that said Letters Patent is hereby corrected as shown below:

On the Title Page:

In column 1 (page 4 item 56) at line 46, Under Other Publications, change "Phneumography" to --Pneumography--.

In column 2 (page 4 item 56) at line 2, Under Other Publications, change "Pelvix,"" to --Pelvis,"--.

In the Specifications:

In column 1 at line 30, Change "nucleectomy" to --nucleotomy--.

In column 2 at line 42, Change "with in" to --within--.

In column 3 at line 35, Change "fluorosis" to --fluorosis.--.

In column 3 at line 64, Change "pulposus,);" to --pulposus);--.

In column 4 at line 62, Change "nucleectomy," to --nucleotomy,--.

In column 5 at line 32, Change "co-planer" to --co-planar--.

In column 5 at line 33, Change "co-planer" to --co-planar--.

In column 6 at line 17, Change "sacrum" to --sacrum.--.

In column 7 at line 42, Change "nucleectomy" to --nucleotomy--.

In column 7 at line 45, Change "nucleectomy" to --nucleotomy--.

In column 8 at line 52, Change "dilater" to --dilator--.

In column 9 at line 50, Change "nucleectomy." to --nucleotomy.--.

In column 11 at line 58, Change "2C-2E" to --2C-2E.--.

In column 13 at line 27, Change "polyvinilydene" to --polyvinylidene--.

In column 14 at line 64, Change "introducter" to --introducer--.

In column 14 at line 65, Change "192" to --192.--.

In column 15 at line 3, Change "7A" to --7A,--.

Signed and Sealed this
Thirtieth Day of April, 2013

Teresa Stanek Rea
*Acting Director of the United States Patent and Trademark Office*

CERTIFICATE OF CORRECTION (continued)
U.S. Pat. No. 8,308,777 B2

In column 16 at line 5, Change "handel" to --handle--.

In column 16 at line 13-14, Change "polyvinilidine" to --polyvinylidene--.

In column 18 at line 65, Change "$204_4$" to --$204_L$--.

In column 21 at line 42, Change "nucleectomy" to --nucleotomy--.

In column 22 at line 10, Change "nucleectomy" to --nucleotomy--.

In column 22 at line 21, Change "chemopapain," to --chymopapain,--.

In column 22 at line 41, Change "nucleectomies" to --nucleotomies--.

In column 22 at line 45, Change "nucleectomies" to --nucleotomies--.

In column 22 at line 59, Change "nucleectomy" to --nucleotomy--.

In column 22 at line 62, Change "nucleectomy" to --nucleotomy--.

In column 23 at line 2, Change "nucleectomy" to --nucleotomy--.

In column 23 at line 11, Change "nucleectomy" to --nucleotomy--.

In column 23 at line 35, Change "16H)" to --16H).--.

In column 24 at line 7, Change "securedly" to --securely--.

In column 24 at line 59, Change "nucleectomies" to --nucleotomies--.

In column 24 at line 65, Change "example." to --example,--.

In column 25 at line 15, Change "treated" to --treated.--.

In column 27 at line 22-23, Change "nucleectomy." to --nucleotomy.--.

In column 27 at line 67, Change "mm," to --mm.--.

In column 28 at line 23, Change "perpendicular" to --perpendicular.--.

In column 29 at line 48, Change "blades's" to --blade's--.

In column 30 at line 64, Change "edges (s)" to --edge(s)--.

In column 30 at line 67, Change "edges (s)" to --edge(s)--.

In column 31 at line 5, Change "nucleectomy" to --nucleotomy--.

In column 31 at line 18, Change "nucleectomy" to --nucleotomy--.

In column 31 at line 45, Change "the a" to --the--.

In column 32 at line 50, Change "about1.50"." to --about 1.50".--.

In column 32 at line 59, Change "nickle" to --nickel--.

In column 33 at line 41, Change "enlongated" to --elongated--.

In column 34 at line 37, Change "fimaments" to --firmaments--.

In column 34 at line 64, Change "nucleectomy" to --nucleotomy--.

In column 35 at line 8, Change "nucleectomy." to --nucleotomy.--.

In column 40 at line 29, Change "885" to --885.--.

In column 43 at line 57, Change "reusuable" to --reusable--.